(12) United States Patent
Roe et al.

(10) Patent No.: US 7,736,322 B2
(45) Date of Patent: Jun. 15, 2010

(54) PRECISION DEPTH CONTROL LANCING TIP

(75) Inventors: Steven N. Roe, San Mateo, CA (US);
Chris Wiegel, San Jose, CA (US);
Hans-Juergen Kuhr, Mannheim (DE);
Wilhelm Hildebrandt, Darmstadt (DE);
Thomas Weiss, Mannheim (DE);
Richard Forster, Fensterbach (DE);
Matt Hannant, London (GB); Peter Sachsenweger, Zeitlarn (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 1267 days.

(21) Appl. No.: 10/744,167

(22) Filed: Dec. 23, 2003

(65) Prior Publication Data
US 2004/0236251 A1      Nov. 25, 2004

Related U.S. Application Data

(63) Continuation-in-part of application No. 10/330,724, filed on Dec. 27, 2002, now abandoned, and a continuation-in-part of application No. PCT/US03/04380, filed on Feb. 13, 2003, which is a continuation of application No. 10/330,724, filed on Dec. 27, 2002, now abandoned.

(51) Int. Cl.
*A61B 5/00* (2006.01)
(52) U.S. Cl. .................. 600/583; 600/573; 606/181; 606/182
(58) Field of Classification Search .......... 600/573–583; 606/181–182, 139–144, 147–148
See application file for complete search history.

(56) References Cited

U.S. PATENT DOCUMENTS

| | | | |
|---|---|---|---|
| 2,402,306 A | * | 6/1946 | Turkel .................. 604/174 |
| 2,888,924 A | | 6/1959 | Dunmire |
| 3,802,842 A | | 4/1974 | Lange et al. |
| 4,061,468 A | | 12/1977 | Lange et al. |
| 4,203,446 A | | 5/1980 | Hofert et al. |
| 4,375,815 A | | 3/1983 | Burns |
| 4,462,405 A | | 7/1984 | Ehrlich |
| 4,469,110 A | | 9/1984 | Slama |
| 4,490,465 A | | 12/1984 | Limbach et al. |

(Continued)

FOREIGN PATENT DOCUMENTS

EP          0 783 868 A1    7/1997

(Continued)

*Primary Examiner*—Max Hindenburg
*Assistant Examiner*—Rene Towa
(74) *Attorney, Agent, or Firm*—Woodard, Emhardt, Moriarty, McNett & Henry LLP

(57) ABSTRACT

A bodily fluid sampling device is operable to lance with a precise depth and express fluid from both fingertip and alternate sites. In one form, the device is operable to adjust the penetration depth of the lancet into the skin. The bodily fluid sampling device includes a lancet adapted to form an incision in skin. A skin contacting member has an orifice through which the lancet extends when lancing the skin. The orifice has a first opening size that is sized to flatten the skin around the lancet during lancing. The orifice has a second opening size that is larger than the first opening size after the incision is formed to express fluid from the incision.

24 Claims, 36 Drawing Sheets

U.S. PATENT DOCUMENTS

| | | | |
|---|---|---|---|
| 4,627,445 A | 12/1986 | Garcia et al. | |
| 4,637,403 A | 1/1987 | Garcia et al. | |
| 4,653,513 A | 3/1987 | Dombrowski | |
| 4,677,979 A | 7/1987 | Burns | |
| 4,787,398 A | 11/1988 | Garcia et al. | |
| 4,869,249 A | 9/1989 | Crossman et al. | |
| 4,895,147 A | 1/1990 | Bodicky et al. | |
| 4,924,879 A | 5/1990 | O'Brien | |
| 4,990,154 A | 2/1991 | Brown et al. | |
| 5,304,193 A | 4/1994 | Zhadanov | |
| 5,318,584 A | 6/1994 | Lange et al. | |
| 5,375,588 A * | 12/1994 | Yoon | 600/114 |
| 5,423,847 A | 6/1995 | Strong et al. | |
| 5,540,709 A | 7/1996 | Ramel | |
| 5,545,173 A | 8/1996 | Herbst | |
| 5,562,658 A * | 10/1996 | Long | 606/15 |
| 5,569,270 A * | 10/1996 | Weng | 606/144 |
| 5,582,184 A | 12/1996 | Erickson et al. | |
| 5,607,401 A | 3/1997 | Humphrey | |
| 5,613,978 A | 3/1997 | Harding | |
| 5,628,764 A | 5/1997 | Schraga | |
| 5,628,765 A | 5/1997 | Morita | |
| 5,666,966 A | 9/1997 | Horie et al. | |
| 5,709,699 A | 1/1998 | Warner | |
| 5,730,753 A | 3/1998 | Morita | |
| RE35,803 E | 5/1998 | Lange et al. | |
| 5,755,733 A | 5/1998 | Morita | |
| 5,776,719 A | 7/1998 | Douglas et al. | |
| 5,824,491 A | 10/1998 | Priest et al. | |
| 5,857,983 A | 1/1999 | Douglas et al. | |
| 5,871,494 A | 2/1999 | Simons et al. | |
| 5,873,887 A | 2/1999 | King et al. | |
| 5,879,311 A | 3/1999 | Duchon et al. | |
| 5,916,230 A | 6/1999 | Brenneman et al. | |
| 5,951,492 A | 9/1999 | Douglas et al. | |
| 5,951,493 A | 9/1999 | Douglas et al. | |
| 5,962,215 A | 10/1999 | Douglas et al. | |
| 5,964,718 A | 10/1999 | Duchon et al. | |
| 5,984,940 A | 11/1999 | Davis et al. | |
| 5,997,561 A | 12/1999 | Bocker et al. | |
| 6,015,392 A * | 1/2000 | Douglas et al. | 600/583 |
| 6,022,366 A | 2/2000 | Schraga | |
| 6,045,567 A | 4/2000 | Taylor et al. | |
| 6,048,352 A | 4/2000 | Douglas et al. | |
| 6,056,701 A | 5/2000 | Duchon et al. | |
| 6,071,294 A | 6/2000 | Simons et al. | |
| 6,086,545 A | 7/2000 | Roe et al. | |
| 6,099,484 A | 8/2000 | Douglas et al. | |
| 6,143,164 A | 11/2000 | Heller et al. | |
| 6,156,050 A | 12/2000 | Davis et al. | |
| 6,156,051 A | 12/2000 | Schraga | |
| 6,159,424 A | 12/2000 | Kauhaniemi et al. | |
| 6,168,606 B1 * | 1/2001 | Levin et al. | 606/181 |
| 6,183,489 B1 | 2/2001 | Douglas et al. | |
| 6,210,420 B1 | 4/2001 | Mauze et al. | |
| 6,210,421 B1 | 4/2001 | Bocker et al. | |
| 6,258,062 B1 | 7/2001 | Thielen et al. | |
| 6,270,637 B1 | 8/2001 | Crismore et al. | |
| 6,283,982 B1 | 9/2001 | Levaughn et al. | |
| 6,306,104 B1 | 10/2001 | Cunningham et al. | |
| 6,306,152 B1 * | 10/2001 | Verdonk et al. | 606/182 |
| 6,315,738 B1 | 11/2001 | Nishikawa et al. | |
| 6,319,210 B1 * | 11/2001 | Douglas et al. | 600/583 |
| 6,332,871 B1 | 12/2001 | Douglas et al. | |
| 6,346,114 B1 | 2/2002 | Schraga | |
| 6,379,337 B1 | 4/2002 | Owais | |
| 6,419,661 B1 | 7/2002 | Kuhr et al. | |
| 6,561,989 B2 | 5/2003 | Whitson | |
| 6,616,616 B2 | 9/2003 | Fritz et al. | |
| 6,645,219 B2 * | 11/2003 | Roe | 606/182 |
| 6,896,666 B2 | 5/2005 | Kochamba | |
| 6,929,650 B2 | 8/2005 | Fukuzawa et al. | |
| 2001/0027327 A1 | 10/2001 | Schraga | |
| 2001/0039387 A1 | 11/2001 | Rutynowski et al. | |
| 2002/0004196 A1 | 1/2002 | Whitson | |
| 2002/0029059 A1 | 3/2002 | Purcell | |
| 2002/0040230 A1 | 4/2002 | Kuhr et al. | |
| 2002/0103499 A1 | 8/2002 | Perez et al. | |
| 2002/0177763 A1 | 11/2002 | Burns et al. | |
| 2002/0177787 A1 | 11/2002 | Duchon et al. | |
| 2002/0177788 A1 | 11/2002 | Hodges et al. | |
| 2002/0188223 A1 * | 12/2002 | Perez et al. | 600/573 |
| 2003/0050573 A1 | 3/2003 | Kuhr et al. | |
| 2003/0153939 A1 | 8/2003 | Fritz et al. | |
| 2004/0034318 A1 | 2/2004 | Fritz et al. | |
| 2004/0127818 A1 | 7/2004 | Roe | |
| 2004/0267160 A9 * | 12/2004 | Perez | 600/583 |
| 2005/0085839 A1 | 4/2005 | Allen et al. | |

FOREIGN PATENT DOCUMENTS

| | | |
|---|---|---|
| EP | 0 838 195 A1 | 4/1998 |
| EP | 1 192 899 A1 | 4/2002 |
| EP | 1 358 844 | 11/2003 |
| JP | 02000116768 A2 | 4/2000 |
| WO | WO 93/09710 | 5/1993 |
| WO | WO 01/72220 A1 | 10/2001 |
| WO | WO 02/36010 | 5/2002 |
| WO | WO 02/054952 | 7/2002 |

* cited by examiner

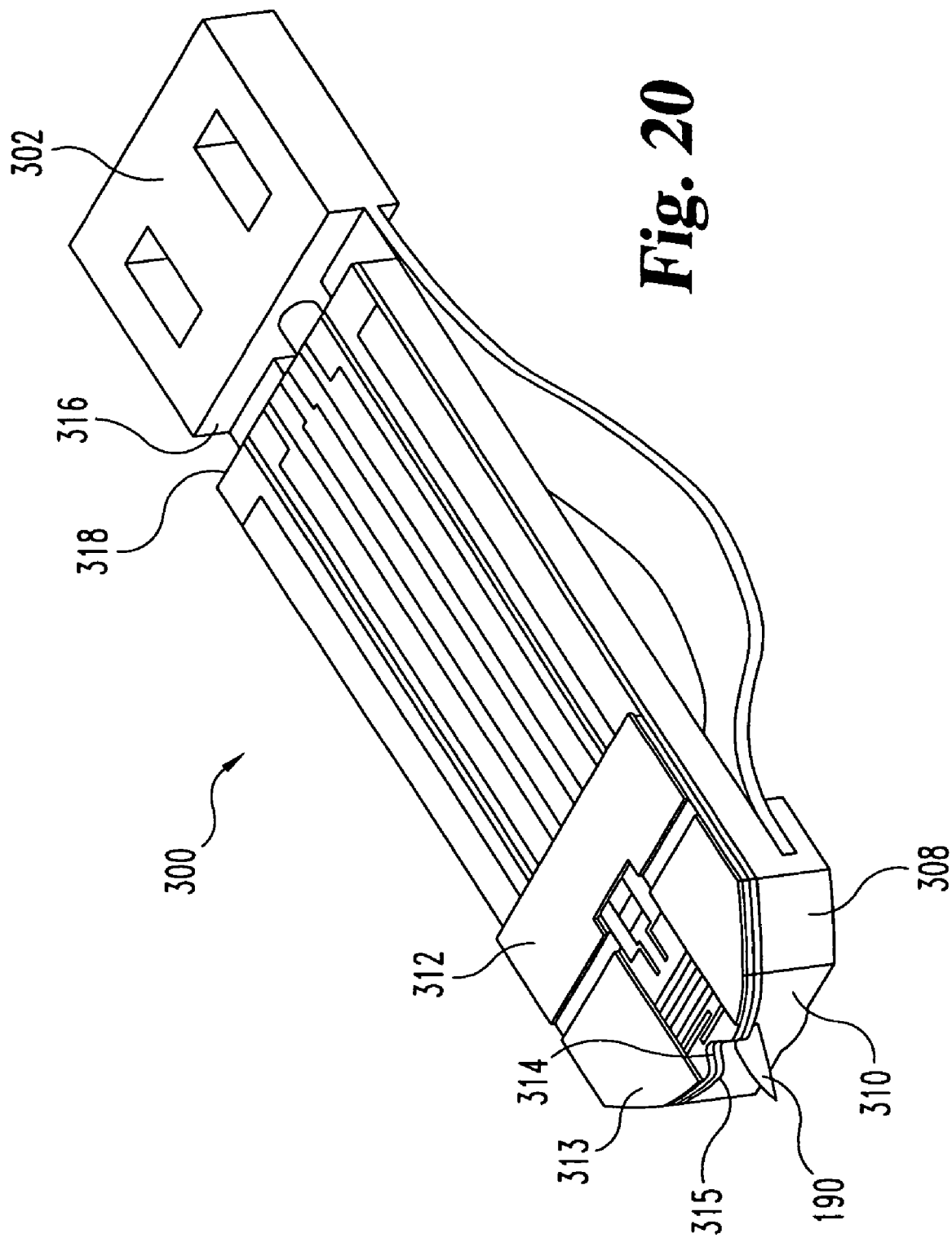

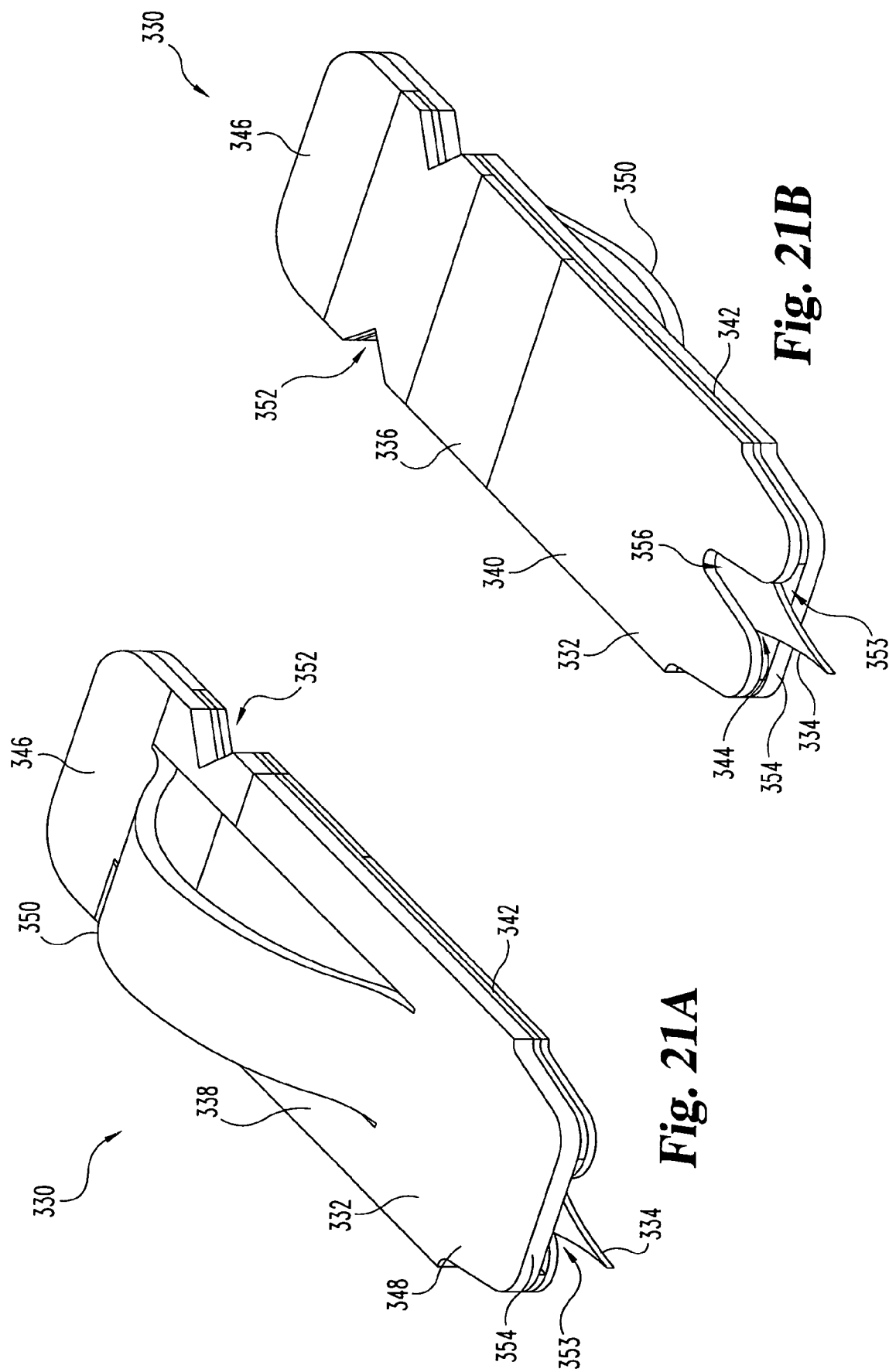

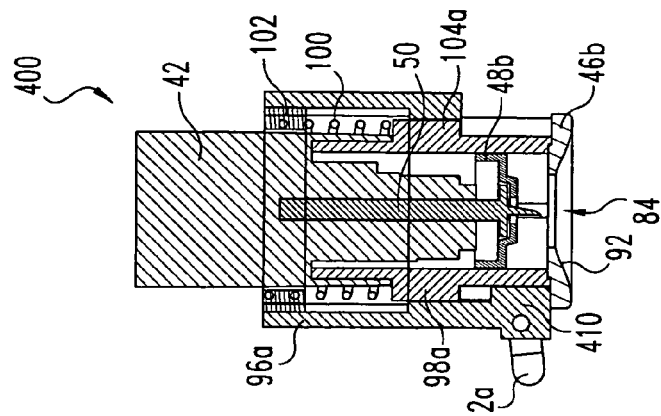
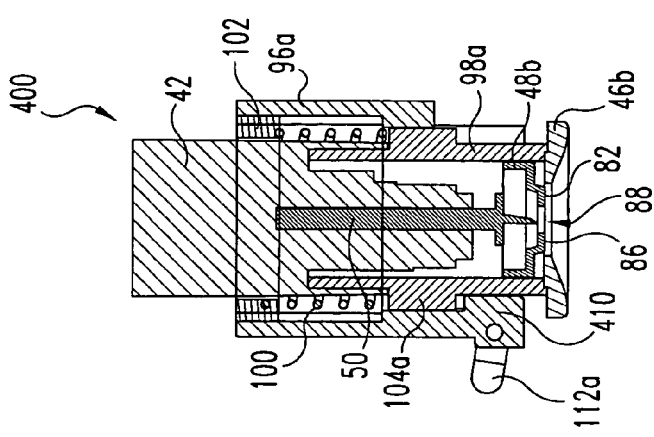
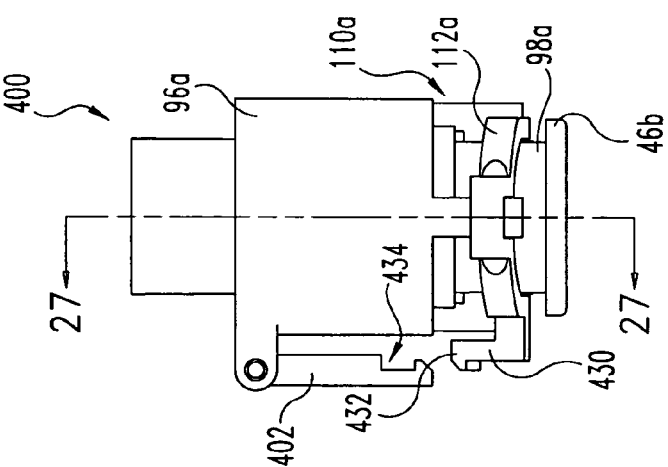
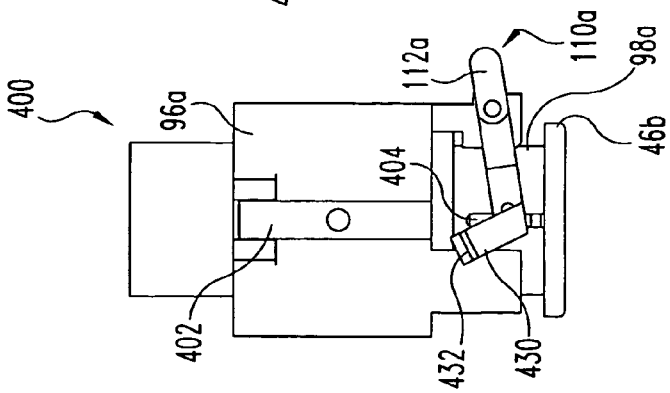

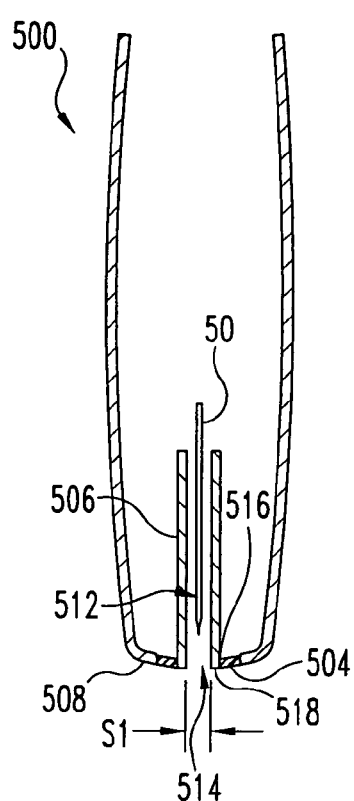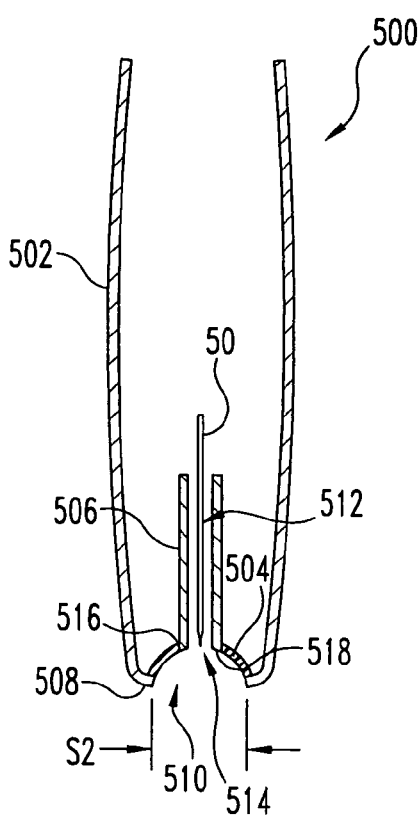
Fig. 32A  Fig. 32B
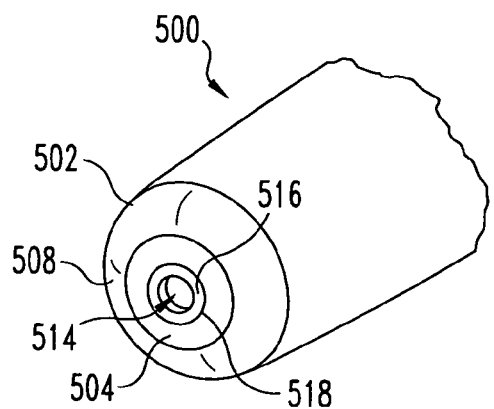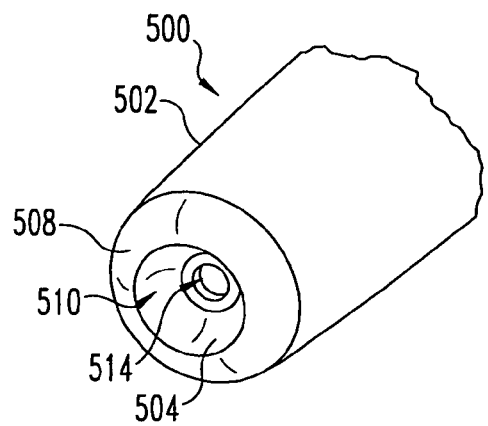
Fig. 33A  Fig. 33B

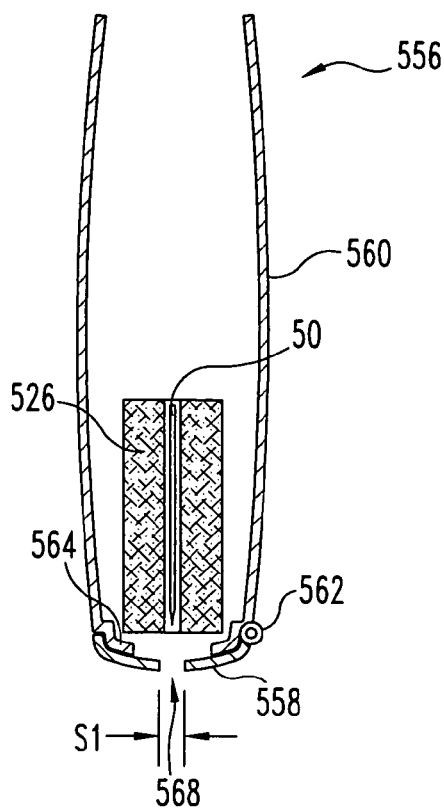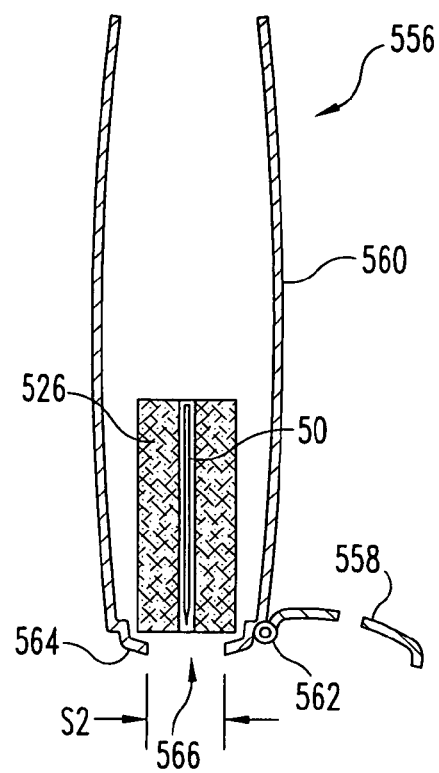
Fig. 38A  Fig. 38B
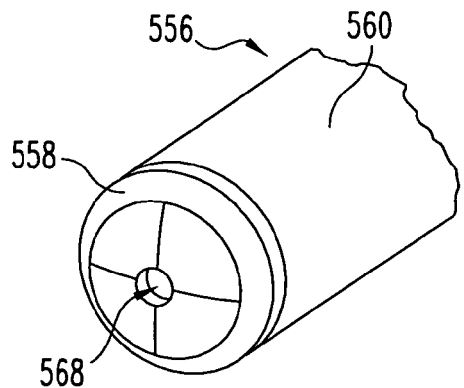
Fig. 39A
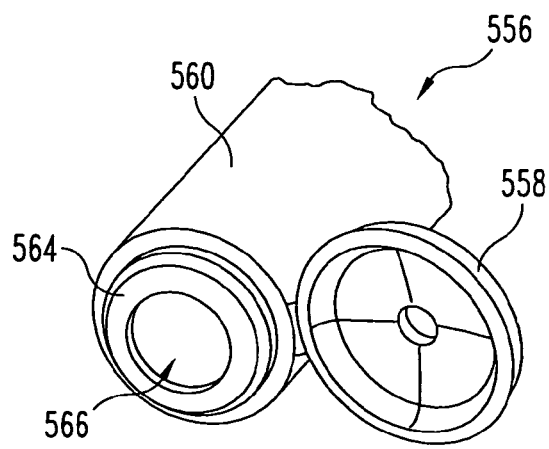
Fig. 39B

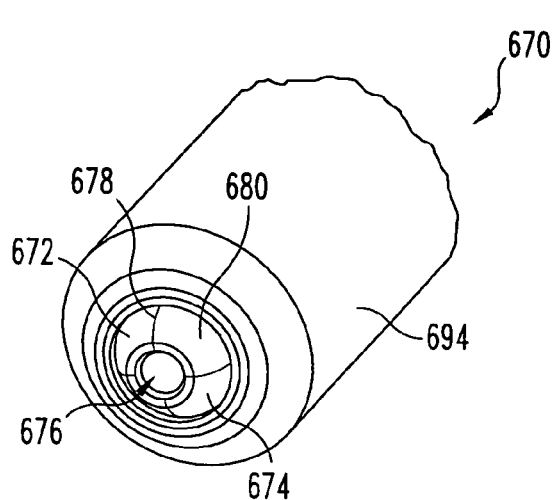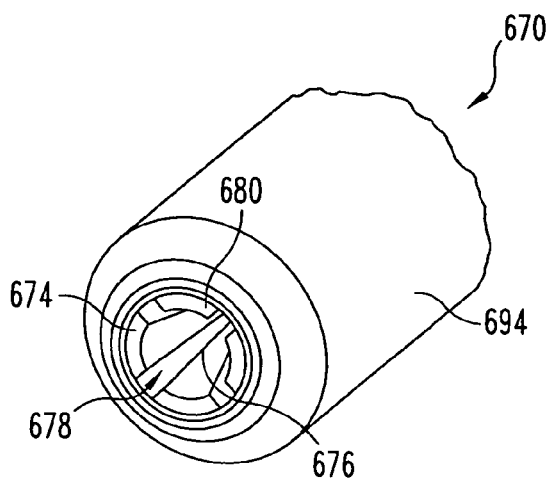
Fig. 54A    Fig. 54B
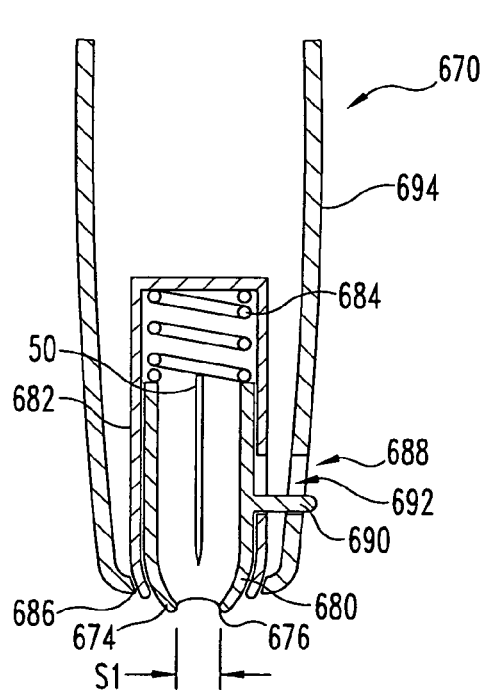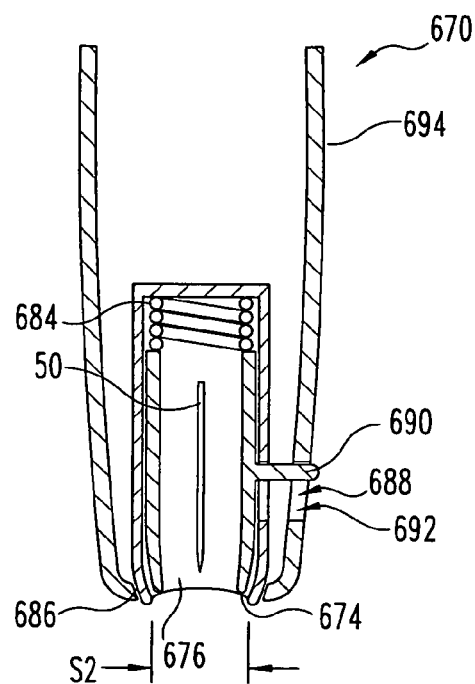
Fig. 55A    Fig. 55B

PRECISION DEPTH CONTROL LANCING TIP

REFERENCE TO RELATED APPLICATIONS

This application is a continuation-in-part of U.S. patent application Ser. No. 10/330,724, filed Dec. 27, 2002, and is a continuation-in-part of International Patent Application No., PCT/US03/04380, filed Feb. 13, 2003, which is a continuation of U.S. patent application Ser. No. 10/330,724, filed Dec. 27, 2002, all of which are hereby incorporated by reference in their entirety.

BACKGROUND OF THE INVENTION

The present invention generally relates to bodily fluid sampling devices and more specifically, but not exclusively, concerns a bodily fluid sampling device configured to form an incision having a precise depth and express fluid from both finger and alternate site testing (AST) locations.

General Fluid Testing

The acquisition and testing of bodily fluids is useful for many purposes, and continues to grow in importance for use in medical diagnosis and treatment, and in other diverse applications. In the medical field, it is desirable for lay operators to perform tests routinely, quickly and reproducibly outside of a laboratory setting, with rapid results and a readout of the resulting test information. Testing can be performed on various bodily fluids, and for certain applications is particularly related to the testing of blood and/or interstitial fluid. Such fluids can be tested for a variety of characteristics of the fluid, or analytes contained in the fluid, in order to identify a medical condition, determine therapeutic responses, assess the progress of treatment, and the like.

General Test Steps

The testing of bodily fluids basically involves the steps of obtaining the fluid sample, transferring the sample to a test device, conducting a test on the fluid sample, and displaying the results. These steps are generally performed by a plurality of separate instruments or devices.

Acquiring—Vascular

One method of acquiring the fluid sample involves inserting a hollow needle or syringe into a vein or artery in order to withdraw a blood sample. However, such direct vascular blood sampling can have several limitations, including pain, infection, and hematoma and other bleeding complications. In addition, direct vascular blood sampling is not suitable for repeating on a routine basis, can be extremely difficult and is not advised for patients to perform on themselves.

Acquiring—Incising

The other common technique for collecting a bodily fluid sample is to form an incision in the skin to bring the fluid to the skin surface. A lancet, knife or other cutting instrument is used to form the incision in the skin. The resulting blood or interstitial fluid specimen is then collected in a small tube or other container, or is placed directly in contact with a test strip. The fingertip is frequently used as the fluid source because it is highly vascularized and therefore produces a good quantity of blood. However, the fingertip also has a large concentration of nerve endings, and lancing the fingertip can therefore be painful. Alternate sampling sites, such as the palm of the hand, forearm, earlobe and the like, may be useful for sampling, and are less painful. However, they also produce lesser amounts of blood. These alternate sites therefore are generally appropriate for use only for test systems requiring relatively small amounts of fluid, or if steps are taken to facilitate the expression of the bodily fluid from the incision site.

Various methods and systems for incising the skin are known in the art. Exemplary lancing devices are shown, for example, in U.S. Pat. No. Re 35,803, issued to Lange, et al. on May 19, 1998.; U.S. Pat. No. 4,924,879, issued to O'Brien on May 15, 1990; U.S. Pat. No. 5,879,311, issued to Duchon et al. on Feb. 16, 1999; U.S. Pat. No. 5,857,983, issued to Douglas on Jan. 12, 1999; U.S. Pat. No. 6,183,489, issued to Douglas et al. on Feb. 6, 2001; U.S. Pat. No. 6,332,871, issued to Douglas et al. on Dec. 25, 2001; and U.S. Pat. No. 5,964,718, issued to Duchon et al. on Oct. 12, 1999. A representative commercial lancing device is the Accu-Chek Softclix lancet.

Expressing

Patients are frequently advised to urge fluid to the incision site, such as by applying pressure to the area surrounding the incision to milk or pump the fluid from the incision. Mechanical devices are also known to facilitate the expression of bodily fluid from an incision. Such devices are shown, for example, in U.S. Pat. No. 5,879,311, issued to Duchon et al. on Feb. 16, 1999; U.S. Pat. No. 5,857,983, issued to Douglas on Jan. 12, 1999; U.S. Pat. No. 6,183,489, issued to Douglas et al. on Feb. 6, 2001; U.S. Pat. No. 5,951,492, issued to Douglas et al. on Sep. 14, 1999; U.S. Pat. No. 5,951,493, issued to Douglas et al. on Sep. 14, 1999; U.S. Pat. No. 5,964,718, issued to Duchon et al. on Oct. 12, 1999; and U.S. Pat. No. 6,086,545, issued to Roe et al. on Jul. 11, 2000. A representative commercial product that promotes the expression of bodily fluid from an incision is the Amira AtLast blood glucose system.

Sampling

The acquisition of the produced bodily fluid, hereafter referred to as the "sampling" of the fluid, can take various forms. Once the fluid specimen comes to the skin surface at the incision, a sampling device is placed into contact with the fluid. Such devices may include, for example, systems in which a tube or test strip is either located adjacent the incision site prior to forming the incision, or is moved to the incision site shortly after the incision has been formed. A sampling tube may acquire the fluid by suction or by capillary action. Such sampling systems may include, for example, the systems shown in U.S. Pat. No. 6,048,352, issued to Douglas et al. on Apr. 11, 2000; U.S. Pat. No. 6,099,484, issued to Douglas et al. on Aug. 8, 2000; and U.S. Pat. No. 6,332,871, issued to Douglas et al. on Dec. 25, 2001. Examples of commercial sampling devices include the Roche Compact, Amira AtLast, Glucometer Elite and Therasense FreeStyle test strips.

Testing General

The bodily fluid sample may be analyzed for a variety of properties or components, as is well known in the art. For example, such analysis may be directed to hematocrit, blood glucose, coagulation, lead, iron, etc. Testing systems include such means as optical (e.g., reflectance, absorption, fluorescence, Raman, etc.), electrochemical, and magnetic means for analyzing the sampled fluid. Examples of such test systems include those in U.S. Pat. No. 5,824,491, issued to Priest et al. on Oct. 20, 1998; U.S. Pat. No. 5,962,215, issued to Douglas et al. on Oct. 5, 1999; and U.S. Pat. No. 5,776,719, issued to Douglas et al. on Jul. 7, 1998.

Typically, a test system takes advantage of a reaction between the bodily fluid to be tested and a reagent present in the test system. For example, an optical test strip will generally rely upon a color change, i.e., a change in the wavelength absorbed or reflected by dye formed by the reagent system used. See, e.g., U.S. Pat. Nos. 3,802,842; 4,061,468; and 4,490,465.

Blood Glucose

A common medical test is the measurement of blood glucose level. The glucose level can be determined directly by analysis of the blood, or indirectly by analysis of other fluids such as interstitial fluid. Diabetics are generally instructed to measure their blood glucose level several times a day, depending on the nature and severity of their diabetes. Based upon the observed pattern in the measured glucose levels, the patient and physician determine the appropriate level of insulin to be administered, also taking into account such issues as diet, exercise and other factors.

In testing for the presence of an analyte such as glucose in a bodily fluid, test systems are commonly used which take advantage of an oxidation/reduction reaction which occurs using an oxidase/peroxidase detection chemistry. The test reagent is exposed to a sample of the bodily fluid for a suitable period of time, and there is a color change if the analyte (glucose) is present. Typically, the intensity of this change is proportional to the concentration of analyte in the sample. The color of the reagent is then compared to a known standard which enables one to determine the amount of analyte present in the sample. This determination can be made, for example, by a visual check or by an instrument, such as a reflectance spectrophotometer at a selected wavelength, or a blood glucose meter. Electrochemical and other systems are also well known for testing bodily fluids for properties on constituents.

Alternate Site Testing (AST)

As mentioned above, the fingertip is frequently used as the fluid source because it is highly vascularized and therefore produces a good quantity of blood. However, the fingertip also has a large concentration of nerve endings, and lancing the fingertip can therefore be painful. Alternate sampling sites, such as the palm of the hand, forearm, earlobe and the like, may be useful for sampling, and are less painful. However, they also produce less blood when lanced.

In general, bodily fluid sampling devices are designed to express blood from either the fingertip or an alternate site, but not both. Typically, alternate site sampling devices need to express fluid from a large surface area surrounding the site in order to draw a sufficient amount of fluid for testing. Furthermore, it is usually more desirable to lance the skin deeply at the alternate site in order to ensure that a sufficient amount of fluid can be expressed. In comparison, fingertips are relatively small and do not need to be deeply lanced or require a large area in order to express a sufficient amount of fluid. Therefore, alternate site sampling devices usually have larger openings for expressing fluid as compared to devices designed to express fluid from fingers. If an alternate site sampling device were used to lance and express fluid from a fingertip, severe pain or serious injury to the finger may result. With the alternate site device, when an incision is being formed in the fingertip, the skin can tend to deform or bulge into the expression opening such that the lancet forms an incision with a greater depth than needed.

Thus, needs remain for further contributions in this area of technology.

SUMMARY OF THE INVENTION

One form of the present invention concerns a bodily fluid sampling device that includes an incision forming member adapted to form an incision in skin. An expression member defines an expression opening configured to express fluid from the incision. A reference member defines an aperture through which the incision forming member extends when forming the incision. The reference member has a reference surface received in the expression opening during formation of the incision to contact the skin and limit penetration depth of the incision forming member into the skin. A retraction mechanism is coupled to the reference member to retract the reference surface from the expression opening.

Another form concerns a body fluid sampling device that includes a lancet to form an incision in skin and a first member configured to contact the skin during lancing. The first member defines a lancet opening through which the lancet extends during lancing, and the lancet opening is sized to generally flatten the skin around the lancet during lancing. A second member is coupled to the first member, and the second member defines an expression opening that is sized larger than the lancet opening to express fluid from the incision.

A further form concerns a body fluid sampling device that includes a housing and a lancet disposed in the housing to lance skin. A member is coupled to the housing, and the member defines a lancet opening sized to flatten the skin around the lancet during lancing. The member defines an expression opening that is sized larger than the lancet opening to express fluid from alternate sites.

Still yet a further form concerns a body fluid sampling device that includes means for rupturing skin and means for providing a first opening size to flatten the skin during rupturing. The device further includes means for providing a second opening size larger than the first opening size to express fluid.

Another form concerns a method in which an incision is lanced in skin with a lancet of a sampling device. The penetration depth of the lancet is controlled by flattening skin around the lancet with a lancet opening of the device during the lancing. Fluid is expressed from the incision by pressing an expression opening of the sampling device around the incision, and the expression opening is larger than the lancet opening.

A further form concerns a method in which a sampling device includes a lancet and a lancet opening that is sized to generally flatten skin around the lancet during lancing. The sampling device has an expression opening that is sized larger than the lancet opening to express fluid. The sampling device is adjusted so that the expression opening is able to express the fluid. An incision is formed in the skin with the lancet. The fluid is expressed from the incision by pressing the expression opening around the incision.

Further forms, objects, features, aspects, benefits, advantages, and embodiments of the present invention will become apparent from a detailed description and drawings provided herewith.

BRIEF DESCRIPTION OF THE DRAWINGS

FIG. 20 is a bottom perspective view of the FIG. 18 device in a lancing position.

FIG. 21A is a top perspective view of a sampling device according to a further embodiment.

FIG. 21B is a bottom perspective view of the FIG. 21A device.

FIG. 25 is a front view of the FIG. 23 device.

FIG. 26 is a side view of the FIG. 23 device.

FIG. 27 is a cross-sectional view of the FIG. 23 device configured to express fluid from a fingertip.

FIG. 28 is a cross-sectional view of the FIG. 23 device configured to express fluid from an alternate site.

FIGS. 32A and 32B are cross sectional views of a sampling device according to another embodiment in lancing and expressing configurations, respectively.

FIGS. 33A and 33B are perspective views of the FIGS. 32A and 32B device in the lancing and expressing configurations, respectively.

FIGS. 38A and 38B are cross sectional views of a sampling device according to a further embodiment in lancing and expressing configurations, respectively.

FIGS. 39A and 39B are perspective views of the FIGS. 38A and 38B device in the lancing and expressing configurations, respectively.

FIGS. 54A and 54B are perspective views of a sampling device according to a further embodiment in lancing and expressing configurations, respectively.

FIGS. 55A and 55B are cross sectional views of the FIGS. 54A and 54B device in the lancing and expressing configurations, respectively.

DESCRIPTION OF THE SELECTED EMBODIMENTS

Figure 1:
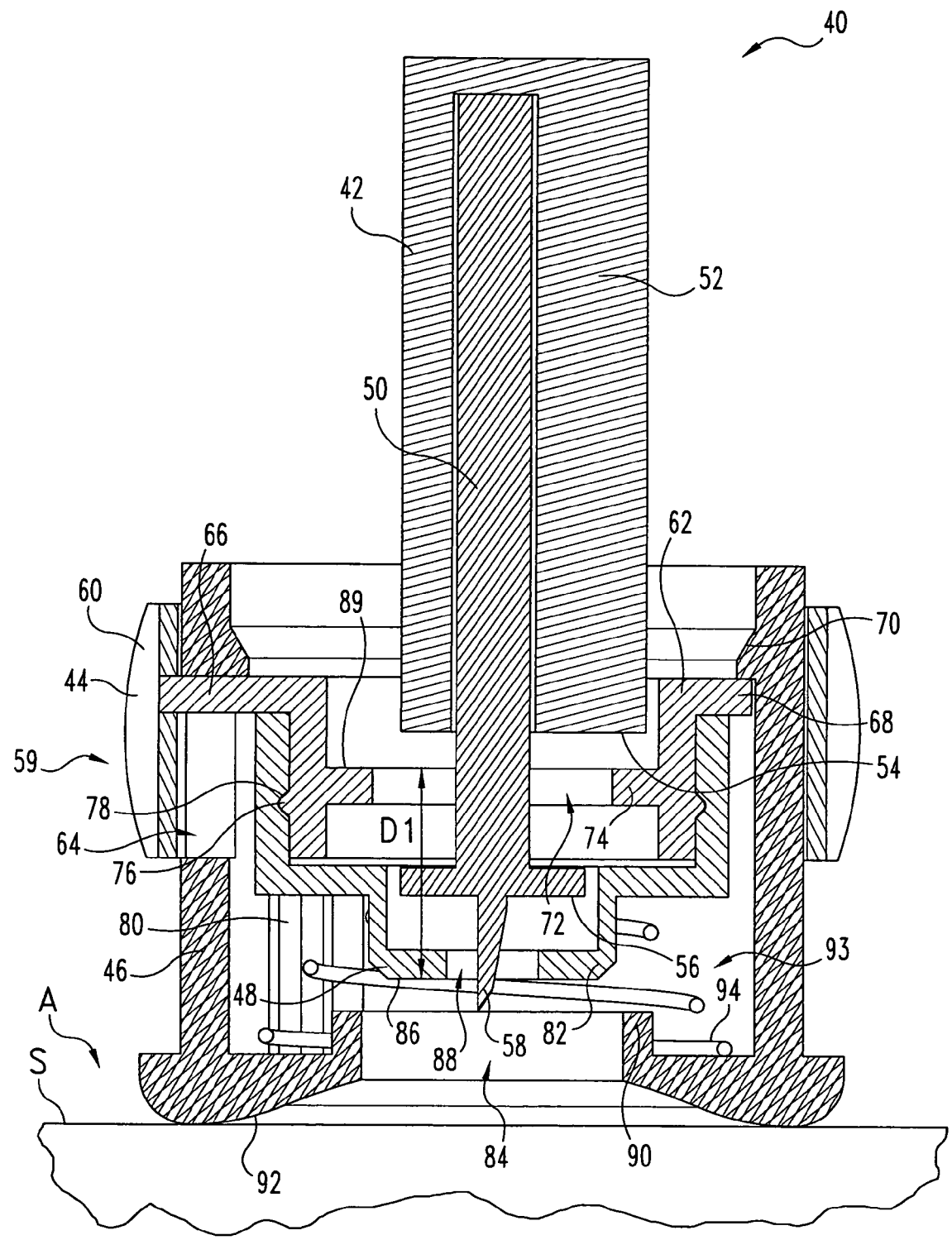
FIG. 1 is a cross-sectional view of a bodily fluid sampling device according to one embodiment of the present invention.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates. One embodiment of the invention is shown in great detail, although it will be apparent to those skilled in the relevant art that some features that are not relevant to the present invention may not be shown for the sake of clarity.

Bodily fluid sampling devices according to the present invention are operable to form an incision with a precise depth and express fluid from both fingertip and alternate sites. The devices can further be configured to allow for the adjustment of the penetration depth of the lancet. In one particular embodiment, the device includes a reference member that provides a reference surface for controlling the penetration depth of a lancet. The reference member is received in a large expression opening of an expression member. During lancing, the reference member flattens the skin in the expression opening such that an incision with a precise depth can be formed. After lancing the skin, the reference member can be retracted from the expression opening so that the larger expression opening can be used to express a sufficient amount of bodily fluid from the alternate site. In one form, a spring automatically retracts the reference member after lancing, and in other forms, cam mechanisms are used to retract the reference member during expression of the fluid. In other embodiments, the reference member is coupled to the lancet in order to control the penetration depth of the lancet. Further aspects of the present concern integrated sampling devices that allow test media to be attached to the lancet after sterilization so as to ensure that the test media remains properly calibrated.

A bodily fluid sampling device 40 according to one embodiment of the present invention is illustrated in FIGS. 1-5. Referring to FIG. 1, the sampling device 40 includes an incision forming member 42, a penetration depth adjuster 44, an expression member 46, and a reference member 48. For the sake of clarity and brevity, other components of the sampling device 40 that are well know in the art, such has hammers, cocking mechanisms and the like that are not important to appreciate the present invention, will not be discussed below. For examples of such components, please refer to U.S. Pat. No. 5,964,718, issued to Duchon et al. on Oct. 12, 1999, which is hereby incorporated by reference in its entirety. The device 40 illustrated in FIG. 1 can be back loaded into a sampling device of the type described in U.S. Pat. No. 5,964, 718.

As shown in FIG. 1, the incision forming member 42 has a lancet 58 that is attached to a lancet body 50. In the illustrated embodiment, the lancet 50 is in the form of a needle. However, it should be appreciated that the lancet 50 can come in other forms, such as a blade. Moreover, although a single lancet is shown, the incision forming member 42 in other embodiments can include multiple lancets 50. As depicted in FIG. 1, the lancet body 52 has a depth stop surface 54, which is used to control the penetration depth of the lancet 50. The lancet 50 further includes a flange 56 positioned proximal to tip 58 of the lancet 50, which is configured to cut the skin S. In one form of the present invention, the flange 56 can be used as an auxiliary stop in order to prevent over penetration of the lancet 50 into the skin S.

With continued reference to FIG. 1, the sampling device 40 has a depth control assembly 59 that is able to adjust the penetration depth of the lancet 50. The depth control assembly 58 includes adjuster 44 and reference member 48. As depicted, the adjuster 44 has an outer adjustment member 60 attached to an inner adjustment member 62 that interfaces with the reference member 48. The outer expression member 46 defines a slot 64 through which arm 66 of the adjuster 44 connects the outer adjustment member 60 to the inner adjustment member 62. The outer adjustment member 60 in the illustrated embodiment is in the form of a ring that encircles the outer expression member 46. To adjust the penetration depth of the lancet 50, the user rotates the outer adjustment member 60 around the device 40. The inner adjustment member 62 further incorporates an outwardly extending flange 68 that engages an inwardly extending flange 70 in the outer expression member 46. As shown in FIG. 1, the inner adjustment member 62 defines an inner passageway 72 through which the lancet 50 extends. Inside passageway 72, the inner adjustment member 62 has a stop flange 74 that is configured to engage the stop surface 54 on the incision forming member 42.

As depicted, the inner adjustment member 62 has at least one thread 76 that engages a corresponding groove 78 formed in the reference member 48. As should be appreciated, in other embodiments, the reference member 48 can be threaded and the inner adjustment member 62 can have corresponding grooves. Although the reference member 48 surrounds the inner adjustment member 62 in the illustrated embodiment, at least a portion of the reference member 48 in other embodiments can be received inside the inner adjustment member 62. To prevent the reference member 48 from rotating with the adjuster 44 when the penetration depth is adjusted, the outer expression member 46 has a slot 80 that engages the reference member 48.

Referring to FIG. 1, the reference member 48 has a contact portion 82 that is adapted to extend through expression opening 84 that is defined in the expression member 46. The contact portion 82 has a skin contacting surface 86 that contacts the skin S when the incision is formed by the lancet 50. Surface 86 surrounds an aperture 88 through which tip 58 of the lancet 50 extends. Distance D1 between the skin contacting surface 86 and stop surface 89 on the stop flange 74 of the adjuster 44 controls the penetration depth of the lancet 50. Rotating the outer adjustment member 60 changes distance D1, thereby changing the penetration depth of the lancet 50.

Extending around opening 84 in the outer expression member 46 is a ridge 90 that is adapted to engage the reference member 48 so as to control how far the contact portion 82 extends from the expression member 46. The outer expression member 46 further has an expression surface 92 that is angled or inclined towards opening 84 in order to promote expression of bodily fluid. In one form, the expression surface 92 has a generally frusto-conical shape. An opening size adjustment or retraction mechanism 93 is used to retract reference member 48 from the expression opening 84 so as to change the opening size for expressing fluid. In the illustrated embodiment, mechanism 93 includes a spring 94. As will be appreciated from the discussion below concerning the other embodiments, other types of size adjustment mechanisms 93 can be used to change the size of the opening for expressing fluid. Spring 94, which is positioned between the outer expression member 46 and the reference member 48, biases the reference member 48 along with the adjuster 44 against flange 70 so that the contact portion 82 is positioned out of the expression opening 84.

As mentioned above, alternate sampling sites A, such as the palm of the hand, forearm, earlobe and the like, may be useful for sampling because lancing these sites tends to be less painful. However, one drawback with the alternate site A is that the amount of fluid that can be expressed from an incision formed in that area is relatively small when compared to fingertip sites. One solution has been to increase the opening size in an expression ring so as to increase the area in which fluid is expressed from the skin. However, due to the larger opening size, the skin tends to bulge to a greater degree, thereby increasing the penetration depth of the lancet by a variable amount when the incision is formed at the alternate site A. In device 40, the expression opening 84 is sized to express a sufficient amount of fluid for testing from the alternate site A. In comparison to the expression opening 84, the aperture 88 in the reference member 48 is relatively small. In one embodiment, the aperture 88 is sized to be slightly larger than the lancet tip 58 such that the lancet 50 is able to slide through the aperture 88. The size of the reference member 48 minimizes skin deformation around the lancet 50 when piercing the skin S, thereby ensuring the device 40 forms incisions with substantially consistent depths.

Figure 2:
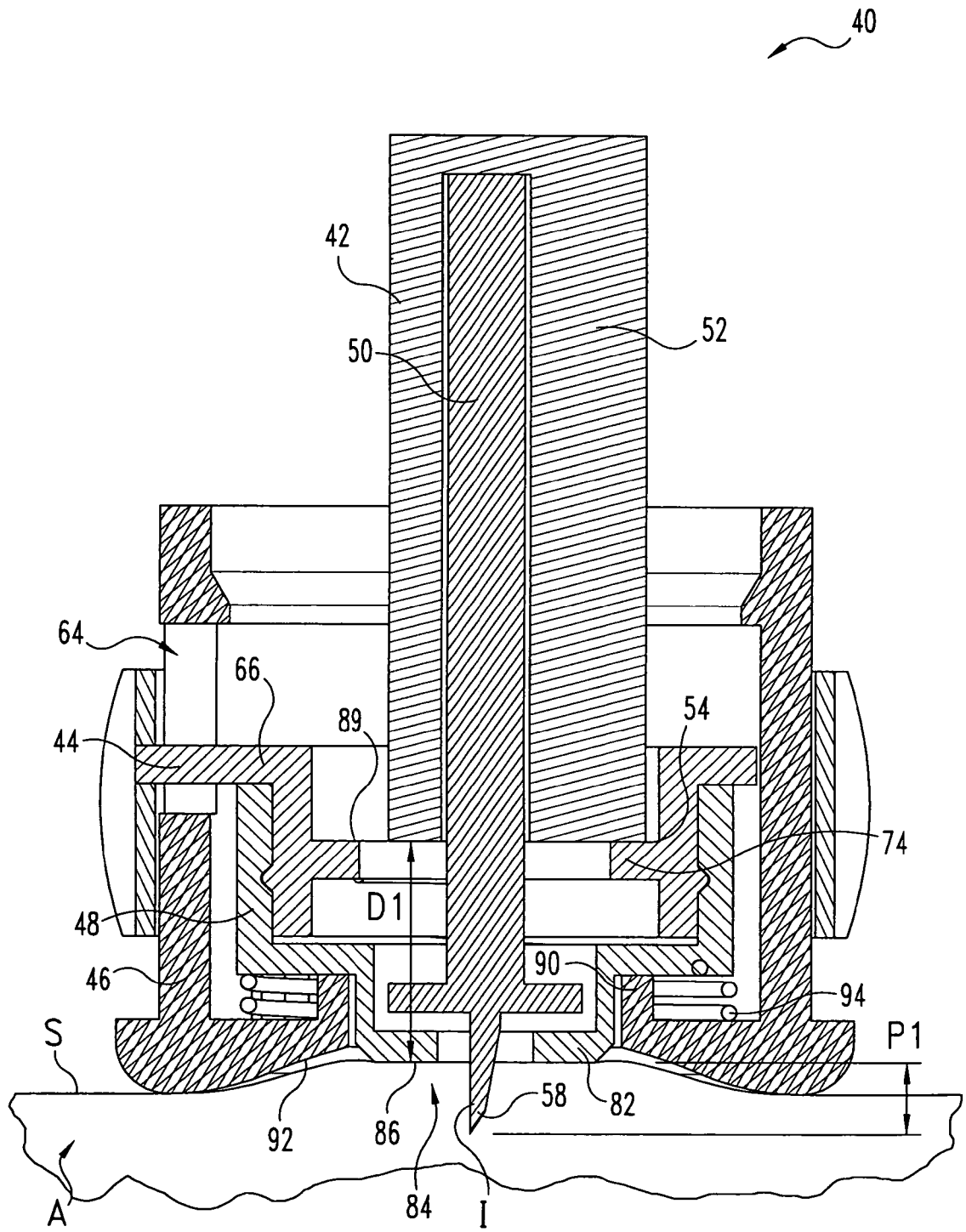
FIG. 2 is a cross-sectional view of the FIG. 1 device during lancing at an alternate site.

During lancing, as shown in FIG. 2, the incision forming member 42 is actuated to move towards the skin S. As should be understood, the incision forming member 42 can be driven towards the skin S through a number of mechanisms, such as for example by a hammer striking the incision forming member 42. As the incision forming member 42 moves toward the skin S, the stop surface 54 of the incision forming member 42 contacts the inner flange 74 of the adjuster 44 such that the reference member 48 is driven toward the skin S. While the adjuster 44 and the reference member 48 are driven towards the skin S, the arm 66 of the adjuster 44 slides within the slot 64 of the outer expression member 46. In FIG. 2, the contact portion 84 of the reference member 82 extends through the expression opening 84 such that the skin contacting surface 86 of the reference member 48 contacts and flattens the skin S surrounding the lancet 50 as incision I is formed. As previously discussed, the distance D1 between the skin contacting surface 86 and the stop surface 89 of the stop flange 74 controls the penetration depth P1 of the lancet 50 in to the skin S.

Figure 3:
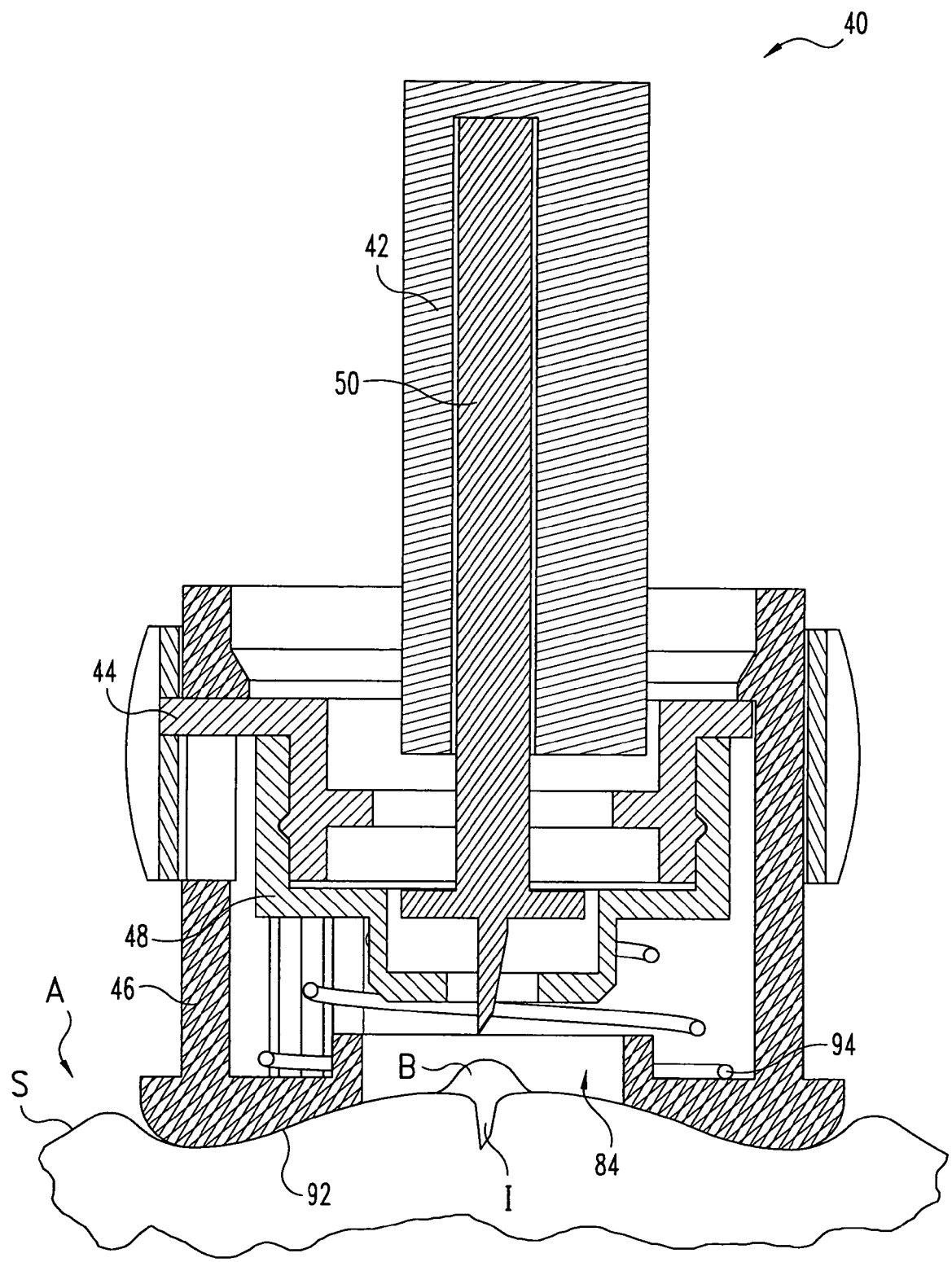
FIG. 3 is a cross-sectional view of the FIG. 1 device expressing fluid from the alternate site.

Referring to FIG. 3, after the incision I is formed in the skin S, the spring 94 retracts the reference member 48 from the expression opening 84. The user is able to express bodily fluid B from the incision I using the larger expression opening 84. As should be appreciated from the discussion above, this design allows a greater amount of fluid to be expressed from an alternate site A, while at the same time forms an incision having precise depth.

Figure 4:
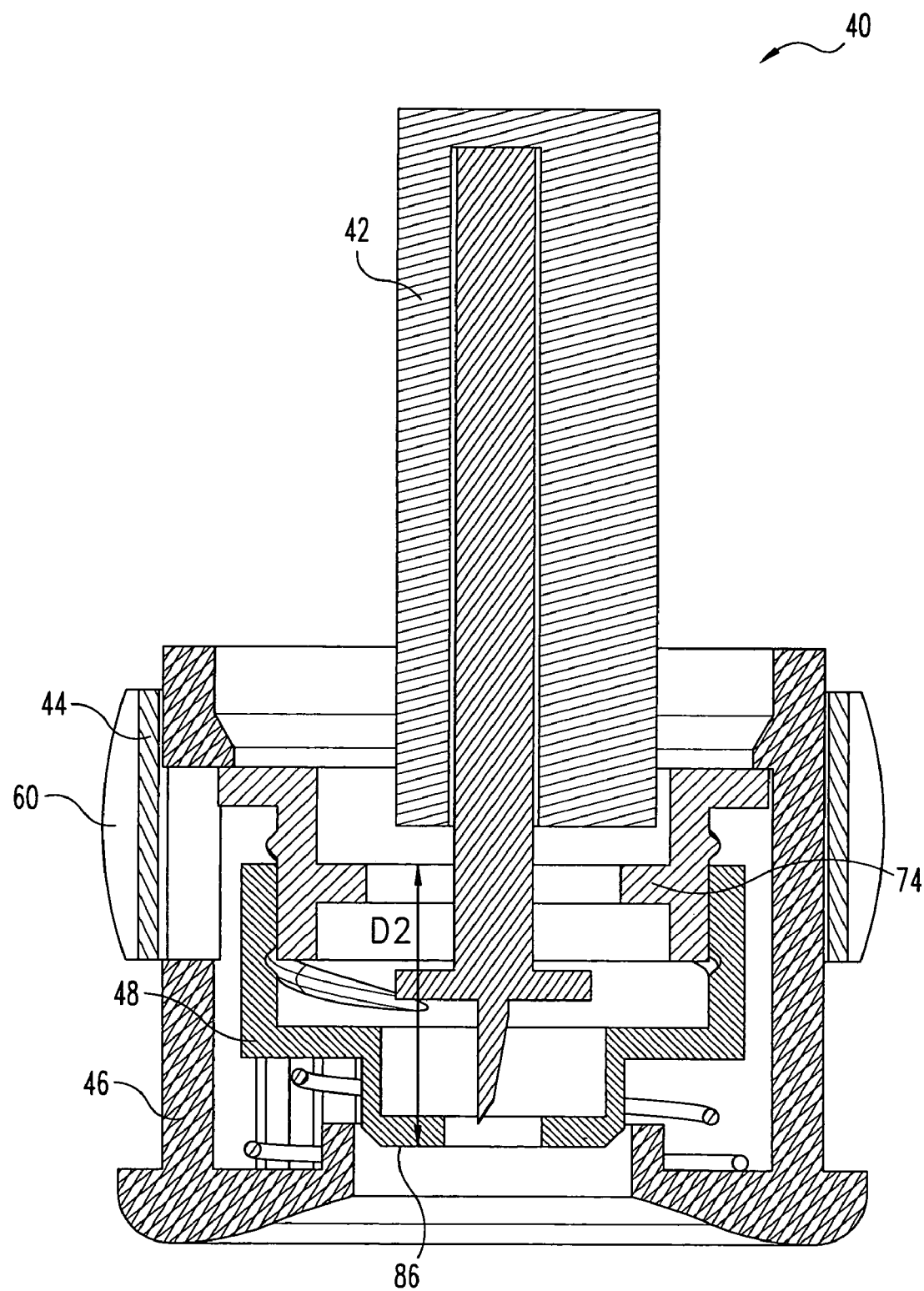
FIG. 4 is a cross-sectional view of the FIG. 1 device configured to lance.
Figure 5:
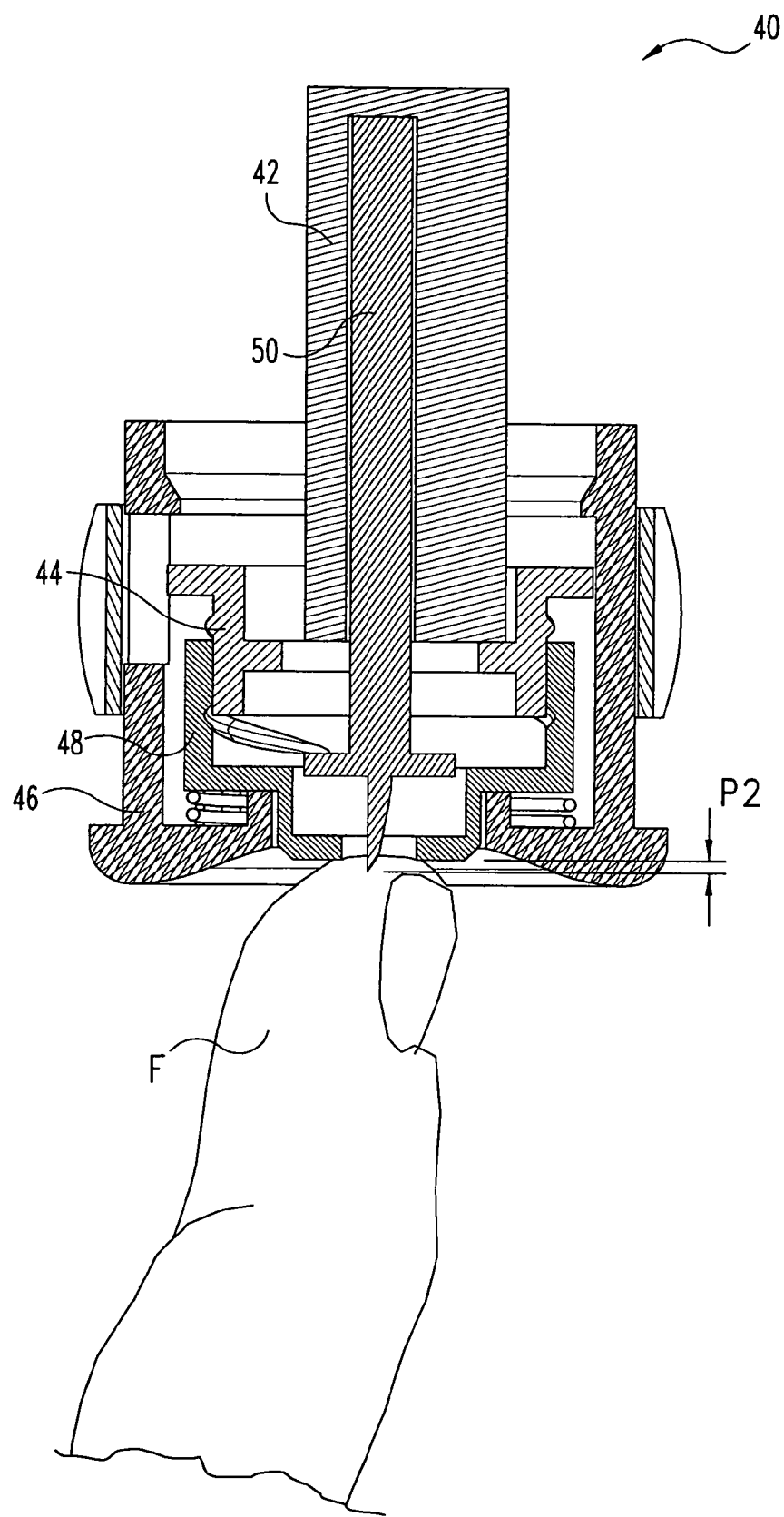
FIG. 5 is a cross-sectional view of the FIG. 1 device lancing a fingertip site.

As discussed above, the penetration depth of the lancet 50 can be adjusted by rotating the outer adjustment member 60 of the adjuster 44. As illustrated in FIG. 4, rotating the outer adjustment member 60 of the adjuster 44 extends the reference member 48 from the adjuster 44, thereby increasing distance D2 between the skin contacting surface 86 of the reference member 48 and the flange 74 of the adjuster 44. Increasing distance D2 in turn reduces the penetration depth P2 of the lancet 50, as is illustrated in FIG. 5. Reducing the penetration depth P2 can help reduce the pain associated with lancing at especially sensitive sites, such as fingertip site F.

Figure 7:
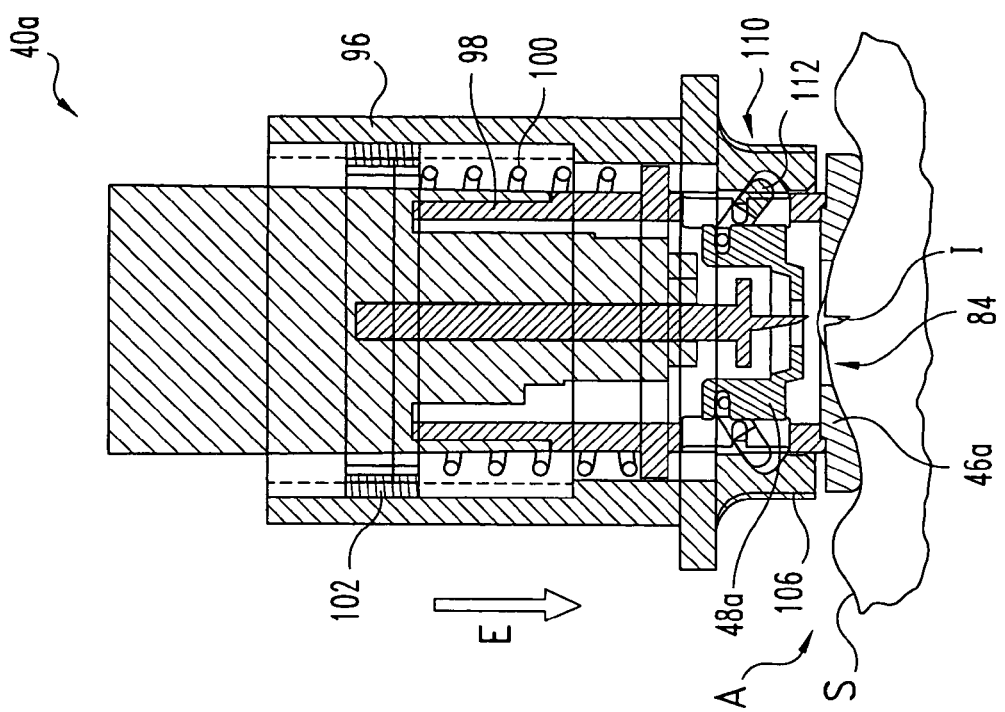
FIG. 7 is a cross-sectional view of the FIG. 6 device configured to express fluid from an alternate site.
Figure 6:
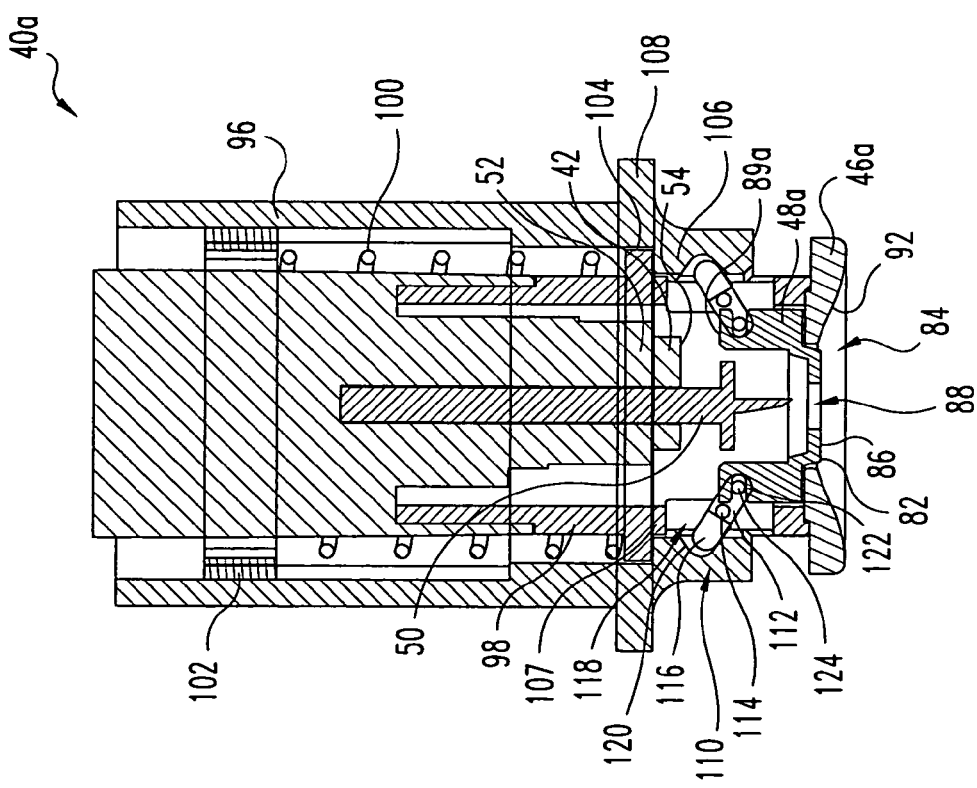
FIG. 6 is a cross-sectional view of a bodily fluid sampling device according to according to another embodiment.
Figure 9:
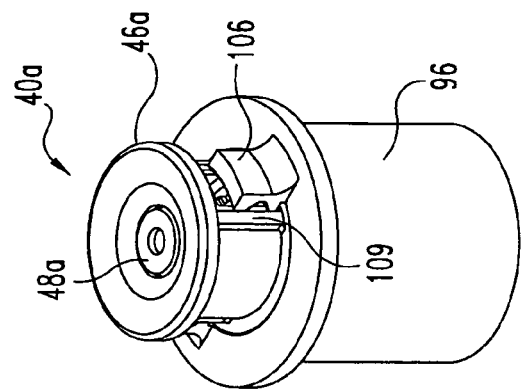
FIG. 9 is a perspective view of the FIG. 6 device.
Figure 8:
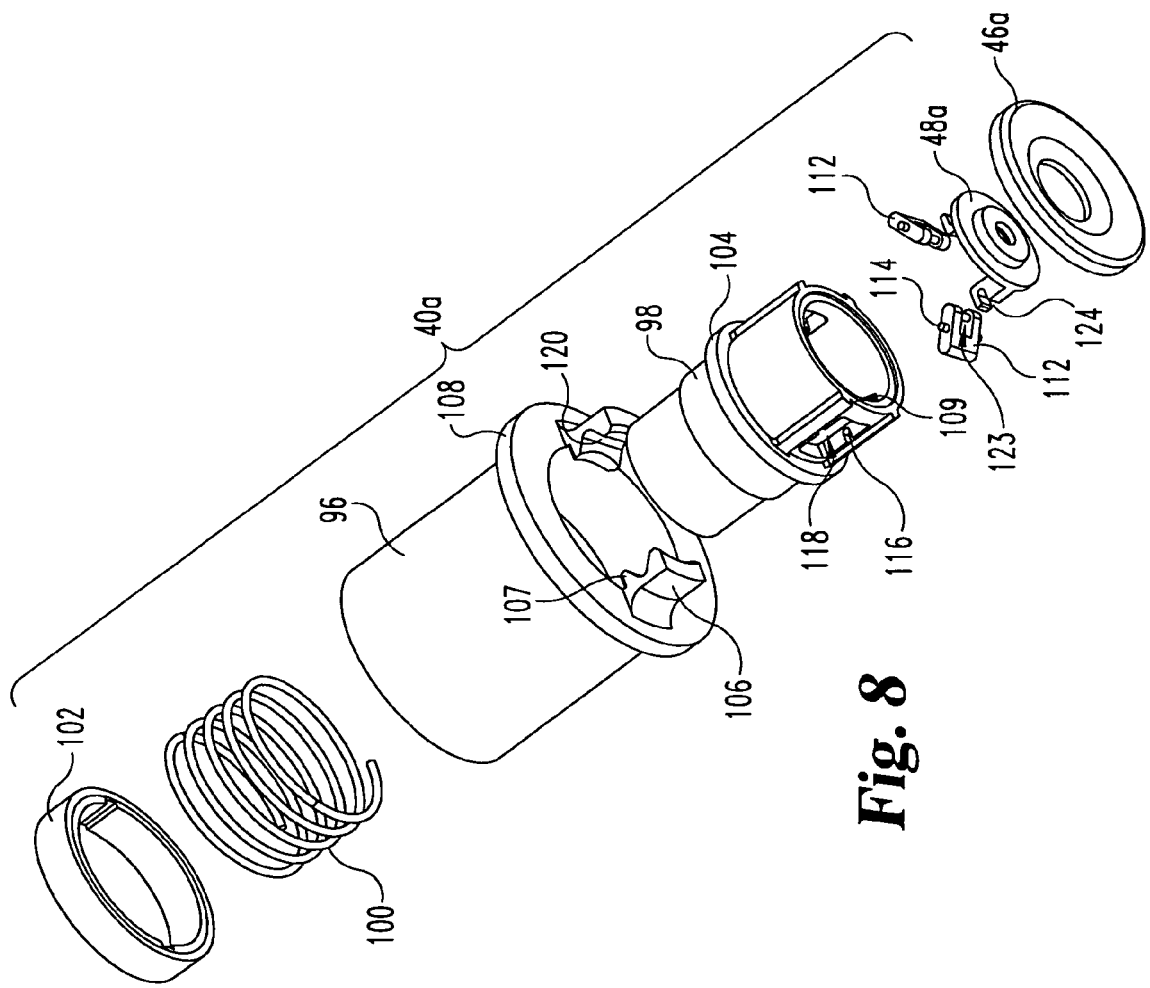
FIG. 8 is an exploded view of the FIG. 6 device.

A bodily fluid sampling device 40a according to another embodiment of the present invention will now be described with reference to FIGS. 6-9. The sampling device 40a of the illustrated embodiment is configured to automatically increase the size of the expression opening when fluid is expressed from an alternate site. As illustrated in FIGS. 6 and 8, the sampling device 40a includes a sleeve 96 that encloses incision forming member 42, which has lancet 50 and lancet body 52, of the type described above. In the illustrated embodiment, surface 54 of the lancet body 52 does not act as an end stop for controlling the penetration depth of the lancet 50. Rather, a fixed stop inside the mechanism that is used to actuate the lancet 50 controls the penetration depth. For instance, device 40a can be incorporated into a SOFTCLIX brand lancing device (Boehringer Mannheim GmbH Corporation, Germany) in order to actuate and control the penetration depth of the lancet 50. It is contemplated, however, that device 40a can be modified such that surface 54 of the lancet body 52 can act as a stop surface for controlling the penetration depth of the lancet 50. In FIG. 6, the sleeve 96 is slidable over a lancet housing 98. As shown, the lancet housing 98 encloses the incision forming member 42. A spring 100 is operatively positioned between the sleeve 96 and the housing 98 for biasing the sleeve 96. In FIG. 6 and 8, the sleeve 96 is attached to a nut or inner flange 102 against which the spring 100 engages, and in a similar fashion, the housing 98 has an outwardly extending flange 104 that engages the spring 100. In one form, the nut 102 threadedly engages the sleeve 96, and in another embodiment, the nut 102 is integrally formed with the sleeve 96. As should be understood, nut 102 and flange 104 can be attached in other manners. The sleeve 96 further includes one or more guide arms 106 that longitudinally extend from the sleeve 96. In the illustrated embodiment, the sleeve 96 has a pair of guide arms 106. However, it should be appreciated that the sleeve 96 can have a different number of guide arms 106 in other embodiments. Each guide arm 106 has an end stop member 107 that extends in an inward radial direction so as to engage flange 104 of the housing 98. The sleeve 96 further has an outer collar 108 that assists the user in gripping the sleeve 96. To prevent rotation of the housing 98 relative to the sleeve 96, the housing 98 has guide ridges 109 that longitudinally extend on opposite sides of the guide arms 106, as shown in FIG. 8.

Similar to the above described embodiment, the sampling device 40a illustrated in FIGS. 6-9 includes an outer expression member or tip 46a as well as a reference member 48a. As shown, the reference member 48a has aperture 88 and skin contacting portion 82 with skin contacting surface 86. Like the embodiment before, the expression tip 46a has angled expression surface 92 that surrounds expression opening 84. In the illustrated embodiment, the expression tip 46a is glued to the housing 98, and in the another embodiment, the expression tip 46a is integrally formed with the housing 98. It should be understood that the expression tip 46a can be attached to the housing 98 in other manners as generally know by those skilled in the art. As mentioned above, the penetration depth of the lancet 50 is control by a fixed stop in the actuation mechanism, such as with a SOFTCLIX brand lancing device. It contemplated that the lancet 50 in the sampling device 40a can be constructed to have a fixed penetration depth or an adjustable penetration depth, as in the manner described above for the previous embodiment by adjusting registration between the reference member 48a and the lancet body 52.

As mentioned above, the sampling device 40a of the embodiment illustrated in FIGS. 6-9 is designed to automatically retract the skin contacting portion 82 of the reference member 48a from the expression opening 84 when expressing fluid from an alternate site A. Normally, as depicted in FIG. 6, the skin contacting portion 82 of the reference member 48a is positioned within the expression opening 84. To automatically retract the reference member 48a, the sampling device 40a incorporates a retraction mechanism 110 that includes one or more cam arms 112 pivotally mounted to the housing 98. In the illustrated embodiment, the retraction mechanism 110 incorporates a pair of cam arms 112, but it should be appreciated that the retraction mechanism 110 can have more or less cam arms 112 than is shown. As depicted in FIGS. 6 and 8, the cam arms 112 pivot about housing pivot pins 114, which are received in pivot slots 116 defined in the housing 98. Each of the cam arms 112 extend through cam arm openings 118 in the housing 98 and engage at one end a cam groove or surface 120 that is defined in the guide arms 106. The other end of each of the cam arm 112 is engage with the reference member 48a through aperture pin 122 that is received in cam slot 124 defined in the reference member 48a. In the illustrated embodiment, pin 122 extends within a cavity 123 (FIG. 8) defined in each cam arm 122.

During lancing, the skin contacting portion 82 of the reference member 48a is positioned in the expression opening 84 in order to control the penetration depth of the lancet 50. As illustrated in FIG. 6, the spring 100 biases the sleeve 96 away from the expression tip 46a which in turn, through the guide arms 106, orients the cam arms 112 so as to position the reference member 48a in the expression opening 84. When expressing bodily fluid from an incision I formed at an alternate site A, the skin contacting portion 82 of the reference member 48a is retracted from the expression opening 84 such that the bodily fluid can be expressed from the alternate site using the wider expression opening 84. To retract the reference member during expression, the user grasps the device 40a by sleeve 96 and presses the expression tip 46a against the skin S. Referring to FIG. 7, while the device 40a is pressed against the skin S, the sleeve 96 slides in direction E along the housing 98, and the spring 100 becomes compressed. The stiffness of the spring 100 is selected such that spring 100 will compress during expression, but will typically not compress during lancing. As the sleeve 96 slides along the housing 98, the guide arms 106 pivot the cam arms 112 such that the reference member 48a is retracted into the device 40a. Once the user ceases pressing the device 40a against the skin S, the spring 100 returns the sleeve 96 to the original position shown in FIG. 6, and the cam arms 112 return the reference member 48a back into the expression opening 84.

Figure 10:
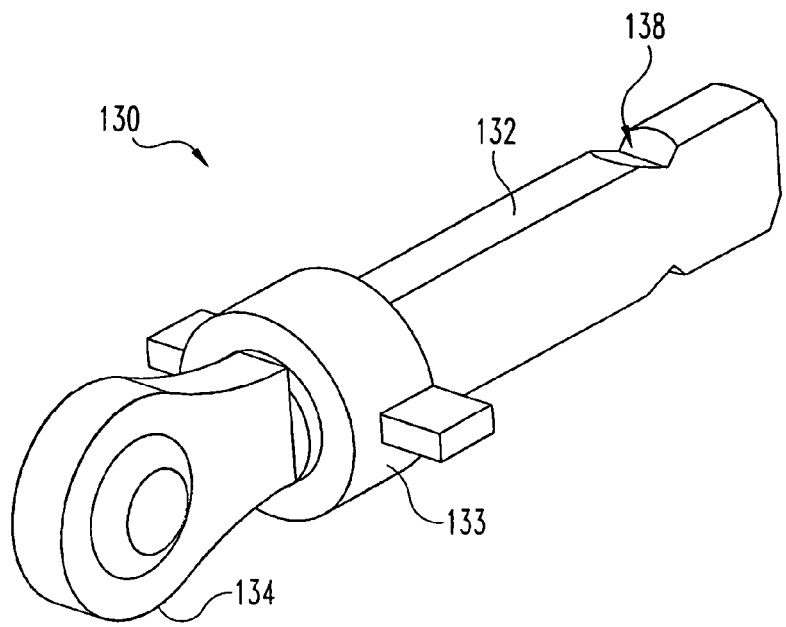
FIG. 10 is a perspective view of a lancing device according to a further embodiment of the present invention.
Figure 11:
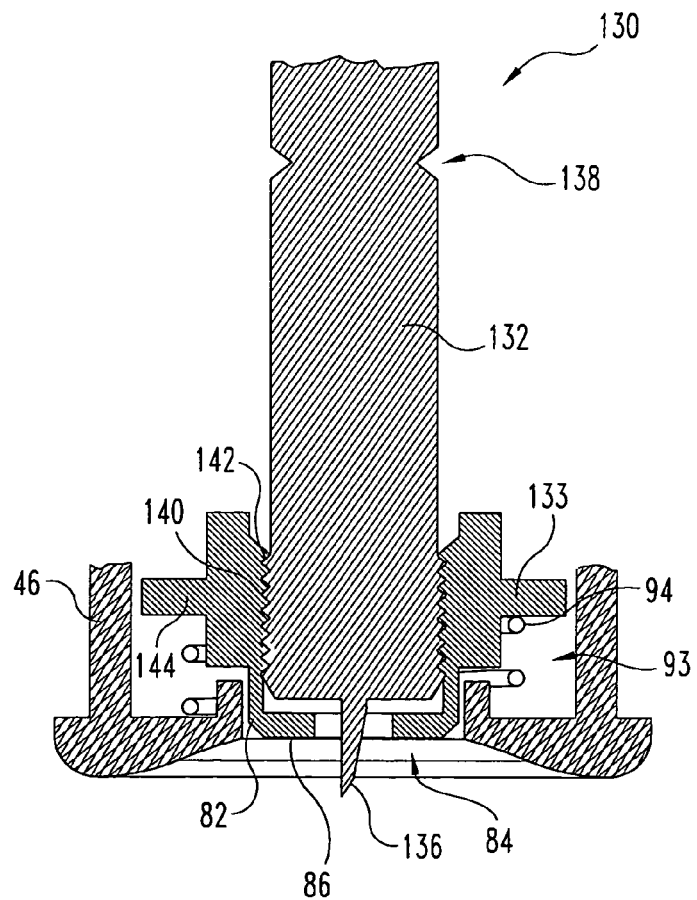
FIG. 11 is a cross-sectional view of the FIG. 10 device.
Figure 12:
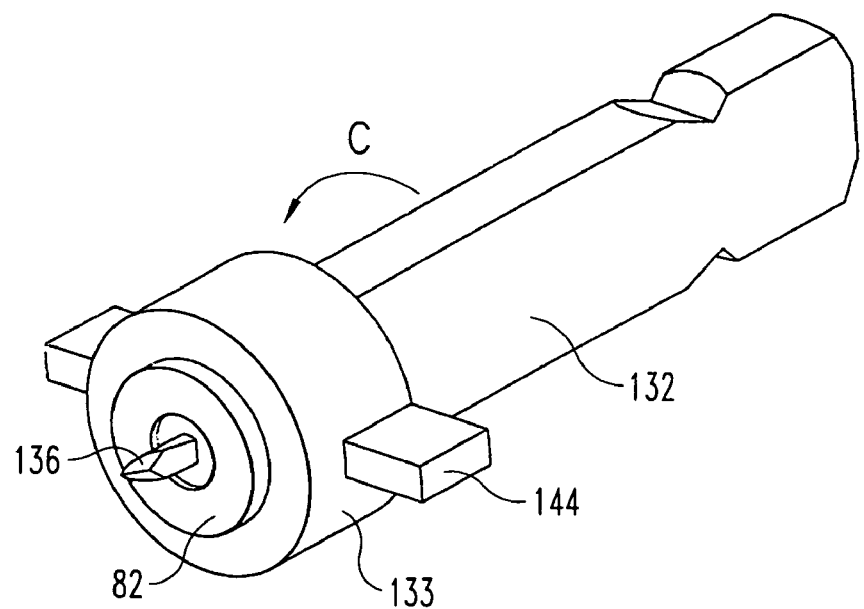
FIG. 12 is a perspective view of the FIG. 10 device configured for a deep penetration depth.
Figure 13:
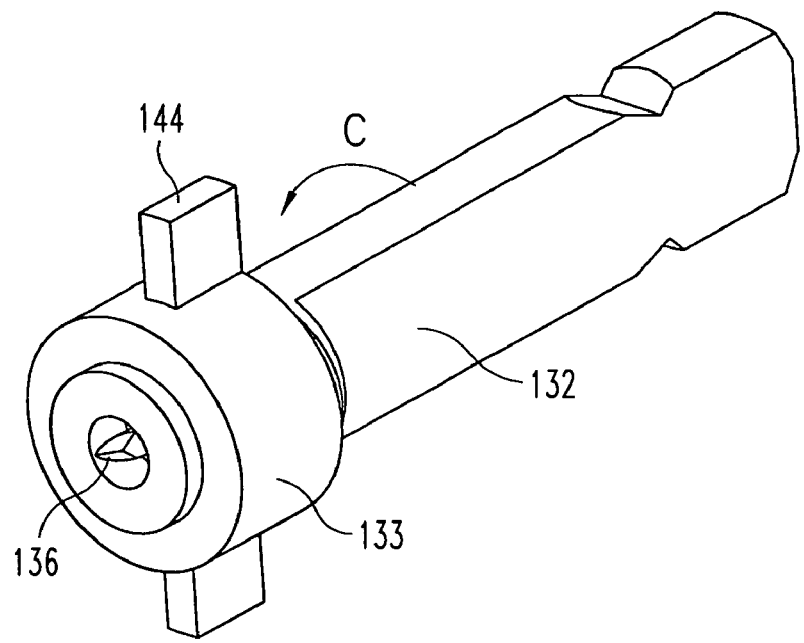
FIG. 13 is a perspective view of the FIG. 10 device configured for a shallow penetration depth.

An incision forming member 130 according to another embodiment of the present invention will now be described with reference to FIGS. 10-13. As illustrated in FIGS. 10 and 11, the incision forming member 130 includes a body portion 132, a reference member 133, a safety cover 134 and a lancet 136. In one embodiment, the body portion 132, the reference member 133 and the safety cover 134 are made of plastic; while lancet 136 is made of metal. As should be appreciated, these components can be made of other materials. The body portion 132 has a pair of opposing notches 138 that are used secure the incision forming member 130 to the bodily fluid sampling device. To protect the user from being accidentally cut by the lancet 136, the safety cover 134 covers the lancet 136 before use. In addition, the safety cover 134 can be used to ensure the sterility of the lancet 136. When the incision forming member 130 needs to be used, the safety cover 134 can then be removed from the lancet 136, as illustrated in FIGS. 11-13. In one form of the present invention, the safety cover 134 is integrally molded with the body portion 132 such that the safety cover 134 can be removed by twisting the cover 134 off the body portion 132. In another form, the safety cover 134 is separate from the body portion 132. Like the previous embodiments, the lancet 136 in FIG. 11 is configured to form an incision in the skin. By way of nonlimiting example, the lancet 136 can be a blade, a needle or the like.

In the embodiment illustrated in FIG. 11, the reference member 133 is attached to the body 132 of the incision forming member 130 in order to control the penetration depth of the lancet 136. As shown, the incision forming member 130 is received inside the expression member 46. The retraction mechanism 93 used in the illustrated embodiment is spring 94, which is engaged between the expression member 46 and the reference member 133. The reference member 133 has contact portion 82 with skin contacting surface 86 that controls the penetration depth of the lancet 136. After the incision is formed, the incision forming member 130 along with the reference member 133 are retracted by spring 94 such that the contact portion 82 is removed from the expression opening 84 in the expression member 46. By retracting the contact portion 82 of the reference member 133, the larger expression opening 84 can be used to express bodily fluid. It is contemplated, however, that the reference member 133 can be retracted in other manners. For instance, incision forming member 130 can be incorporated into a SOFTCLIX brand lancing device that can be used to actuate and retract the incision forming member 130. To adjust the penetration depth of the lancet 136, the reference member 133 and the body portion 132 are threadedly mated together. For example, the reference member 133 and the body portion 132 can be threadedly mated during the molding process for the parts. As shown in FIG. 11, the reference member 140 has an internally threaded portion 140 that engages an externally threaded portion 142 on the body portion 132 of the incision forming member 130. Further, the reference member 133 has one or more wing members 144 extending therefrom that engage spring 94 and are used to help turn the reference member 133 relative to the body portion 132. For instance, as shown in FIGS. 12 and 13, the penetration depth of the lancet 136 can be reduced by rotating the reference member 133 in a counterclockwise direction C. It should be appreciated that the incision forming member 130 can be threaded differently such that the penetration depth is increased by rotating the reference member 133 in the counterclockwise direction C.

Figure 14:
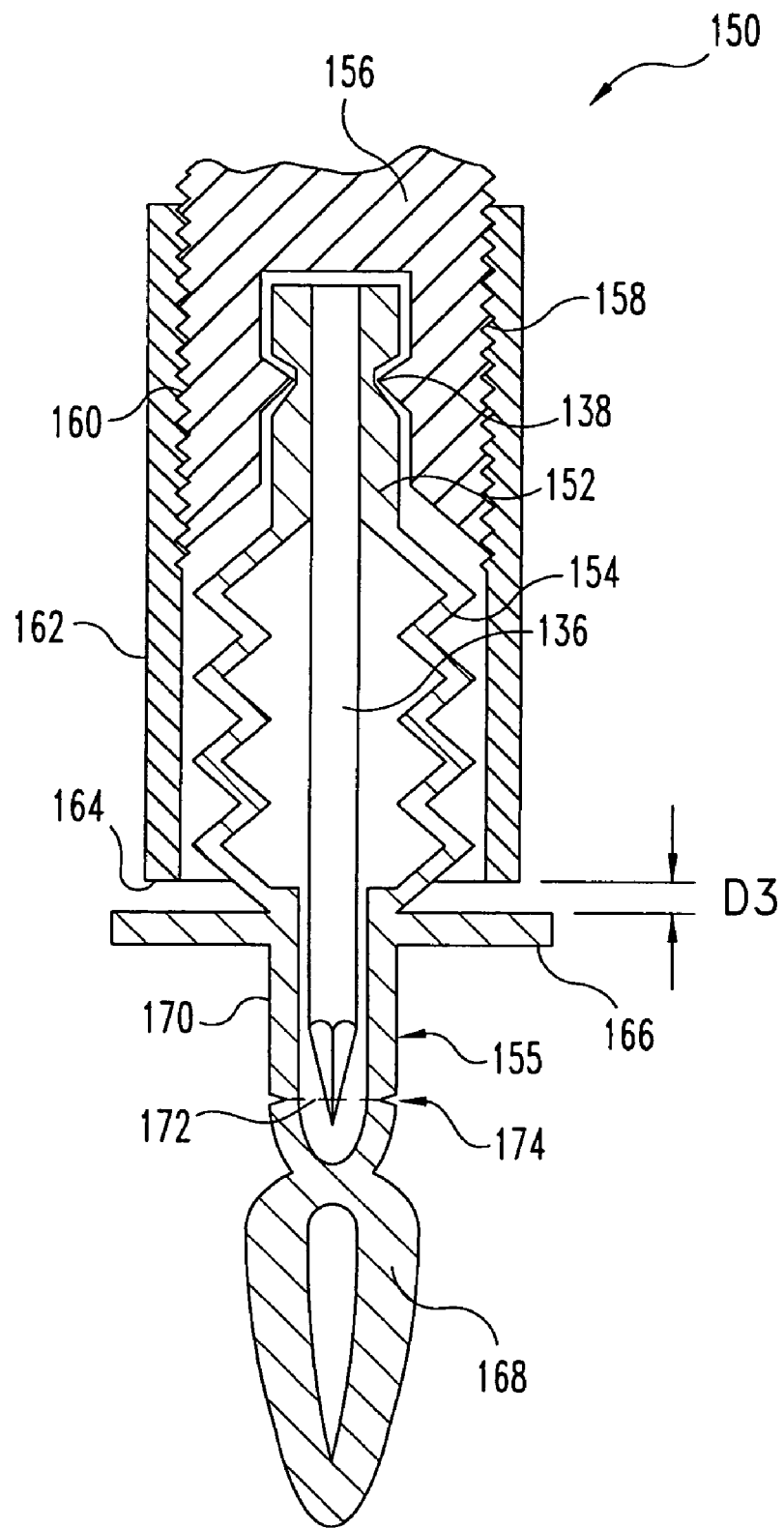
FIG. 14 is a cross-sectional view of a lancing device according to another embodiment.

An incision forming member assembly 150 according to another embodiment of the present invention is illustrated in FIG. 14. As shown, the assembly 150 includes a body 152 and lancet 136 attached to the body 152. In the body 152, living hinges 154 (or other spring means) resiliently attach a reference member portion 155 to the remainder of the body 152. Notches 138 are defined in the body 152 to secure the body to a holder 156. In the illustrated embodiment, the holder has external threads 158 that mate with internal threads 160 on depth control member 162. The depth control member 162 has a contact edge 164 configured to contact a stop flange 166 on the reference member portion 155. Distance D3 between edge 164 and stop flange 166 controls the penetration depth of the lancet 136. Assembly 150 further includes a safety cover 168 that covers the lancet 136 in order to protect the user and provide a sterile environment for the lancet 136. In the reference member portion 155, a skin contact portion 170 extends from the stop flange 166 along the lancet 136. Between the skin contact portion 170 and the safety cover 168, a groove or an area of weakness 172 is formed so that the cover 168 can be detached from the skin contact portion 170 to expose the lancet 136. Once the cover 168 is detached, a skin contacting surface 174 is formed at groove 172.

Assembly 150 is used in conjunction with an expression member 46 of the type described above. As previously mentioned, variations in skin height due to factors, such as the pressure applied to the skin, the type of skin and the skin location, can significantly alter the penetration depth of traditional lancing devices. Assembly 150 is constructed to contact the skin before lancing will occur, which in turn provides a reference surface for controlling the penetration depth into the skin. During lancing, the skin contact portion 155 extends through the expression opening 84 in the expression member 46, and the skin contacting surface 174 of assembly 150 contacts the skin. As the skin contacting surface 174 is pressed against the skin by the actuation of the lancet assembly 150, the living hinges 154 are compressed until the stop edge 164 contacts flange 166. As previously mentioned, the distance D3 between edge 164 and flange 166 controls the penetration depth of the lancet 136. Increasing distance D3 by rotating the depth control member 162 relative to holder 156 deepens the penetration depth of the lancet 136. In contrast, reducing the distance D3 between edge 164 and flange 166 decreases the penetration depth of the lancet 136. The living hinges 154 aid in retracting the lancet 136 from the incision. When assembly 150 is retracted after lancing the skin, the contact portion 155 is removed from the expression opening 84 of the expression member 46, thereby providing a wider opening in which the bodily fluid can be expressed.

A lancing assembly 180 according to a further embodiment of the present invention will now be described with reference to FIGS. 15-17. Lancing assembly 180 integrates a number of features into a single device; while at the same time allows for sterilization of the lancet without affecting the test strip. Assembly 180 includes an incision forming member 182, test media 184, and a carrier 186. As shown, the incision forming member 182, which is used to form an incision in the skin, has a head 188, a lancet 190, a pry member 192, and a safety cover 194. The head 188 and the cover 194 are positioned at opposite ends of the lancet 190, and the pry member 192 is positioned along the lancet 190, between the head 188 and the cover 194. In the illustrated embodiment, the head 188 has a pair of lock notches 196 for locking the incision forming member 182 in an armed position. The lancet 190 in the illustrated embodiment is a needle. However, it should be appreciated that lancet 190 can include other types of instruments that are used to from incision, such as blades for example. The pry member 192 has a pair of pry surfaces 198 that are angled towards the lancet 190. To make insertion of the incision forming member 182 into the carrier easier, surfaces 198 are rounded. One of the many functions of the safety cover 194 includes covering tip 200 of the lancet 190 (see FIG. 17) in order to maintain the sterility of the lancet 190. Moreover, the cover 194 protects users from accidentally cutting themselves. As illustrated, the cover 194 in the illustrated embodiment has a general cylindrical shape with an alignment flange 202 extending therefrom at one end. The cover 194 further has an opening 204 that is normally sealed so as to maintain the sterility of the lancet tip 200. In one form, the head 188 and the pry member 192 are made from a hard plastic; the cover 194 is made of a soft plastic; and the lancet 190 is metallic. As should be appreciated, these components can be made from other types of materials.

The test media 184 is used for determining analyte levels in the bodily fluid sample. As should be appreciated, analyte levels can be determined through the chemical, electrical, electrochemical and/or optical properties of the bodily fluid sample collected on the test media, to name a few. For example, the test media 184 in the illustrated embodiment is a chemically reactive reagent test strip. Typically, reagent test strips are sensitive to thermal and/or chemical processes required for sterilization. The sterilization process can affect the results generated by the test media 184, and therefore, recalibration of the test media 184 is required after sterilization. In the embodiment illustrated in FIGS. 15-17, the incision forming member 182 can be separately sterilized such that the test media 184 does not have to go through the same sterilization process as the incision forming member 182. After sterilization, the incision forming member 182 can be installed in the carrier 186, thereby eliminating the need to recalibrate the test media 184.

Figure 15:
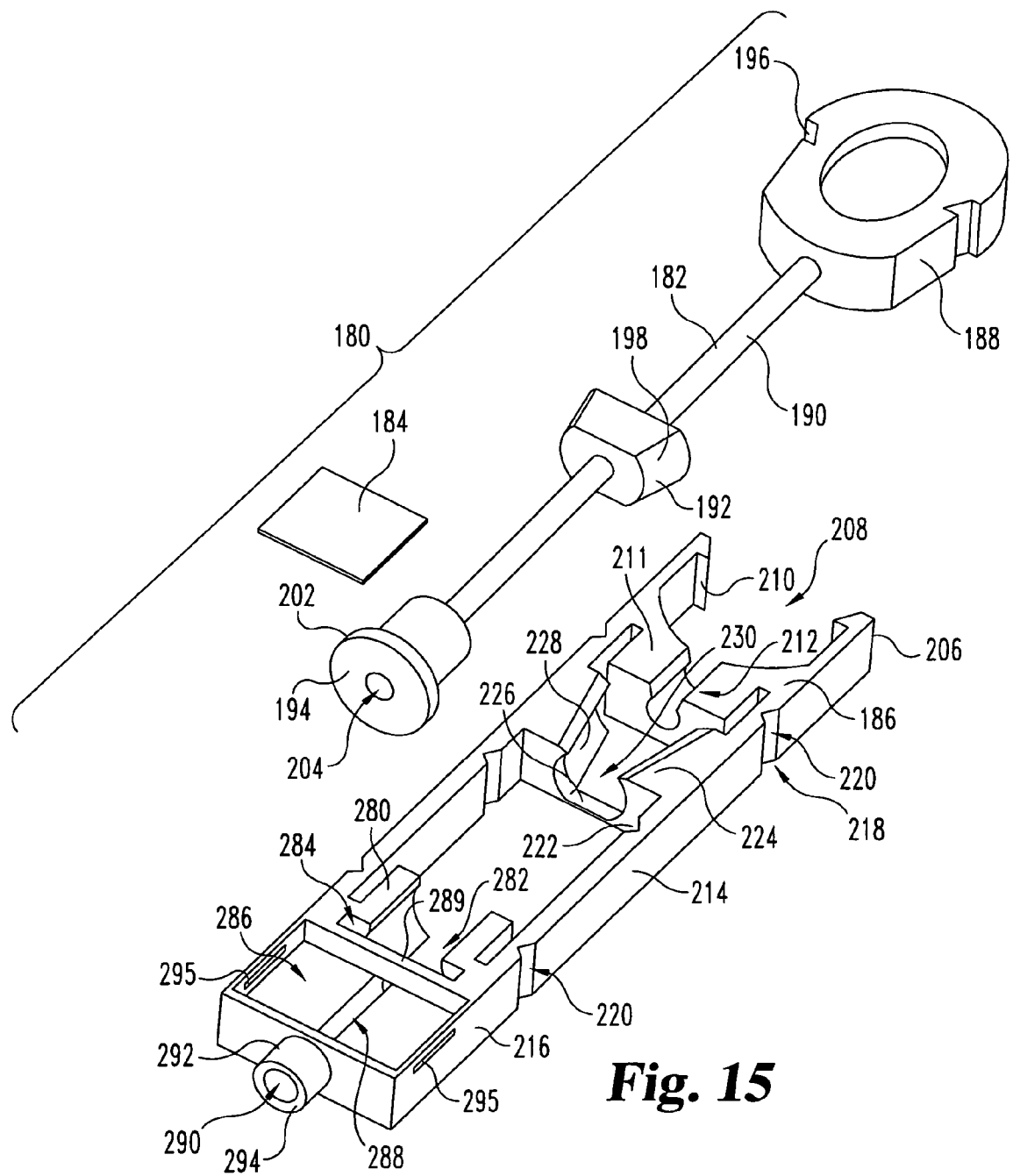
FIG. 15 is an exploded view of a sampling device according to a further embodiment.
Figure 16:
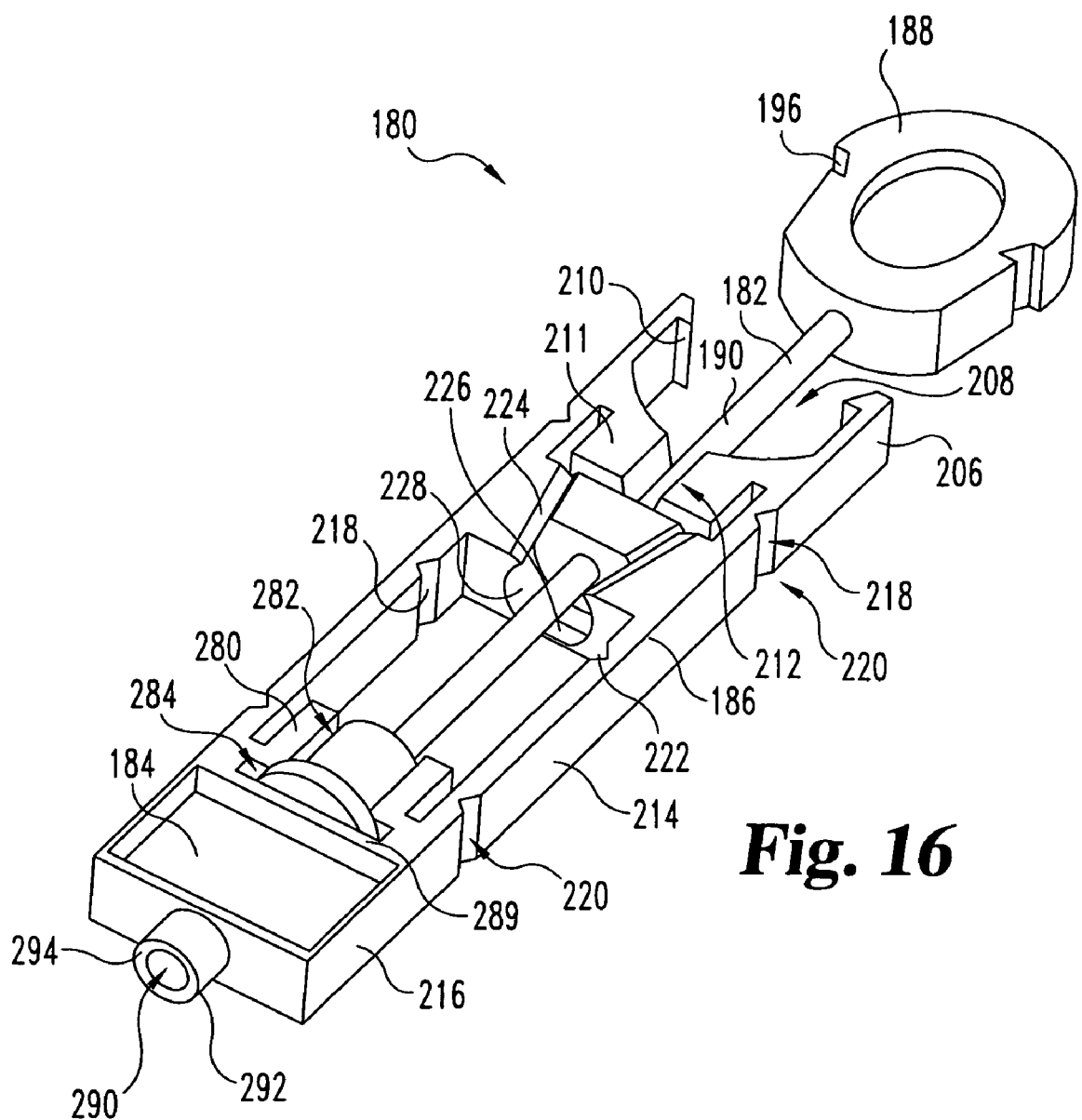
FIG. 16 is a perspective view of the FIG. 15 device.
Figure 17:
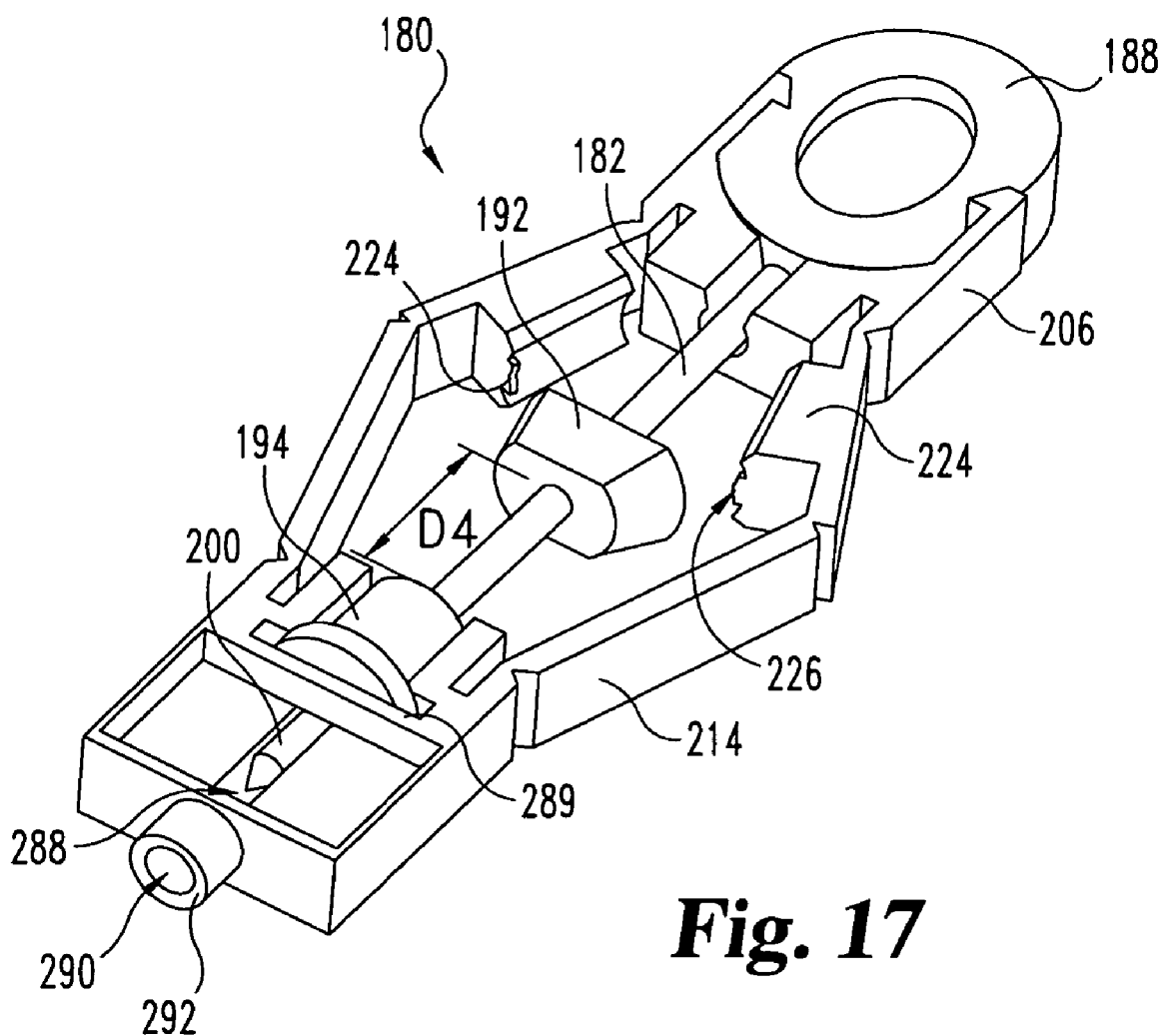
FIG. 17 is a perspective view of the FIG. 16 in an armed configuration.

Referring to FIGS. 15 and 16, the carrier 186 has a pair of lock arms 206 that define a receptacle 208 in which the head 188 is locked when the lancet 182 is in the armed position, as is shown in FIG. 17. Each lock arm 206 has a lock tab 210 that is constructed to engage a corresponding notch 196 in the head 188. Between the lock arms 206, the carrier has a connector 211 with a slot 212 in which the lancet 190 is slidably received. The carrier 186 further includes a pair of living hinges 214 that connect the lock arms 206 to sampling portion 216 of the lancing assembly 180. As shown, the living hinges 214 have notches 218 that allow the living hinges 214 to bend. Each of the living hinges has two outwardly opening notches 220 that are located proximal the connector 211 and the sampling portion 216. Between the outwardly opening notches 220, each living hinge 214 has an inwardly opening notch 222. The living hinges 214 have expansion members 224 that are connected together by a tamper evidence link 226. Each expansion member has a pry surface 228, and the pry surfaces 228 are constructed to define a pry member cavity 230 that receives the pry member 192 of the incision forming member 182. In the illustrated embodiment, the pry surfaces 228 are angled and are concavely shaped to coincide with the shape of the surfaces 198 on the pry member 192. The carrier 186 further includes a cover receptacle 280 that defines a safety cover cavity 282 in which the safety cover 194 of the incision forming member 182 is received. As illustrated in FIG. 15, cavity 282 includes an alignment slot 284 that is configured to receive the alignment flange 202 of the safety cover 194.

As shown in FIG. 15, the sampling portion 216 of the carrier 186 defines a test media cavity 286 in which the test media 184 is housed during use. Inside the test media cavity 286, the sampling portion 216 further has a capillary channel 288. The capillary channel 288 is configured to allow the lancet 182 to extend therethrough during lancing and is configured to draw fluid onto the test media 184 during sampling. In cavity 286, the test media 184 is slightly spaced away from the sampling portion 216 in order to define a flat capillary space for spreading the fluid sample across the test media 184. As depicted, a cross member 289 extends across a portion of the channel 288 proximal the cover 194 so as to prevent removal of the incision forming member 182 when the assembly 180 is armed. The channel 288 fluidly communicates with an aperture 290 defined in skin contacting portion 292. The skin contacting portion 292 has a skin contacting surface 294 that contacts and flattens the skin around the aperture 290 so that the lancet 182 can cut an incision with a precise depth.

To arm the assembly 180, the head 188 is pushed into the receptacle 208 such that the lock arms 206 engage and lock with the notches 196 in the head 188, as is illustrated in FIG. 17. During arming, the pry member 192 breaks the tamper evidence link 226 by prying the expansion members 224 apart, which in turn bends the living hinges 214. As mentioned above, the tamper evidence link 226 provides a visual indicator of prior arming or use of the device 180. When assembly 180 is armed, the tip 200 of the lancet 182 pierces through the sealed opening 204 in the cover 194 and extends into the capillary channel 288. By extending across the capillary channel 288, the cross member 289 helps to prevent accidental removal of the incision forming member 182 after arming. It should be noted that that the test media 184 is not shown in FIG. 17 so that the tip 200 of the lancet 182 can be viewed when in the armed position and that the test media 184 is typically attached before arming in the illustrated embodiment. Moreover, it should be noted that the tip 200 of the lancet 182 in one form is typically positioned within aperture 290 proximal the skin contacting surface 294.

After arming, assembly 180 can be used to form an incision in the skin. To form the incision, the assembly 180 is installed in a sampling device in one embodiment of the present invention. In one form, the assembly 180 is armed by the sampling device, and in another form, the assembly is armed before installation in the sampling device. During lancing, the skin contacting surface 292 contacts the skin, and the tip 200 of the lancet 190 is driven through opening 290. In one embodiment, the incision forming member 182 is actuated by a hammer, or a similar device, in order to strike the head 188 of the incision forming member 182. In one embodiment, the penetration depth of the lancet 190 is controlled by an adjustable holder for assembly 180 of the type similar to the one described below with reference to FIG. 22. In another embodiment, distance D4 between the pry member 192 and the cover 194 controls the penetration depth of the lancet 190. As the incision forming member 182 is driven, the living hinges 214 are compressed. After the tip 200 of the lancet 190 is fully extended, the compressed living hinges 214 recoil, thereby retracting the lancet 190. The bodily fluid from the incision formed by the lancet 190 is collected through aperture 290 and is distributed across the test media 184 via capillary channel 184. The annular space defined in aperture 290 between the lancet 190 and the skin contacting portion 292 forms a low volume capillary for transporting the fluid. The fluid is then transferred to the flat capillary defined between the test media 184 and the sampling portion 216 in cavity 286. In one form, the gaps are small (0.1 mm or less) to promote transfer of the fluid between the annular and flat capillaries. In one embodiment, venting of the capillaries is accomplished via slots or channels 295 formed around cavity 286.

Figure 19:
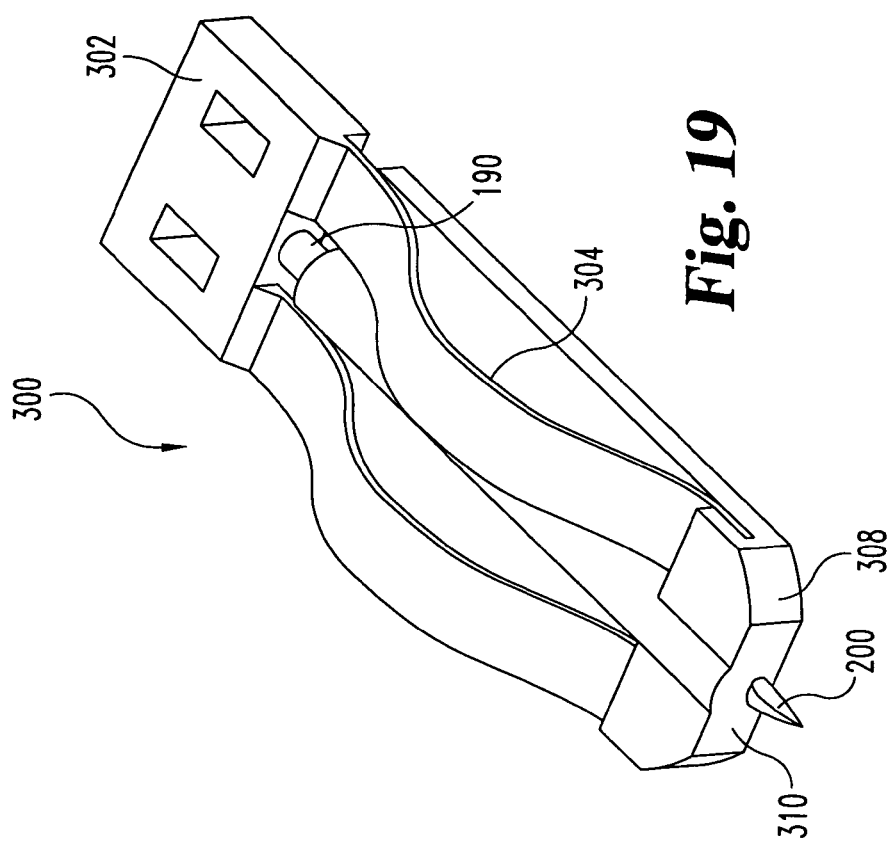
FIG. 19 is a top perspective view of the FIG. 18 device in a lancing position.
Figure 18:
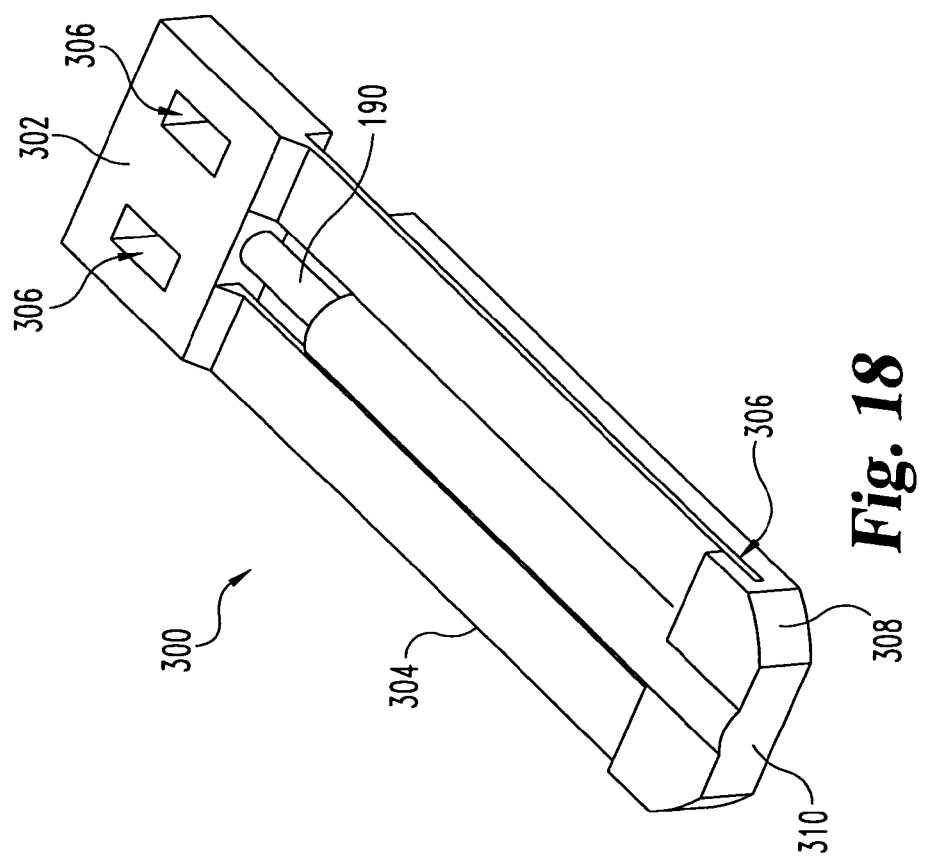
FIG. 18 is a perspective view of a sampling device according to another embodiment.

A sampling device 300 according to another embodiment of the present invention is illustrated in FIGS. 18-20. FIG. 18 depicts the device 300 prior to lancing; while FIGS. 19 and 20 show the device 300 during lancing. Sampling device 300 includes a head member 302 that has a pair of living hinges or leaf springs 304. The head 302 defines a pair of openings 306 that are used to secure the device 300. As shown, the ends of the leaf springs 306 that are opposite the head 302 are received in slots 306 defined in safety cover 308. The safety cover 308 encapsulates lancet 190 to protect the lancet 190 from outside contamination. In the illustrated embodiment, the lancet 190 is attached to the head 302, and in another embodiment, the lancet 190 abuts the head 302. The cover 308 has an encapsulating surface 310 that covers the lancet 190. Before lancing, as depicted in FIG. 18, the encapsulating surface 310 of the safety cover 308 covers the lancet 190. During lancing, as illustrated in FIG. 19, the tip 200 of the lancet 190 pierces the encapsulating surface 310 of the cover 308. In one embodiment, the encapsulating surface 310 includes soft foam and/or rubber that surround the tip 200 of the lancet 190 inside the cover 308. Following lancing of the skin, the leaf springs 304, which were bent during lancing, retract the lancet 190 from the skin.

Like the device shown in FIGS. 15-17, the sampling device 300 illustrated in FIGS. 18-20 allows test media 312 to be assembled to the remainder of the device after the lancet 190 has been sterilized. As illustrated in FIG. 20, the test media 312 is attached to the safety cover 308, and the test media 312 has an overhang portion 313 that extends past surface 310 on the cover 308. In one embodiment, the test media 312 is glued to the covers. As should be appreciated, the test media 312 can be attached in other manners. In the illustrated embodiment, the test media 312 is operable to test analyte levels electrochemically. In another embodiment, the test media 312 is operable to test analyte levels optically. It should be understood that the test media 312 can test analyte levels using other techniques. Proximal to surface 310, the test media 312 incorporates a capillary portion 314 for drawing bodily fluid into the test media 312 for testing. The overhang portion 313 of the test media 312 ensures that capillary 314 is in close proximity to the skin. The capillary portion 314 is surrounded by a skin contacting surface 315 that acts as the reference surface for controlling the penetration depth of the lancet 190. In FIG. 20, the head 302 and the safety cover 308 have opposing stop surfaces 316 and 318 that control the penetration depth of the lancet 190. In one embodiment, the distance between stop surfaces 316 and 318 determines the penetration depth of the lancet 190. In another embodiment, spacers with varying thicknesses are placed between the stop surfaces 316 and 318 to adjust the penetration depth of the lancet 190.

Figure 22:
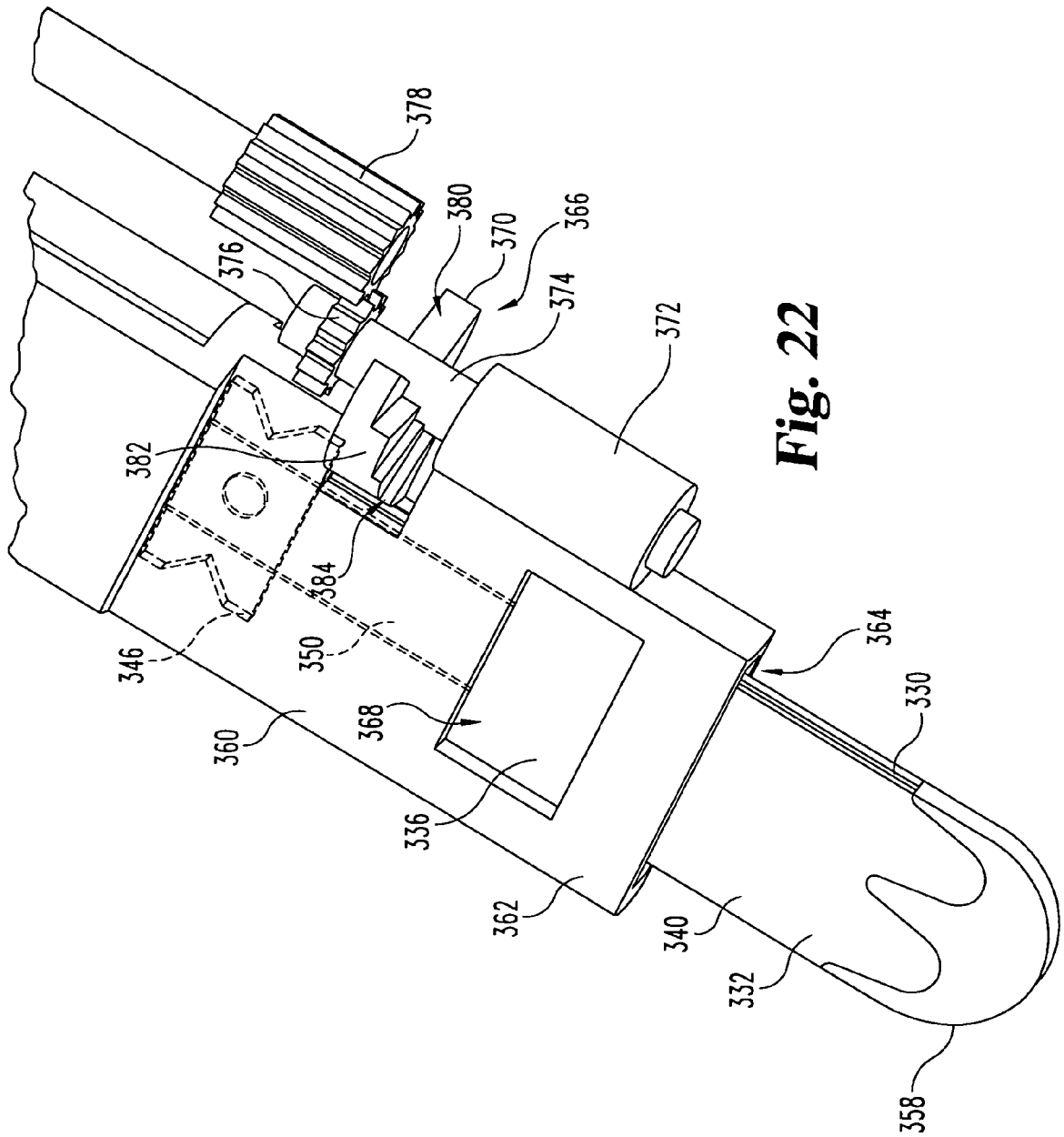
FIG. 22 is a perspective view of an adjustable holder according to another embodiment holding the FIG. 21A device.
Figure 23:
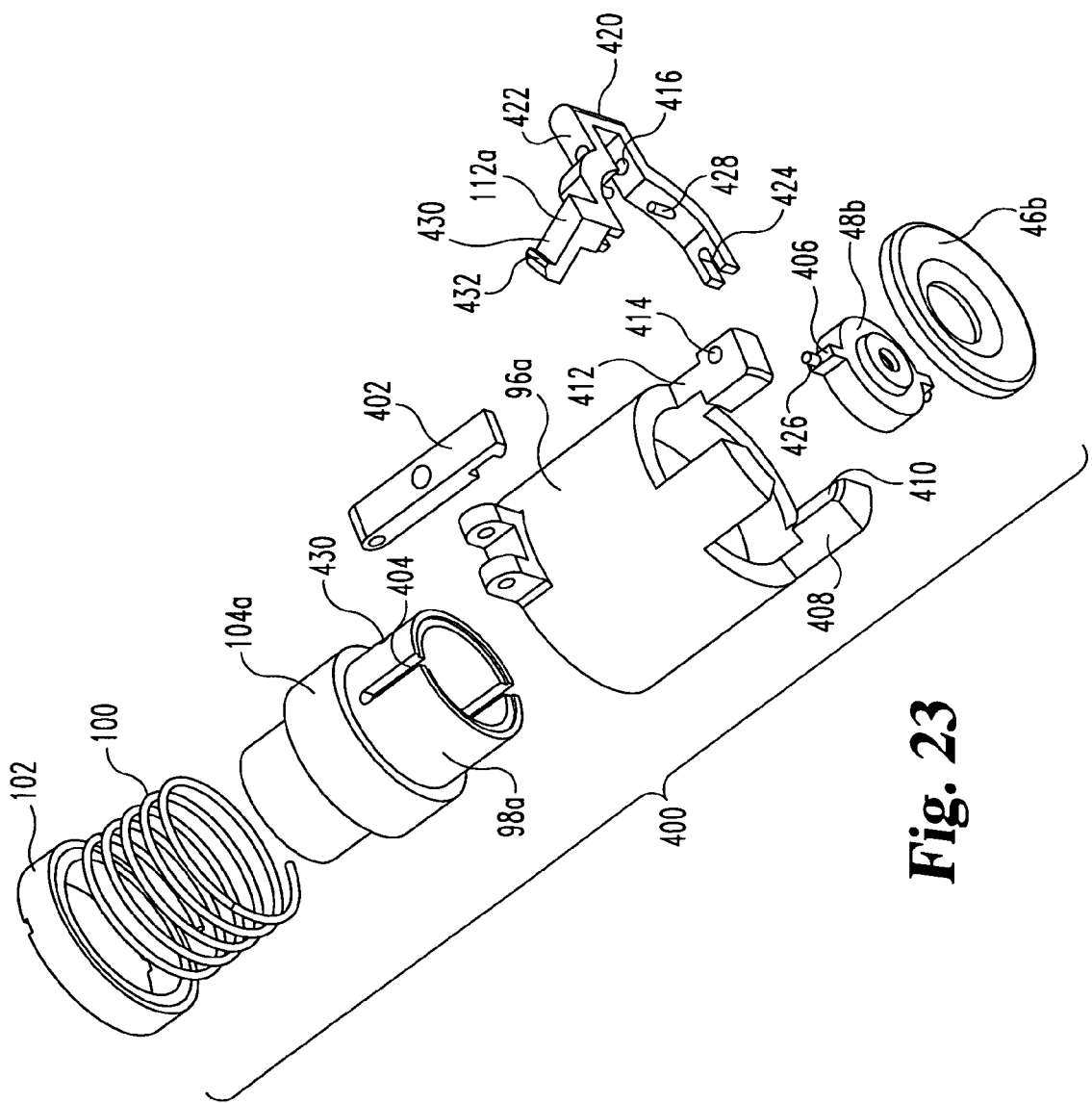
FIG. 23 is an exploded view of a sampling device according to another embodiment.

FIGS. 21-22 illustrate a sampling device 330 according to another embodiment of the present invention. As shown in FIGS. 21A-B and 22, device 330 includes a housing 332, a lancet or blade 334 slidably received in the housing 332, and test media 336. Housing 332 has first 338 and second 340 sides that are attached together through a bead 342 to form a blade cavity 344 in which blade 334 is received. In the illustrated embodiment, both the first 338 and second 340 sides are generally flat to give the sampling device an overall flat appearance. In one form, bead 342 is an adhesive bead that adheres the first 338 and second 340 sides together. Conceptually, the housing 332 can be further subdivided into separate head 346 and skin contacting 348 portions. Blade 334 is attached to the head 346 and is slidable within blade cavity 344 in the skin contacting portion 348 of the housing 332. The first side 338 of the housing 332 defines a living hinge or leaf spring 350 that connects the head 346 to the skin contacting portion 348 of the housing 332. The head 346 can further have notches 352 for securing device 330 to a holder. FIGS. 21 and 22 illustrate the leaf spring 350 in a flexed state when blade 334 is extended from the housing 332 through opening 353. Next to opening 353, the first side 338 of the housing 332 has a skin contacting edge 354 that acts as a reference surface for controlling the penetration depth of the blade 334. Opposite the edge 354, the second side 340 of the housing 332 has a capillary slot 356 for drawing fluid via capillary action into the blade cavity 344. As shown, the capillary slot 356 in the illustrated embodiment has a gradual tapered shaped from opening 353 to improve fluid flow from the incision into the blade cavity 344. As shown in FIG. 23, capillary slot 356 as well as opening 353 can be covered with a safety cover 358 that can be used to maintain the sterility of blade 334 and to protect the user from injury.

In the blade cavity 344, especially between the blade 334 and the second side 340 of the housing 332, a gap is formed around the blade 334 for drawing bodily fluid from the incision to the test media 336 via capillary action. In one embodiment, the side of the blade 334 that faces the test media 336 is coated and/or incorporates hydrophilic material, and the opposite side is coated and/or incorporates hydrophobic material. As should be appreciated, this construction improves the transfer of the fluid onto the test media 336. The test media 336 can be of the type described above and can be attached to the housing 332 in a number of manners. For instance, the test media 336 can be a chemically reactive reagent strip that is glued to the housing. To ensure proper calibration of the test media 336, the test media 336 can be attached to the housing 332 after the blade 334 has been sterilized. Once attached, the test media 334 defines portion of the blade cavity 344 and fluid from slot 356 can be drawn to the test media 332 through the blade cavity 334.

A holder 360 for device 330 that is operable to adjust the penetration depth of the blade 334 is illustrated in FIG. 22. Holder 360 has a cover 362 with a receptacle 364 in which device 330 is received and a depth control mechanism 366 that is coupled to the cover 362. In the illustrated embodiment, a test media view window 368 is defined in the cover 362 so that the test media 336 can be viewed. Window 368 can allow the test media 336 to be analyzed optically. The depth control mechanism 366 has a depth adjustment wheel 370 that is rotatably coupled to a bearing member 372 through rod 374, and the bearing member 372 is attached to the cover 362. The rod 374 has a gear 376 that is engageable with an actuation gear 378. Wheel 380 only partially extends around rod 374, thereby defining a gap 380 that allows device 330 to be mounted in holder 360. As shown, the wheel 380 has a series of steps 382 of graduated thickness, and the steps 382 of wheel 380 can be rotated through a slot 384 in the cover 362.

To insert device 330 into holder 360, the actuation gear 378 rotates the wheel 380 such that gap 380 is positioned in the slot 384. Device 330 is then slid into the receptacle 364 so that the head 346 of the device 330 is slid past slot 384. Next, the actuation gear 378 rotates the wheel 380 such that at least one of the steps 382 is positioned in the slot 384 between the head 346 and the skin contacting portion 348, thereby securing the device 330 to the holder 360. The step 382 with the appropriate thickness can be positioned in the slot 384 between the head 346 and the skin contacting portion 348 so as to control the penetration depth of the blade 334. During lancing, as the holder 360 is driven towards the skin, the skin contacting edge 354 contacts the surface of the skin. As the holder 360 is driven further, the skin contacting portion 348 of the housing 332 slides within the receptacle 364 towards the head 346 of the device 330 such that the blade 334 is uncovered to lance the skin. The skin contacting portion 348 of the housing 332 continues to retract until it engages the selected step 382 on the wheel 380. As previously mentioned, the thickness of the step 382 controls the penetration depth of the blade 334. Afterwards, the leaf spring 350, which became flexed during lancing, extends portion 348 of the housing 332 so as to recover the blade 334. Once the incision is formed, the skin contacting edge 354 can remain positioned against the skin (or positioned proximal to the skin) such that the fluid from the incision is drawn via capillary action into the blade cavity 344. In one embodiment, the fluid is drawn onto the side of the blade that faces the test strip 336, which is coated with hydrophilic material. From the blade cavity 344, the fluid is then deposited onto the test strip 336 for testing.

A lancing device 400 according to a further embodiment, which incorporates components similar to the embodiments illustrated in FIGS. 1-9, will now be described with reference to FIGS. 23-28. Lancing device 400 according to the illustrated embodiment is configured to automatically increase the size of the expression opening and maintain the larger sized expression opening when fluid is expressed from an alternate site. As depicted in FIG. 23, the lancing device 400 includes an outer expression member or tip 46b, a reference member 48b, a cam arm 112a, a sleeve 96a, a latch mechanism 402, a housing 98a, spring 100 and nut 102. Similar to the embodiments illustrated in FIGS. 1-9, the reference member 48b has skin contacting portion 82 with skin contacting surface 86 that surrounds aperture 88 (see FIG. 27). The expression tip 46b in FIG. 28 has an expression surface 92, which has a conical form, and the expression surface 92 surrounds expression opening 84. The expression tip 46b is attached to the sleeve 98a, which is slidably received in the housing 98a. In one form of this embodiment, the expression tip 46b is glued to the sleeve 98a. However, it is contemplated that the expression tip 46b can be secured in other manners.

Figure 24:
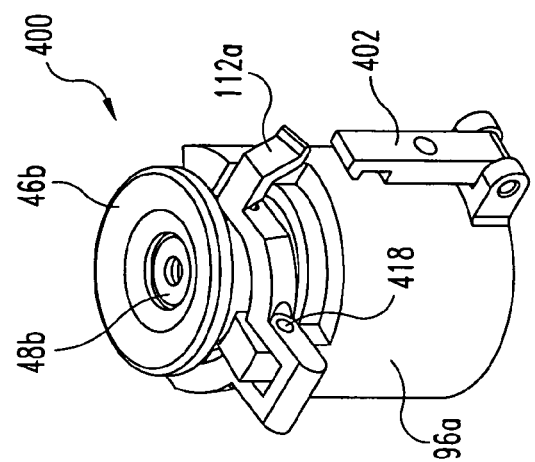
FIG. 24 is a perspective view of the FIG. 23 device.

As depicted in FIG. 23, the sleeve 98a defines a pair guide slots 404 that are configured to receive a pair of guide bosses 406 on the reference member 48b. It should be appreciated that the reference member 48b can have more or less guide bosses 406 than is shown. In the illustrated embodiment, the guide bosses 406 have a generally rectangular shape so as to align the reference member 48b in the guide slots 404. Around the sleeve 98a, the housing 96a has stop arms 408 with stop members 410 that are adapted to engage a stop flange 104a on the sleeve 98a. In the illustrated embodiment, the penetration depth of the lancet 50 is controlled by the mechanism that is used actuate the lancet 50, such as in a SOFTCLIX brand lancing device. It is contemplated, however, that the penetration depth of the lancet 50 can be controlled in other manners. For instance, the distance between the stop flange 104a and the stop members 410 can be used to control the penetration depth of the lancet 50. On one of the stops 408, arm 412, the cam arm 112a is pivotally mounted. Both arm 412 and cam arm 112a have pivot pin openings 414 and 416 in which a pivot pin 418 is received, as is shown in FIGS. 23-24. The cam arm 112a has a link portion 420 that join two actuation members 422 that give the cam arm 112a a general u-shape. The end of each actuation member 422, opposite link 420, has a reference member engaging slot 424 that are configured to engage cam arm pins 426 that extend from the guide bosses 406 on the reference member 48b. In the illustrated embodiment, the actuation members 422 have a generally bowed shape so as to fit around the sleeve 98a. Between pivot pin openings 416 and slots 424, each actuation member 422 has a sleeve engaging pin 428 that are received in a corresponding pivot pin opening 430 in the sleeve 98a. On the cam arm 112a, a lock arm portion 430 with a lock tab 432 extends from one of the actuation members 422. Referring to FIGS. 25 and 26, one end of the latch arm 402 is pivotally mounted to the housing 96a, and the other end of the latch arm 402 has a latch notch 434 configured to engage the lock tab 432. In the illustrated embodiment, gravity is used to position the latch arm 402 such that the latch arm is able to engage the lock tab 432. In another embodiment, the latch arm 402 incorporates a spring for biasing the latch arm 402 toward the housing 96a such that the latch arm 402 is able to engage the lock tab 432 on the cam arm 112a. It should be appreciated that latch arm 402 can be biased in other manners.

By being able to accurately control the penetration depth of the lancet 50, the device 400 is able to safely lance and express fluid from both fingertips and alternate sites. As previously discussed, the actuation mechanism for the lancet 50 controls the penetration depth of the lancet 50. With reference to FIGS. 27-28, spring 100 is secured between the stop flange 104a of the sleeve 98a and the nut 102, which is secured to the housing 96a. Normally, as shown in FIG. 27, the spring 100 biases the sleeve 98a with respect to the housing 96a such that the cam arm 112a positions the reference member 48b in expression opening 84 of the expression tip 46b so that the penetration depth can be precisely controlled during lancing. Typically, device 400 is only used to lance the fingertip and is not used to express fluid from the fingertip because fingertips tend to provide an adequate fluid supply without the need to express the fluid. When expressing from an alternate site, as depicted in FIG. 28, the user grips and presses the housing 96a towards the skin. As the housing 96a slides relative to the sleeve 98a, the cam arm 112a pivots such that the reference member 48b is retracted from the expression opening 84. The retraction of the reference member 48b creates a large opening in which bodily fluid from an alternate site can be expressed. To ensure that the reference member 48b remains in the retracted position during expression of fluid from an alternate site, the lock tab 432 on the cam arm 112a locks with the latch arm 402. After the fluid has been expressed, the latch arm 402 can be disengaged from the lock tab 432 to return the device 400 to its original configuration, as illustrated in FIG. 27.

Figure 29:
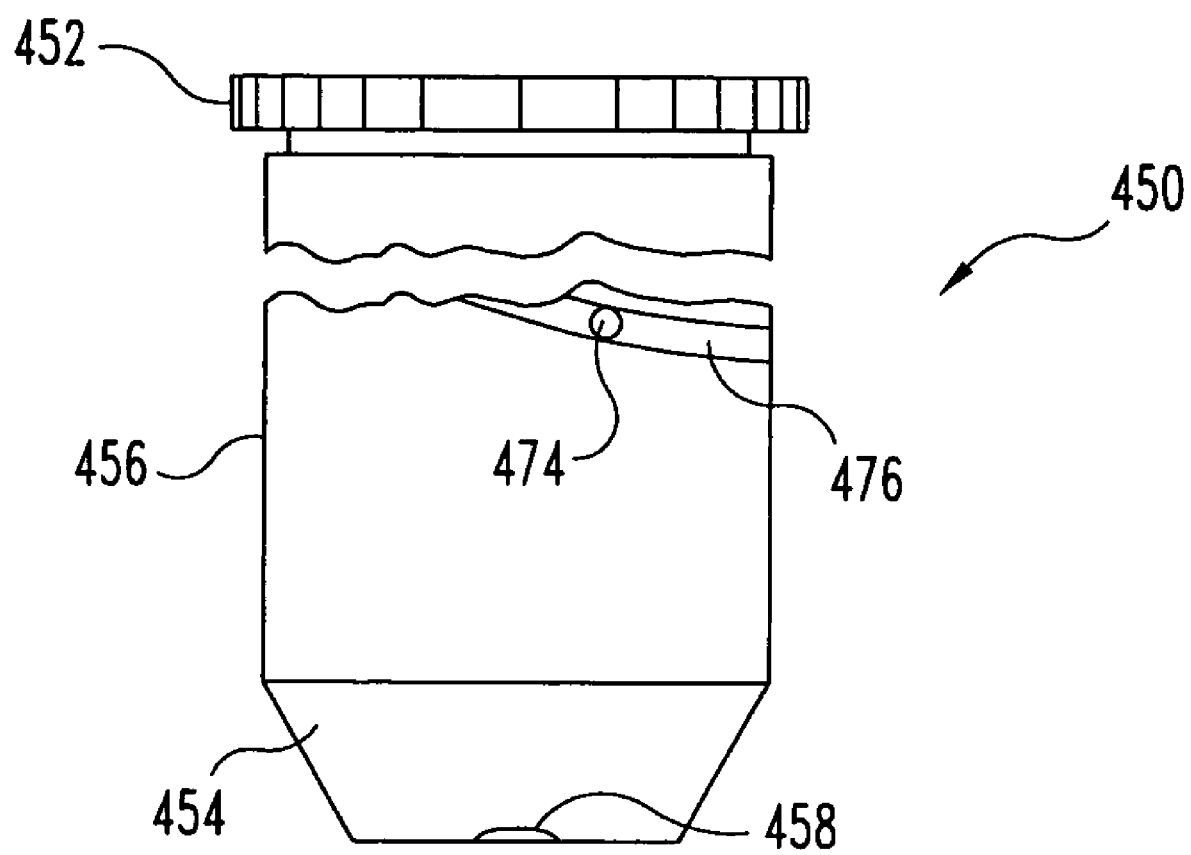
FIG. 29 a front view of a sampling device according to a further embodiment.
Figure 30:
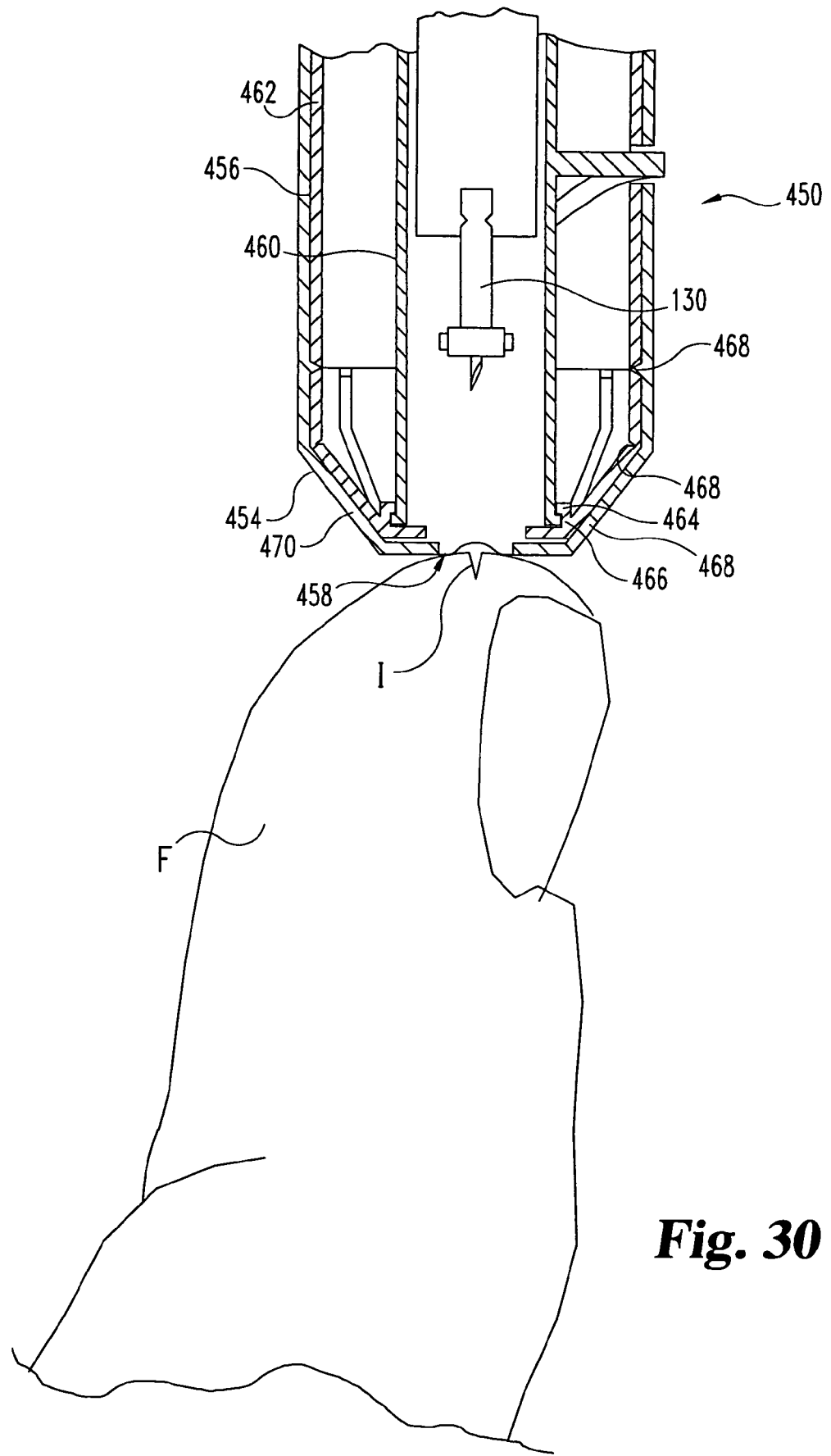
FIG. 30 is a cross-sectional view of the FIG. 29 device configured to express fluid from a fingertip.
Figure 31:
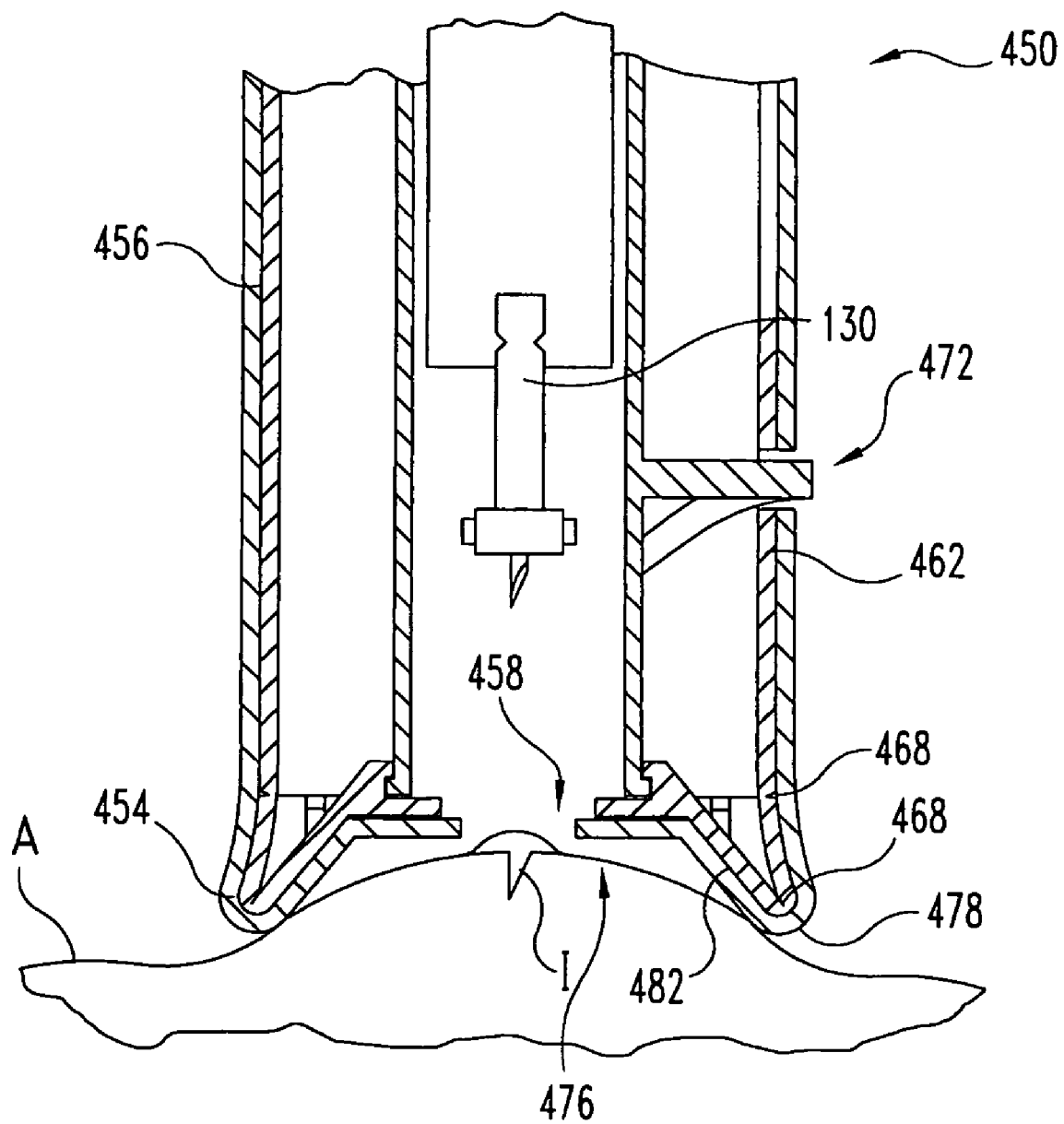
FIG. 31 is a cross-sectional view of the FIG. 29 device configured to express fluid from an alternate site.

A fluid sampling device 450 according to a further embodiment of the present invention is illustrated in FIGS. 29-31. With reference to FIG. 29, the device 450 has an actuation knob 452 at one end and a skin contacting or expression member 454 at the other end. The actuation knob 452 is rotatably mounted on housing 456, and the knob 452 can be rotated in order to change the shape and size of the expression member 454. Like the previous embodiments, device 450 is configured to precisely control the penetration depth of a lancet for safety purposes and is configurable to express fluid from finger as well as from alternate sites. As illustrated in FIG. 30, device 450 includes lancet 130 that is able to control and adjust its penetration depth, as was described above with reference to FIGS. 10-13. It should be appreciated that device 450 can use other types of lancing devices that can control penetration depth of the lancet, such as the embodiments illustrated in FIGS. 14-23. The expression member 454 has a lancet opening 458 through which lancet 130 is able to extend during lancing.

As briefly mentioned above, the expression member 454 is reconfigurable to change shapes depending on the expression site. For instance, the sampling device 450 in FIG. 30 is configured to express fluid from a fingertip or similar site, and in FIG. 31, device 450 is in a configuration to create a larger expression opening in order to express fluid from an alternate site. To accomplish this, the sampling device 450 has an inner tube 460 slidably mounted inside an outer tube 462. The inner tube 460 has a proximal end that is attached to the knob 452. The distal end of the inner tube 460 has a flange 464 that is rotatably coupled to a collar 464 such that the flange 464 is able to rotate relative to the collar 464. In the expression member 454, living hinges 466 connect the collar 464 to the outer tube 462, and each living hinge 466 has a relief notch or portion 468 that allows the living hinge to bend. As shown, the living hinges 466 are covered by a covering 470 that defines opening 458. In the illustrated embodiment, the covering 470 is made of a flexible material that is attached to the living hinges 466. By way of nonlimiting example, the covering 470 can be made of flexible plastic, rubber or the like. The collar 466 provides structural support around opening 458 so that the device 450 is able to express fluid from incision I in fingertip F. However, usually expressing the fingertip F is not required in order to obtain an adequate fluid sample.

The sampling device 450 further incorporates an actuation mechanism 472 that, in conjunction with knob 452, retracts the inner tube 460 inside the outer tube 462, thereby expanding the expression member 454 to the configuration illustrated in FIG. 31. With reference to FIGS. 29 and 30, the actuation mechanism 472 in the illustrated embodiment includes a guide pin 474 that extends from the inner tube 460 into a guide channel 476 in the outer tube 462. As depicted in FIG. 29, the guide channel 476 extends along a generally spiral shaped path on housing 456. Although the guide channel 476 is visible on the outside of the device in FIG. 29, it is contemplated that the guide channel 476 can be enclosed so as to be invisible from the outside. By way of example, the actuation mechanism 472 operates in a fashion similar to that of a lipstick dispenser. As the knob 452 is rotated relative to the housing 456 in a clockwise fashion, as viewed from the proximal end of the device 450, the guide pin 474 slides within channel 474 such that the distal end of the inner tube 460 is drawn inside of the outer tube 462. While the inner tube 460 retracts inside the outer tube 462, the living hinges 468 bend to create an expression opening 476 that is larger than opening 458 such that the device 450 is able to express fluid from alternate site A. As illustrated in FIG. 31, the living hinges 466 bend at middle notch 478 to form an outer expression edge 480 that defines expression opening 476 with an expression surface 482. In the illustrated embodiment, the expression surface 482 has a conical shape. It is contemplated that the shape of the expression member 454 can be changed in other manners. In a further embodiment, the actuation mechanism 472 and inner tube 460 are eliminated such that the user manually pushes in the expression member 454 to create a dented portion on the expression member 454 so that fluid can be expressed from an alternate site.

A body fluid sampling device 500 according to a further embodiment of the present invention is illustrated in FIGS. 32A-32B and 33A-33B. As will be appreciated from the discussion below, the sampling device 500 operates in a fashion similar to the one described above in FIGS. 29-31. The sampling device 500 is configured to be able to change its opening size for lancing and expressing fluid from both fingertips and alternate sites. As depicted, the sampling device 500 includes a housing 502, a deformable cover or membrane 504, a reference tube 506 and a lancet 50. Reference tube 506 is located inside the housing 502, and the membrane 504 stretches between the ends of housing 502 and the reference tube 506. Around the membrane 504, the housing 502 has an expression flange 508 that is rigid and defines an expression opening 510 for expressing fluid from alternate sites. In the illustrated embodiment, the reference tube 506 defines a lancet cavity 512 with an aperture or opening 514 through which the lancet 50 extends so as to lance the skin. About the aperture 514, the reference tube 506 has a reference edge 516 with a reference surface 518 that flattens the skin during lancing. In one embodiment, the membrane 504 is attached around the reference edge 516 of the reference tube 506, and in another embodiment, the membrane 504 is attached to and covers the reference surface 518.

Like the previous embodiments, the illustrated sampling device 500 is operable to create two differently sized openings, one size for lancing and another size for expressing fluids from alternate sites. Similar to some of the previous embodiments, the penetration depth of the lancet 50 is controlled by a fixed stop in the actuation mechanism, such as with a SOFTCLIX brand lancing device. Sampling device 500 in FIG. 32A is illustrated in its lancing configuration such that the sampling device 500 has a first opening size S1 that is sized to flatten the skin around the lancet 50 during lancing. In the illustrated embodiment, the first opening size S1 is based on the diameter of opening 514, and in one particular form, the first opening size S1 is at most 2.5 mm so as to flatten the skin during lancing. The first opening size S1 in other forms can be sized differently. Although the lancing and expressing openings in a number of embodiments throughout the present description have a circular shape, it should be appreciated that these openings can be shaped differently. After the skin is lanced by the lancet 50 with the sampling device 500 in the lancing configuration, the reference tube 506 can be retracted further inside the housing 502 to form a second opening size S2 (FIG. 32B) for expressing fluid from alternate sites. In the illustrated embodiment, the second opening size S2 is based on the diameter of the expression opening 510, and in one particular form, the first opening size S1 is at least 7.0 mm so as to provide an adequate opening size for expressing fluids from alternate sites. In other forms, the second opening size S2 can be sized differently. The expression flange 508 around the expression opening 510 provides a rigid member for expressing fluid.

With reference to FIGS. 34A-34B and 35A-35B, a body fluid sampling device 520 according to another embodiment of the present invention is illustrated. The sampling device 520 includes a housing 522 and a cap 524 mounted to the housing in an extendable manner. Inside the housing 522, lancet 50 with a lancet cartridge housing 526 is mounted. In the illustrated embodiment, the penetration depth of the lancet 50 is controlled by a fixed stop in the actuation mechanism, such as with a SOFTCLIX brand lancing device. The cap 524 is adjustable relative to the housing 522 so as to be able to extend (FIGS. 34A and 35A) and retract (FIGS. 34B and 35B) in order to adjust the penetration depth of the lancet 50 depending on whether a fingertip or an alternate site is being lanced. As shown, the cap 524 defines a lancet opening 528 through which the lancet 50 is able to extend. Around the lancet opening 528, the cap 524 has a finger receiving cavity 530 that is sized and shaped to coincide with the contour of a fingertip. In the illustrated embodiment, the finger receiving cavity 530 has a semispherical shape. An expression ridge 532 that is configured to express fluid from alternate skin sites surrounds the finger receiving cavity 530. In the illustrated embodiment, ridge 532 is continuous, but it is contemplated that in other embodiments, the expression ridge 532 can be discontinuous. For example, the expression ridge 532 in other forms can include notches to permit blood flow.

Figure 34A:
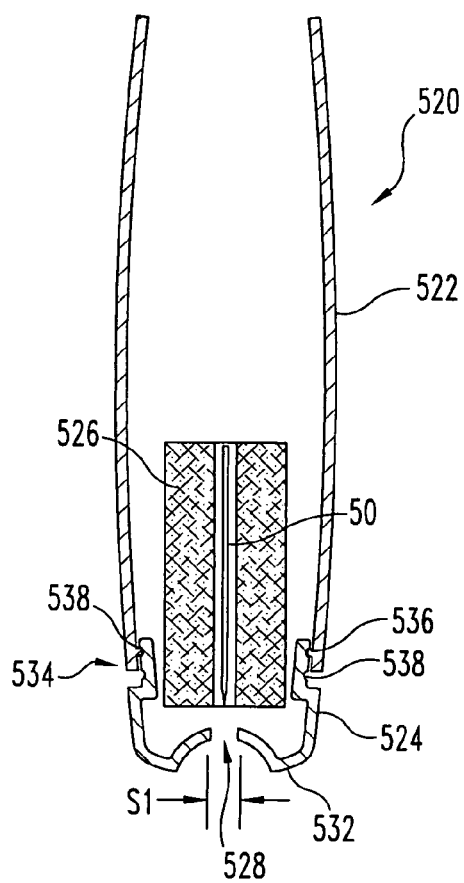
FIGS. 34A and 34B are cross sectional views of a sampling device according to a further embodiment in extended and retracted configurations, respectively.
Figure 34B:
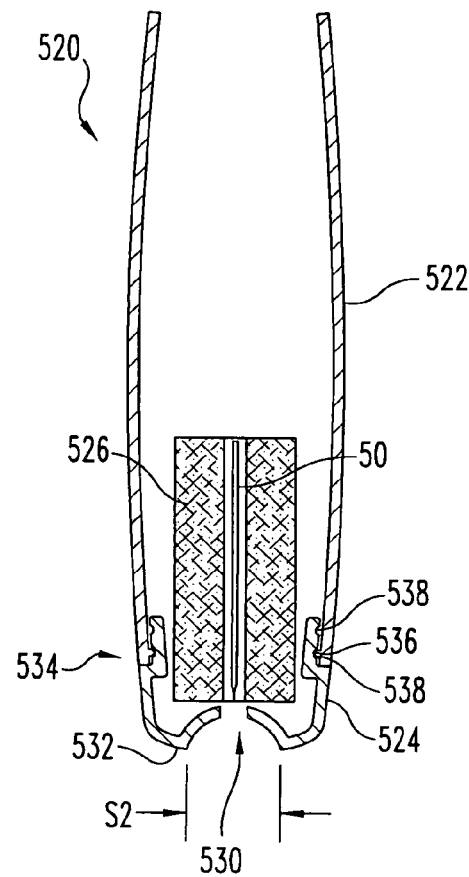
Figure 35A:
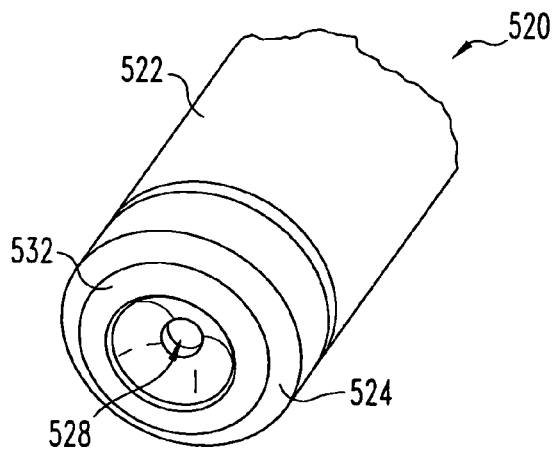
FIGS. 35A and 35B are perspective views of the FIGS. 34A and 34B device in the extended and retracted configurations, respectively.
Figure 35B:
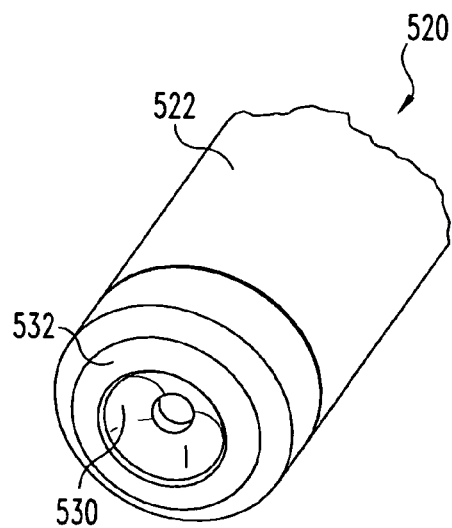

As mentioned above, the actuation mechanism for the lancet 50 extends the lancet 50 at a predetermined stroke length. To adjust to penetration depth of the lancet 50, the cap 524 is extended, as is depicted in FIGS. 34A and 35A, to decrease the penetration depth of the lancet 50, and the cap 524 is retracted, as is shown in FIGS. 34B and 35B, to increase the penetration depth of the lancet 50. The sampling device 520 includes an adjustment mechanism 534 that adjusts the relative positions of the cap 524 and the housing 522. In the illustrated embodiment, the adjustment mechanism 534 includes a ridge 536 in the housing 522 that engages a series of grooves 538 formed in the cap 524. The grooves 538 in the illustrated embodiment are formed at predefined extended and retracted positions. For instance, when lancing a fingertip, the fingertip is received inside the finger receiving cavity 530, and since the fingertip in cavity 530 is closer to the lancet 50, the cap 524 is extended so as to reduce the penetration depth of the lancet 50. The cap 524 is extended such that the ridge 536 in the housing 524 engages the groove 538 in the cap 524 to secure the cap 524 at the extended position.

As should be appreciated, when the sampling device 520 lances an alternate site, such as a forearm, the skin at the alternate site does not bulge to a great extent inside the fingertip receiving cavity 530. As a result, if the cap 524 remained in the extended position, the lancet 50 would probably not lance deeply enough to create an adequate fluid supply, or not even lance the skin at all. To ensure that the lancet adequately penetrates the skin, the cap 524 can be retracted, as shown in FIGS. 34B and 35B, and the cap 524 is secured in the retracted position through the engagement between the ridge 536 and the groove 538 at the retracted position. It is contemplated that the adjustment mechanism 534 can include other types of adjustment mechanisms. For example, the cap 524 can be threaded onto the housing 522 such that the cap 524 can be extended and retracted. After the skin is lanced at the alternate site, the fluid from the incision by pressing the expression ridge 532 around the incision. As shown in FIGS. 34A and 34B, the size S2 of the finger expression cavity 530 is larger than the size S1 of lancet opening 528 so that the cap 524 is able to better express fluid from the alternate site. In one form, the size S1 of the lancet opening 528 is at most 2.5 mm, and the size S2 of the finger receiving cavity 530 is at least 7.0 mm. However, in other forms, the opening sizes can be sized differently.

Figure 36A:
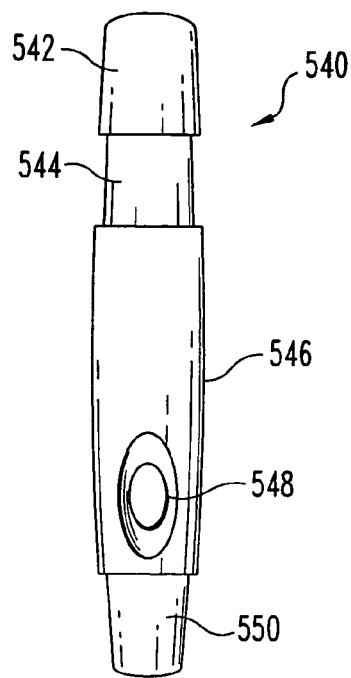
FIGS. 36A and 36B are cross sectional views of a sampling device according to still yet another embodiment in lancing and expressing configurations, respectively.
Figure 36B:
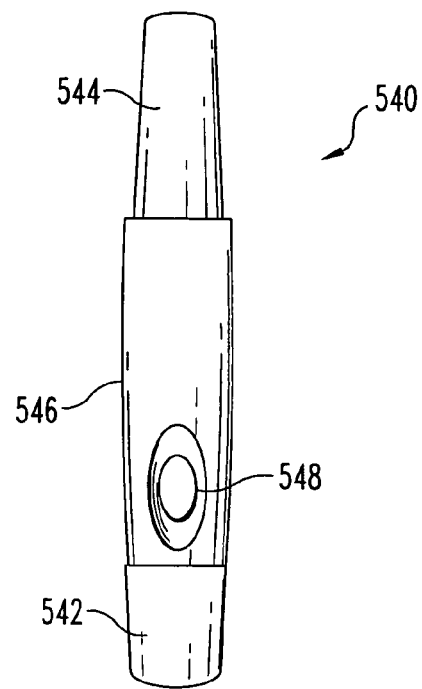
Figure 37A:
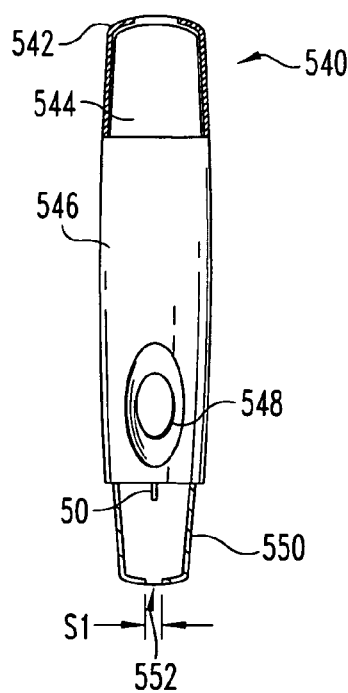
FIGS. 37A and 37B are perspective views of the FIGS. 36A and 36B device in the lancing and expressing configurations, respectively.

A body fluid sampling device 540 according to another embodiment will now be described with reference to FIGS. 36A-36B and 37A-37B. The sampling device 540 includes an expression cap 542 for expressing fluids from alternate sites, a priming mechanism 544 for priming lancet 50, a housing 546, a firing button 548 to fire the lancet 50, and a lancing cap 550. To prime the sampling device 540, the expression cap 542 covers one end of the priming mechanism 544, as is shown in FIG. 36A. In one form, the priming mechanism 544 is constructed so that the expression cap 542 must cover he priming mechanism 544 before the sampling device 540 can be primed, and in another form, the expression cap 542 is not required to prime the sampling device 540. The sampling device 540 in the illustrated embodiment operates in a fashion similar to a SOFTCLIX brand lancing device. With the expression cap 542 covering the priming mechanism 544, the priming mechanism 544 is pressed toward the housing 546 into a cocked or primed position, as is illustrated in FIG. 37A. The lancet 50 can be fired by pressing the firing button 548 so as to lance the skin. As shown, the lancing cap 550 defines a lancet opening 552 through which the lancet 50 extends during lancing. The lancet opening 552 is sized to flatten the skin around the lancet 50 so as to control the penetration depth of the lancet 50. In one form, the lancet opening 552 has size S1 that is not greater than 2.5 mm, but in other forms, the lancet opening 552 can be sized differently.

Figure 37B:
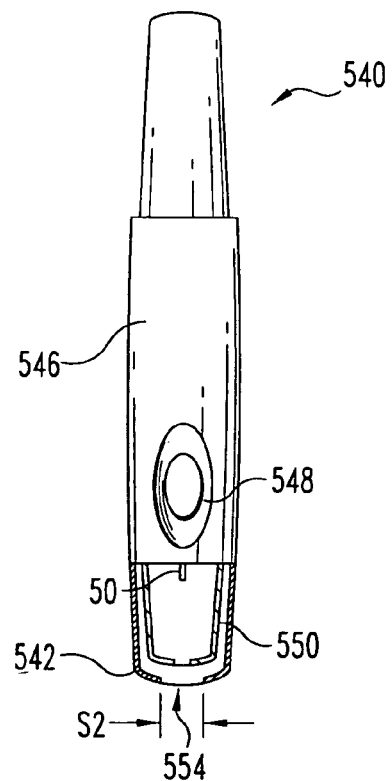

After the skin is lanced, the sampling device 540 can be configured to express fluids from alternate sites, such as the forearm. To express fluid from alternate sites, the expression cap 542 is removed from the priming mechanism 544 and then fitted over the lancing cap 550. In one embodiment, the expression cap 542 is sized so that the expression cap 542 is able to be frictionally secured to the lancing cap 550. Referring to FIG. 37B, the expression cap 542 defines an expression opening 554 in which fluid from an incision at an alternate site is expressed. The expression opening 554 is sized so that an adequate amount of fluid can be expressed by pressing the expression cap 542 around the incision. In one form, the expression opening 554 has size S2 that is at least 7.0 mm, but in other forms, the expression opening 554 can be sized differently. After expressing fluid from the incision, the expression cap 542 can be cleaned for reuse, or discarded and replaced with a new one.

FIGS. 38A-38B and 39A-39B illustrate a body fluid sampling device 556, according to another embodiment, that utilizes a flip cap 558 in order to change opening sizes. As shown, the flip cap 558 is pivotally attached to housing 560 through a pivot pin 562. The housing 560 has a cap protrusion 564 around which the flip cap 558 is received when in a closed position, as is depicted in FIGS. 38A and 39A. The cap protrusion 564 defines an expression opening 566 for expressing fluid, and the flip cap 558 has a lancet opening 568 through which lancet 50 in cartridge 526 is able to extend and lance the skin. The lancet opening 568 has is sized (S1) so as to be able to flatten the skin around the lancet 50 during lancing, thereby minimizing variations in penetration depth. In one form, the size S1 of the lancet opening 568 is at most 2.5 mm, and in other embodiments, the size S1 of the lancet opening 568 can be different. With reference to FIGS. 38A and 39A, the flip cap 558 covers the expression opening 566 during lancing such that lancet 50 passes through the lancet opening 568. After lancing, the flip cap 558 can be flipped away from the housing 556, as illustrated in FIGS. 38B and 39B, so that the sampling device 556 can express fluid from alternate sites. As shown, the expression opening 566 is sized (S2) so as to be able to expression an adequate sample size of fluid from the incision. In one form, the size of the expression opening 566 is at least 7.5 mm, but in other forms, the expression opening 566 is sized differently. When expressing fluid from an alternate site, the cap protrusion 564 is pressed around the incision such that fluid is drawn to the surface of the skin. After a sufficient amount of fluid collects on the skin, the fluid can be collected using a test strip or capillary tube, for example.

Figure 40A:
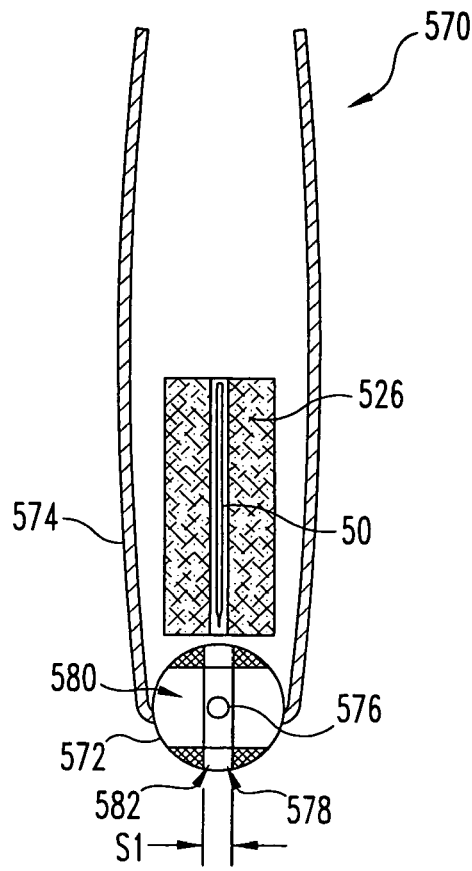
FIGS. 40A and 40B are cross sectional views of a sampling device according to another embodiment in lancing and expressing configurations, respectively.
Figure 40B:
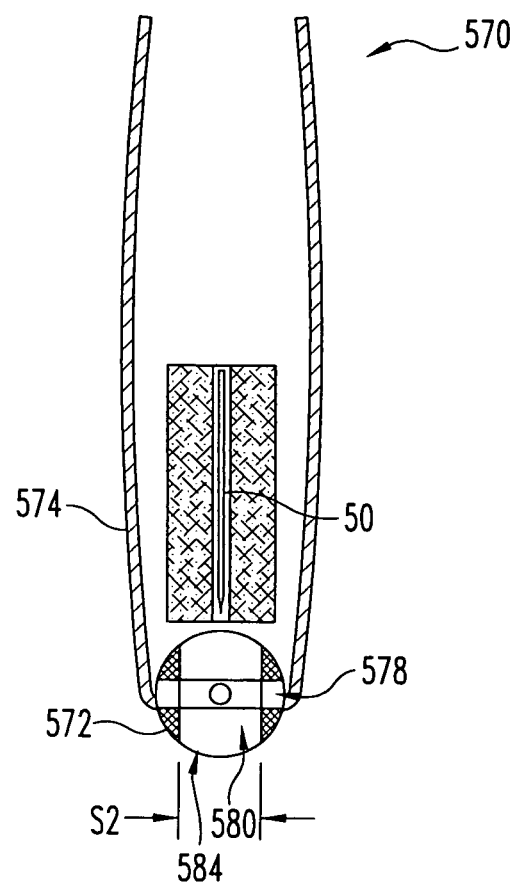
Figure 41A:
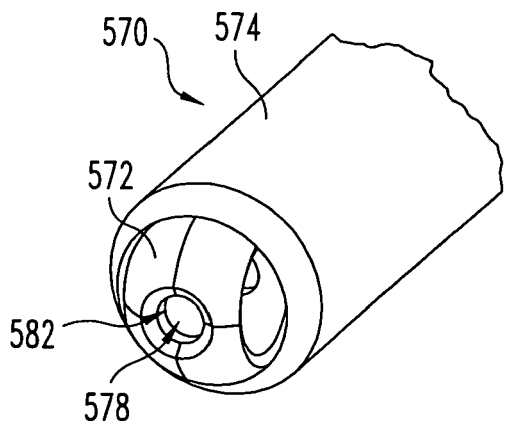
FIGS. 41A and 41B are perspective views of the FIGS. 40A and 40B device in the lancing and expressing configurations, respectively.

A body fluid sampling device 570 according to a further embodiment of the present invention is illustrated in FIGS. 40A-40B and 41A-41B. Similar to the previously described embodiments, the sampling device 570 is able to change opening sizes for lancing and expressing fluid. In the illustrated embodiment, the sampling device 570 includes a lancet 50 with a cartridge 526 and a ball member 572, which can be rotated in order to change the opening sizes. The ball member 572 is rotatably mounted at one end of housing 574 in the sampling device 570. The ball member 572 in the embodiment illustrated in FIGS. 40A-40B is pivotally mounted onto one or more pivot pins 576 in the housing 574. However, it is contemplated that the ball member 572 in other embodiments can be rotatably coupled to the housing 574 in other manners. For instance, the ball member 572 in another embodiment can be mounted in a fashion similar to that of a ball point pen such that the ball member 572 is able to rotate about multiple axes. Referring to FIGS. 40A-40B, the ball member 572 has a lancet bore 578 through which the lancet 50 extends during lancing and an expression bore 580 in which fluid can be expressed from alternate sites. Around a lancet opening 582 of the lancing bore 578, as shown in FIGS. 40A and 41A, the ball member 572 is configured to flatten the skin during lancing in order to control the penetration depth of the lancet 50. The lancet opening 582 is sized (S1) so that the skin around the lancet 50 during lancing does not substantially bulge. In one form, the size S1 of the lancet opening 582 is not greater than 2.5 mm so as to minimize bulging of the skin. However, it is contemplated that the size S1 of the lancet opening 582 can differ in other embodiments. The expression bore 580 has an expression opening 584, which is sized (S2) to express fluid from alternate sites. The size S2 of the expression opening 584 in one form is at least 7.0 mm wide, but it is contemplated that the size S2 of the expression opening 584 can be different. Although only a single lancet opening 582 and a single expression opening 584 is illustrated, it should be understood that the ball member 572 in other embodiments can include multiple openings that can have different sizes and/or shapes for different locations on the body. For example, the ball member 572 can have a series of progressively larger expression openings 584 so that the user can select a suitably sized opening for their particular situation.

Figure 41B:
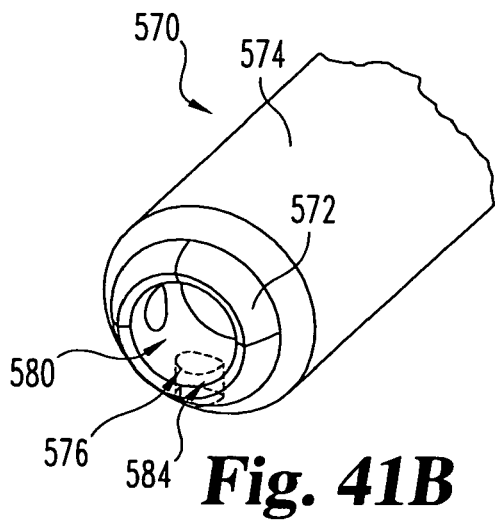

To lance the skin with the sampling device 570, the ball member 572 is rotated such that the lancet bore 578 is aligned with the lancet 50 as depicted in FIG. 40A, thereby allowing the lancet 50 to pass through the lancet bore 578. In the illustrated embodiment, the ball member 572 is manually rotated into position. Nevertheless, it should be appreciated that the ball member 572 in other embodiments can be automatically oriented through a mechanical means, such as with a motor or a biased spring, for example. As noted above, by lancing with the lancet opening 582 placed against the skin, the skin is flattened around the lancet 50 so that the penetration depth of the lancet 50 can be controlled. Referring to FIGS. 40B and 41B, after the incision is formed in an alternate site, the ball member 572 is rotated so that the expression opening 584 is able to surround the incision so that the ball member 572 is able to be pressed against the skin to express fluid from the incision. The sampling device 570 can be pressed once or repeatedly pressed against the skin to express fluid from an incision.

Figure 42A:
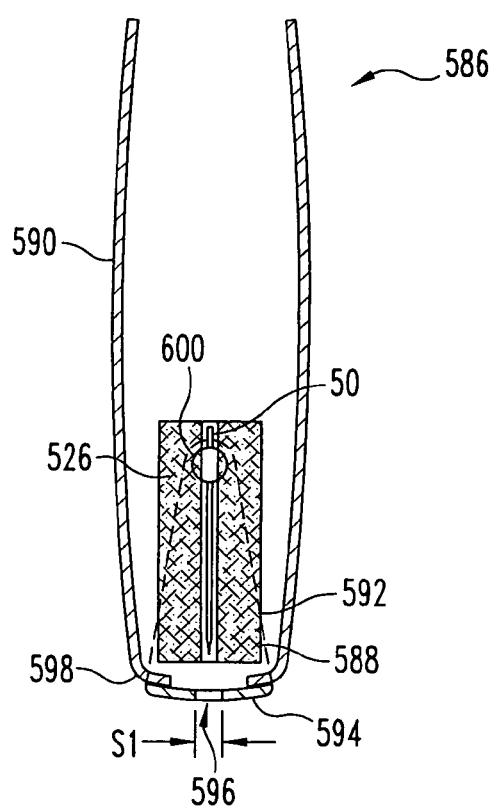
FIGS. 42A and 42B are cross sectional views of a sampling device according to still yet another embodiment in lancing and expressing configurations, respectively.
Figure 42B:
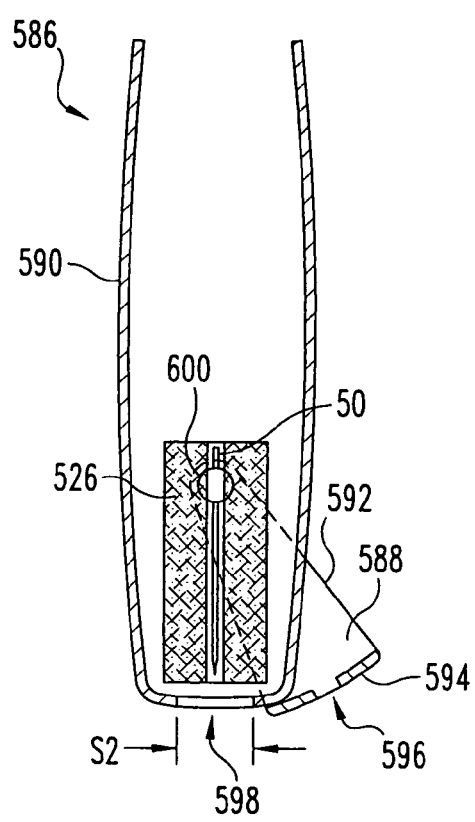
Figure 43:
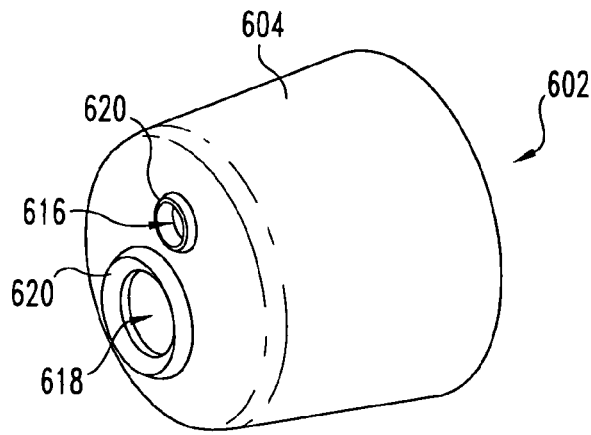
FIG. 43 is a perspective view of a sampling device according to a further embodiment.

Referring now to FIGS. 42A and 42B, a body fluid sampling device 586 according to a further embodiment is illustrated, which is able to change its opening size through a pivot member 588. The sampling device 586 includes one or more lancets 50 received in magazine 526 for lancing the skin. As shown, the pivot member 588 is pivotally attached to a housing 590 of the sampling device 586. The pivot member 588 according to the illustrated embodiment includes a pair pivot arms 592 that are connected together through a reference member 594, which gives the pivot member 588 an overall, unshaped appearance. The reference member 594 defines a lancet opening 596, which is sized (S1) to minimizes skin bulging during lancing with lancet 50, thereby improving penetration depth control of the lancet 50. In one form, the size S1 of the lancet opening 596 is not greater than 2.5 mm so as to minimize bulging of the skin. However, it is contemplated that the size S1 of the lancet opening 582 can differ in other embodiments. As depicted in FIG. 42B, the housing 590 defines an expression opening 598, which is sized (S2) to express fluid from alternate sites. The size S2 of the expression opening 598 in one form is at least 7.0 mm wide in diameter, but it is contemplated that the size S2 of the expression opening 598 can be different. Although only a single lancet opening 596 and a single expression opening 598 are illustrated, it should be appreciated that the pivot member 588 and/or the housing 590 in other embodiments can include multiple openings that can have different sizes and/or shapes. Extending from opposite sides of the housing 590, pivot pins 600 pivotally couple the pivot arms 592 to the housing 590. It should be appreciated that the pivot member 588 can be pivotally coupled to the housing 590 in other manners.

In order to lance the skin, the pivot member 588 is pivoted so as to align the lancet opening 596 with the lancet 50, as is shown in FIG. 42A. To express fluid from an alternate site, the pivot member 588 is pivoted such that the expression opening 598 is exposed. The expression opening 598 is pressed around the incision so as to express fluid from the incision. In one form, the pivot member 588 is pivoted manually by the user, but it is contemplated that in other embodiments the pivot member 588 can be pivoted automatically, such as through a motor or in some other manner.

FIGS. 43, 44, 45A and 45B illustrate a cap assembly 602 that is used to provide differing opening sizes for a body fluid sampling device. For the sake of clarity, only the cap assembly 602 of the device is illustrated. It nonetheless should be appreciated that the cap assembly is used in conjunction with a lancet or some other means for forming an incision so as to control the depth of the incision when formed in a fingertip or an alternate site; while at the same time providing an adequate opening size for expressing body fluid from alternate sites. As illustrated, the cap assembly includes an outer cap 604 that is rotatably mounted on an inner cap 606. The inner cap 606 has a mounting flange 608 at which the cap assembly 602 is attached to the rest of the sampling device. The inner cap 606 has a series of ridges 610 that engage grooves 612 formed inside the outer cap 604. In one form, the ridges 610 are ring-shaped so that the penetration depth of the lancet remains constants, and in another form, the ridges 610 are helically shaped so that the penetration depth of the lancet can be adjusted. The inner cap 606 defines a lancet passageway 614 through which the lancet passes during lancing.

Figure 44:
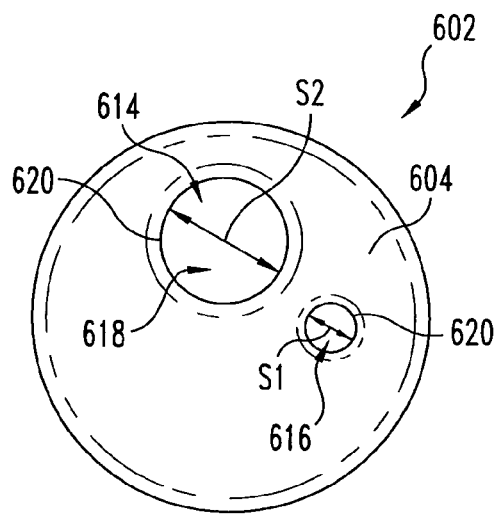
FIG. 44 is a front view of the FIG. 43 device.

As depicted in FIG. 44, the outer cap 608 defines a lancet opening 616 and an expression opening 618. The openings 616, 618 on the outer cap 608 are positioned to be able to be aligned with the lancet passageway 614 in the inner cap 606. In the illustrated embodiment, the openings 616, 618 in the outer cap 608 align with the lancet passageway 614 in a generally concentric manner, but it is contemplated that in other embodiments the alignment can be nonconcentric. The lancet opening 616 is sized (S1) to minimizes skin bulging during lancing with lancet, thereby improving penetration depth control. In one form, the size S1 of the lancet opening 616 is not greater than 2.5 mm so as to minimize bulging of the skin. However, it is contemplated that the size S1 of the lancet opening 616 can differ in other embodiments. The expression opening 618 is sized (S2) to express fluid from alternate sites. The size S2 of the expression opening 618 in one form is at least 7.0 mm wide in diameter, but it is contemplated that the size S2 of the expression opening 598 can be different. Although only a single lancet opening 616 and a single expression opening 618 are illustrated, it should be appreciated that the outer cap 604 in other embodiments can include multiple openings that can have different sizes and/or shapes. As shown, expression ridges 620 for expressing fluid surround both the lancet opening 616 and the expression opening 618.

Figure 45A:
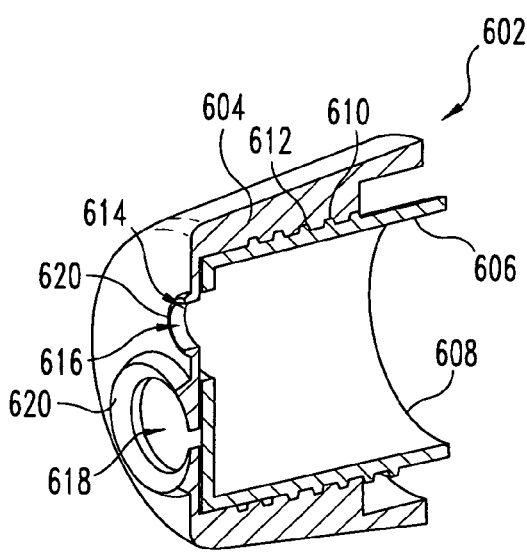
FIGS. 45A and 45B are cross sectional views of the FIG. 43 device in lancing and expressing configurations, respectively.
Figure 45B:
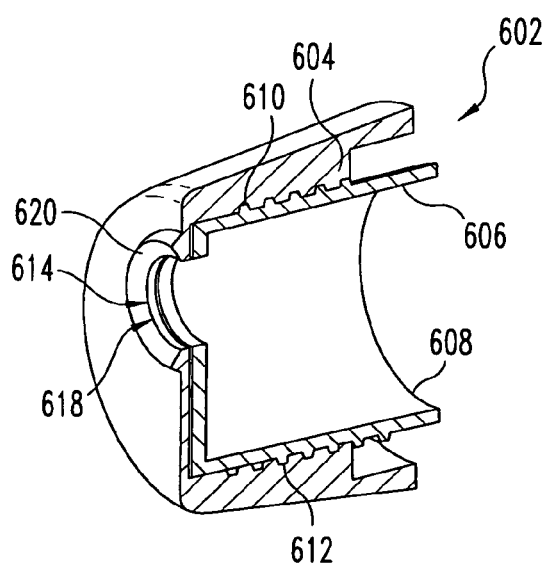

Referring to FIG. 45A, to lance the skin, the outer cap 604 is rotated so that the lancet opening 616 is aligned with the lancet passageway 614 in the inner cap 606. To expression body fluid from an alternate site, the outer cap 604 is rotated such that the expression opening 618 aligns with the lancet passageway 614. Once aligned, the expression opening 618 is pressed around the incision so that fluid is expressed from the incision. In the illustrated embodiment, the outer cap 604 is manually rotated into position, but it is contemplated that in other embodiments the outer cap 604 can be automatically rotated, such as with a motor or a spring.

Figure 46:
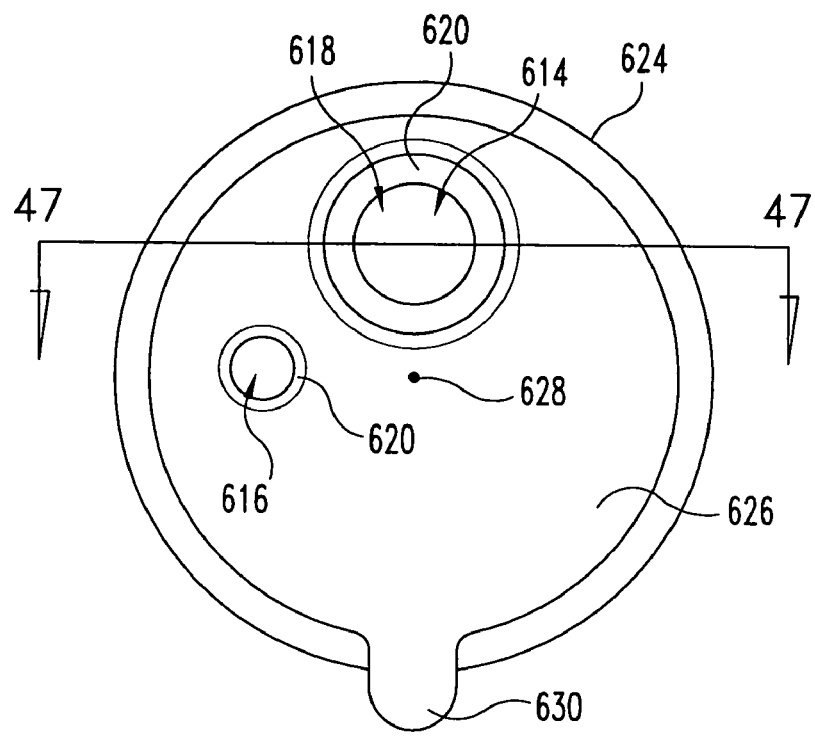
FIG. 46 is a front view of a sampling device according to another embodiment.
Figure 47:
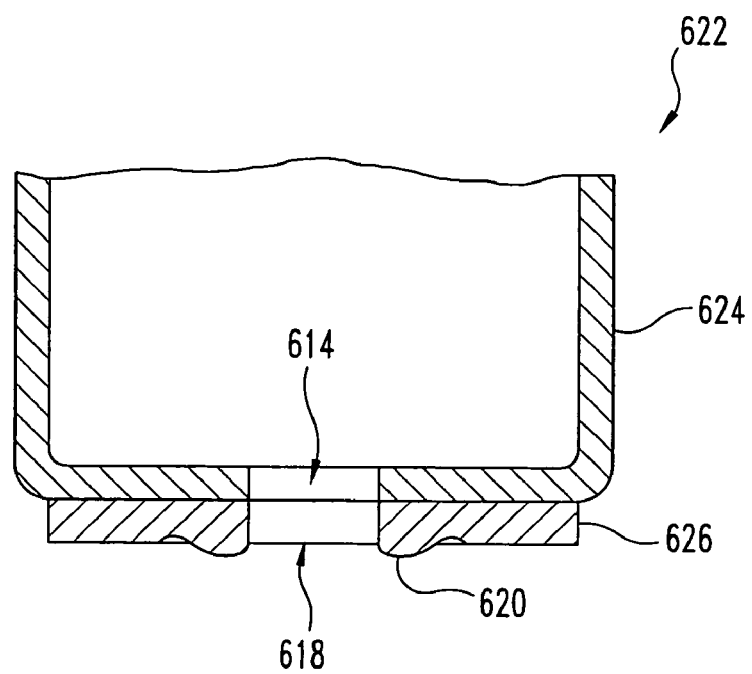
FIG. 47 is a cross sectional view of the FIG. 46 device as taken along line 47-47 in FIG. 46.

Referring to FIGS. 46 and 47, a cap assembly 622 according to another embodiment includes a base cap 624 that is configured to secure to a body fluid sampling device. For the sake of clarity, the rest of the body fluid sampling device, such as the lancing mechanism, is not illustrated. A skin contacting plate 626 is rotatably mounted to the base cap 624 via pivot pin 628. In other embodiments, it is contemplated that the skin contacting plate 626 can be pivoted in others manners. As shown in FIG. 46, the skin contacting plate 626 has a handle tab 630 that allows the user to rotate the skin contacting plate 626. It should be understood that the skin contacting plate 626 in other embodiments can be rotated automatically. Lancet passageway 614 is defined in the base cap 624 to permit the passage of a lancet or some other incision forming means during incision formation. Like the outer cap 604 in FIG. 43, the skin contacting plate 626 in FIG. 46 has lancet opening 616 and expression opening 618, both of which are surrounded by expression ridges 620. The openings 616, 618 on the skin contacting plate 626 are positioned to align with the lancet passageway 614. In the illustrated embodiment, the openings 616, 618 on the skin contacting plate 626 are positioned to align concentrically with the lancet passageway 614, but in other embodiments, they can align in a nonconcentric manner. During lancing, the lancet opening 616 on plate 626 is aligned with the lancet passageway 614 so the skin remains relatively flat as the lancet pierces the skin. In order to express fluid from alternate sites, the user rotates the skin contacting plate 626 via tab 630 so that the expression opening 618 aligns with the lancet passageway 614. The expression opening 618 is pressed around the incision so that fluid is expressed from the incision.

Figure 48A:
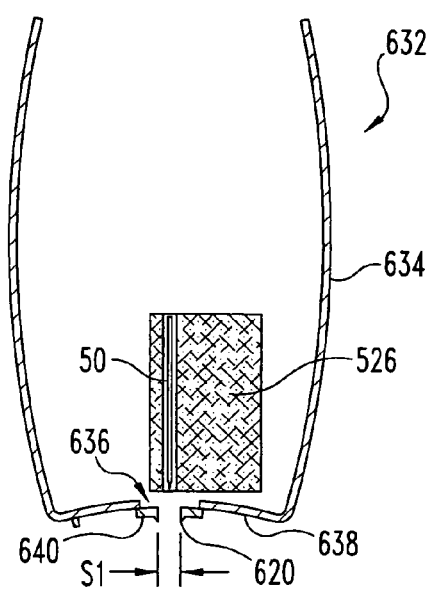
FIGS. 48A and 48B are cross sectional views of a sampling device according to another embodiment in lancing and expressing configurations, respectively.
Figure 48B:
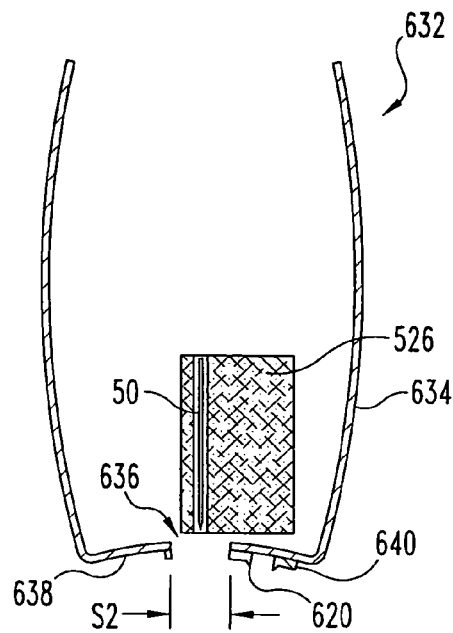
Figure 49A:
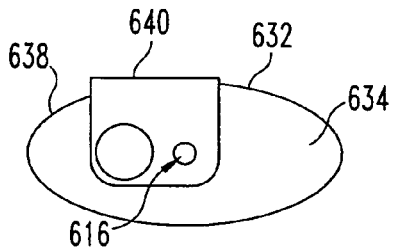
FIGS. 49A and 49B are top views of the FIGS. 48A and 48B device in the lancing and expressing configurations, respectively.
Figure 49B:
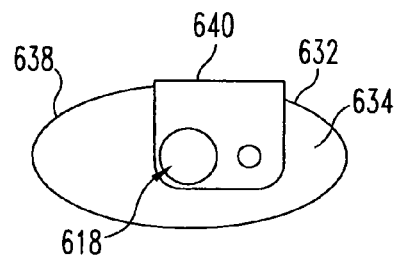
Figure 50A:
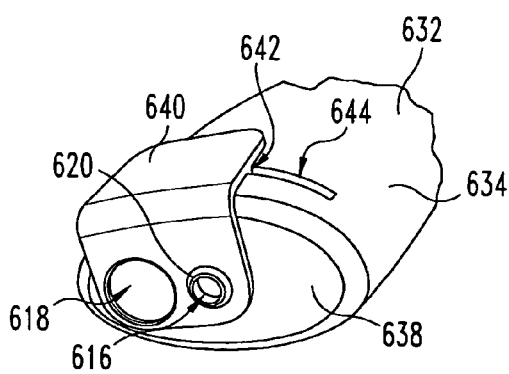
FIGS. 50A and 50B are perspective views of the FIGS. 48A and 48B device in the lancing and expressing configurations, respectively.
Figure 50B:
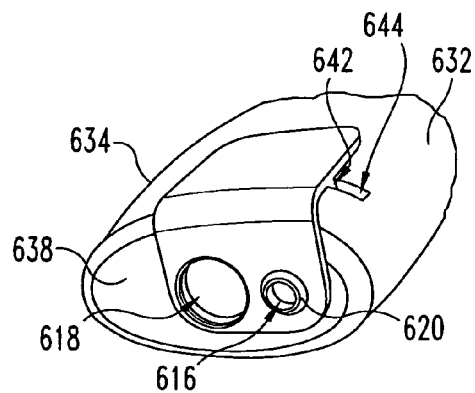

A body fluid sampling device 632, according to a further embodiment, that is able to provide a wider opening for expressing body fluid from alternate sites will now be described with reference to FIGS. 48A, 48B, 49A, 49B, 50A and 50B. Similar to the previous embodiments, the sampling device 632 includes one or more lancets 50 housed in magazine 526. Nevertheless, it should be appreciated that the body fluid sampling device 632 can incorporate other types of devices for forming incisions. As shown, the lancets 50 are housed in a housing 634 that defines a lancet passageway 636, through which the lancets 50 pass during lancing. In the illustrated embodiment, the housing 634 has an end surface 638 that is concavely shaped, as depicted in FIGS. 48A and 48B, and that is generally oval in shape. As should be appreciated, the housing 634 along with its end surface 638 can be shaped differently. A slide member 640 is slidably coupled to the housing 634, and as shown, the slide member 640 is L-shaped so as to extend from the side of the housing 634 to over the end surface 638. The slide member 640 has a slide tab 642 that is slidably received in a slide groove 644 formed in the housing 634. Along the end face 638, the slide member 640 has lancet opening 616 that is sized (S1) to minimizes skin bulging during lancing and expression opening 618 that is sized (S2) to express fluid from alternate sites. The lancet opening 616 and the expression opening 618 are aligned in a side-by-side relationship so that each can be slid over and aligned with the lancet passageway 636. Only the lancet opening 616 is surrounded by expression ridge 620 in the illustrated embodiment, but it is contemplated that expression ridges 620 can surround both openings 616, 618 on the slide member 640 or can be entirely omitted. Although the slide member 640 in the illustrated embodiment has two openings, it is contemplated that the slide member 640 can have more than two openings of differing size. During lancing, the lancet opening 616 is positioned over the lancet passageway 636, and when fluid is expressed from an alternate site, the expression opening 618 is slid to a position over the lancet passageway 636.

Figure 51:
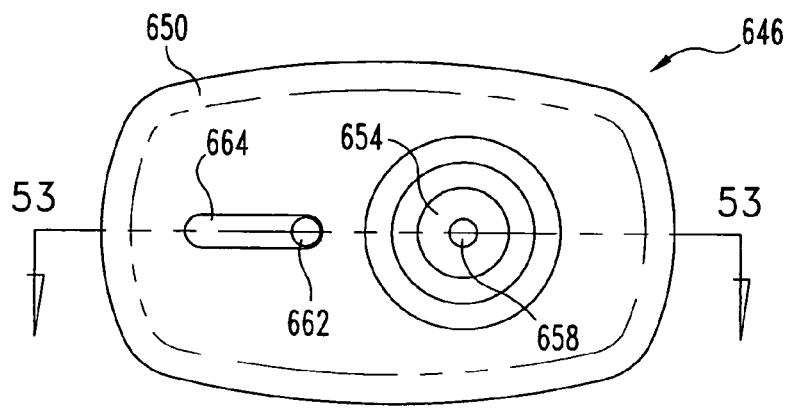
FIG. 51 is a top view of a sampling device according to another embodiment in a lancing configuration.
Figure 52:
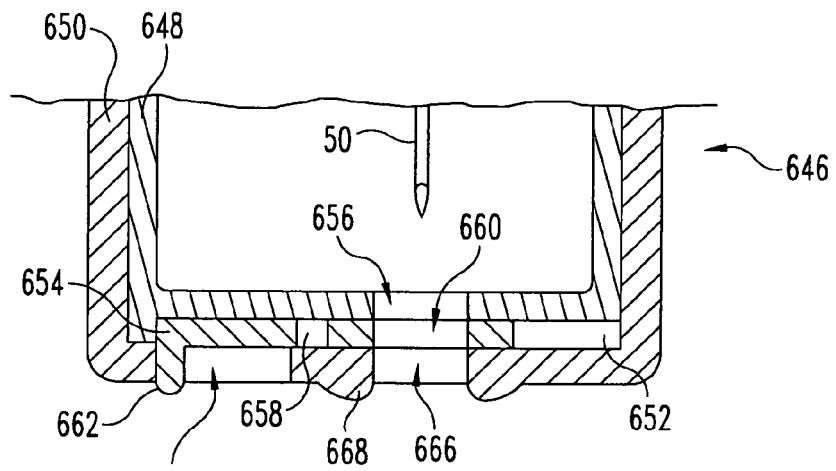
FIG. 52 is a cross sectional view of the FIG. 51 device in an expressing configuration.
Figure 53:
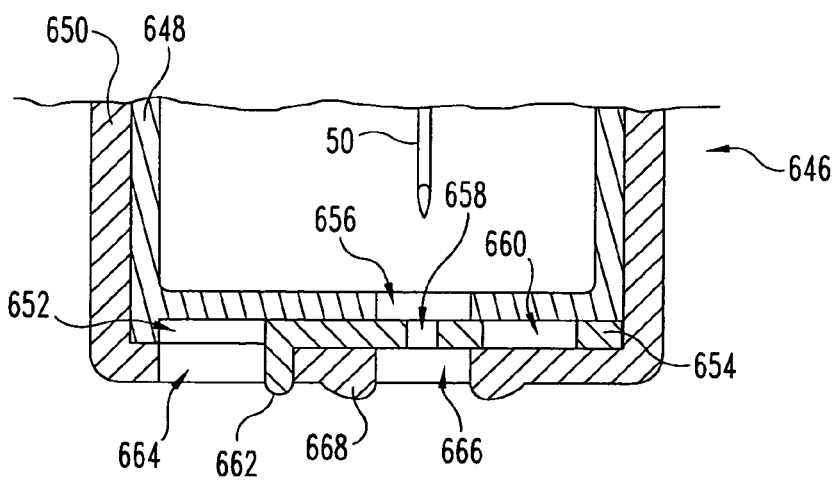
FIG. 53 is a cross sectional view of the FIG. 51 device as taken along line 53-53 in FIG. 51.

Referring now to FIGS. 51, 52 and 53, a body fluid sampling device 546 according to another embodiment of the present invention is illustrated. As depicted, the sampling device 546 includes an inner cap 648 that is enclosed in an outer cap 650. The inner cap 648 defines a slide groove 652 in which a slide member 654 is slidably disposed between the inner cap 648 and the outer cap 650. Along the slide groove 652, the inner cap has a lancet passageway 656 through which lancet 50 of the sampling device 546 lances the skin. As should be appreciated, other means for forming an incision in the skin can also be used in the sampling device 546. Like the previous embodiments, the slide member 654 has a lancet opening 658 that that is sized to minimize skin bulging during lancing and expression opening 660 that is sized to express fluid from alternate sites. The slide member 654 further incorporates an actuation tab 662 for moving the slide member 654 that extends through a guide slot 664 in the outer cap 650. The outer cap 650 has a skin reception opening 666 in which skin is received during lancing and expressing of body fluid. Around opening 666, the outer cap 650 has an expression ridge 668 that is configured to express fluid.

To control the penetration depth of the lancet 50 during lancing, the user moves the actuation tab 662 so that the lancet opening 658 of the slide member 654 is positioned over the lancet passageway 656, as is shown in FIGS. 51 and 53. Although the slide member 654 is manually moved in the illustrated embodiment, it is contemplated that the slide member 654 can be automatically moved in other embodiments. When the device 646 is placed against the skin, the slide member 654 flattens the skin around the lancet 50 as the skin is pierced, thereby minimizing variations in penetration depth of the lancet 50. In order to express fluid from an alternate site, the slide member 654 is slid so that the expression opening 660 is positioned over the lancet passageway 656, and the device 646 is pressed against the skin with the expression ridge 668 surrounding the incision.

In accordance with another embodiment of the present invention, a body fluid sampling device 670, which is illustrated in FIGS. 54A, 54B, 55A and 55B, uses a petal member 672 to form variable sized openings. As shown, the petal member 672 has a nosepiece portion 674 that is tapered and has a nosepiece opening 676. One or more slots 678 in the petal member 672 longitudinally extend from the nosepiece opening 676 to form one or more petals 680. In the illustrated embodiment, the petal member 672 has four (4) petals 680, but it is contemplated that in other embodiments the petal member 672 can have more or less petals 680 than is shown. The petals 680 in the illustrated embodiment are made of a resilient material, such as a plastic or metal, so as to bias the petals 680 away from one another in a radially outward manner. It should be appreciated that the petals 680 can be made of other types of materials. The petal member 672 is housed in a petal cartridge 682, which pushes the petals 680 together. Inside the petal cartridge 682, a spring 684 biases the nosepiece 674 of the petal member 672 out of the petal cartridge 682. The petal cartridge 682 has a nosepiece flange 686 that curves in a radially inward direction to push the petals 680 together when the nosepiece 674 is outwardly biased. When the petals 680 are pushed together, as shown in FIGS. 54A and 55A, the nosepiece opening 676 is sized (S1) to minimizes skin bulging during lancing.

Referring to FIGS. 55A and 55B, the sampling device 670 further includes a retraction mechanism 688 for retracting the petals 680 inside the petal cartridge 682. According to the illustrated embodiment, the retraction mechanism 688 has an actuation handle 690 attached to the petal member 672. As shown, the actuation handle 690 handle slots 692 formed in both the petal cartridge 682 and housing 694. When expressing fluid from alternate sites, the actuation handle 690 is pulled back in the handle slots 692 so that the sampling device 670 has a second sized opening S2 that is larger than the first S1. The petals 680 are outwardly biased against the petal cartridge 682 so that the petals 680 spread apart as the petal member 672 is retracted inside the cartridge 682. In one form, the handle slots 692 have notches for retaining the actuation handle 690 in the retracted position against the force of the spring 684. According to one embodiment, the petals 680 are fully retracted inside the petal cartridge 682 such that the nosepiece flange 686 presses against the skin to express the fluid. It is contemplated that in other embodiments the petals 680 are only partially retracted such that the petal 680 are able to form variable sized expression openings for expressing fluid. Besides the actuation handle 692, it is contemplated that the retraction mechanism can use other types of mechanisms for retracting the petals 680. After fluid is expressed from an alternate site, the spring 684 pushes the petals 680 back into the lancing configuration, as is shown in FIGS. 54A and 55A.

Figure 56:
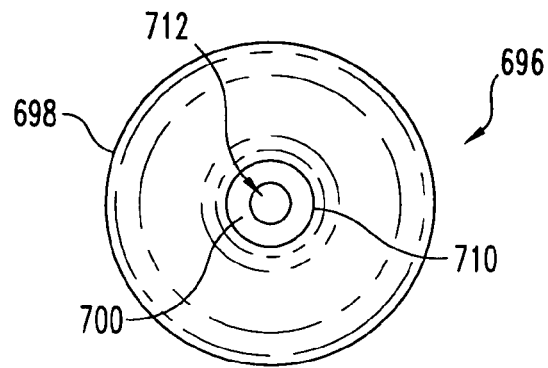
FIG. 56 is a top view of a sampling device according to another embodiment.
Figure 57A:
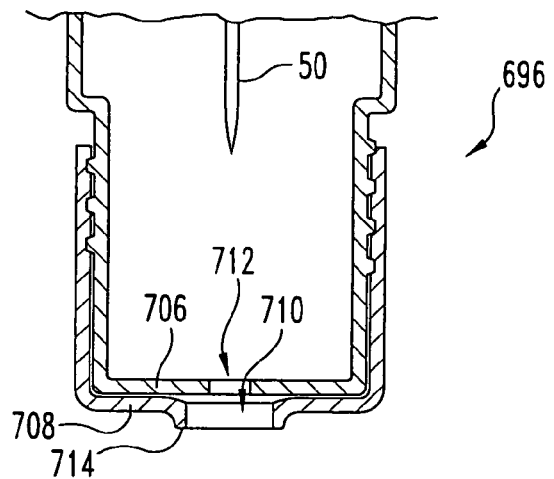
FIGS. 57A and 57B are cross sectional views of the FIG. 56 device in lancing and expressing configurations, respectively.
Figure 57B:
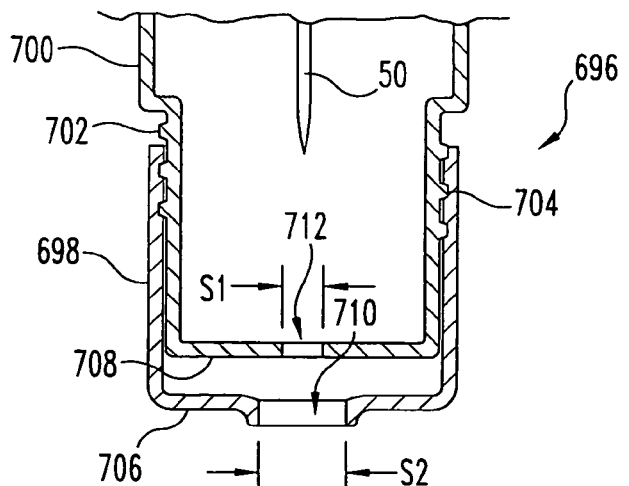

A body fluid sampling device 696, according to still yet another embodiment, is illustrated in FIGS. 56, 57A and 57B. As depicted, the sampling device 696 has an outer cap 698 that is coupled to an inner cap 700. The inner cap 700 has one or more engagement ridges or threads 702 that engage thread notches 704 formed in the outer cap 698. In one form, the threads 702 are in the form of a single helically-shaped thread so that the space between the outer 698 and inner 700 caps can be adjusted by rotated the outer cap 698. In another form, the threads 702 are a series of ring-shaped ridges that engage the notches in a snap fit manner, so that the space between the outer 698 and inner 700 caps is adjusted in a telescoping manner. Both the outer cap 698 and the inner cap 700 have end faces 706, 708 that define an expression opening 710 and a lancet opening 712, respectively. Like before, the lancet opening 712 is sized (S1) to flatten the skin around the lancet so as to precisely control the penetration of the lancet 50, and the expression opening 712 is sized (S2) to express fluid. An expression ridge 714, which is configured to express fluid, surrounds the expression opening 710. As mentioned above, the space between the end faces 706, 708 of the caps 698, 700 is adjustable, and by being adjustable, the sampling device 696 can provided variable opening sizes. So for example, after lancing the skin with the end face 706 of the outer cap 698 positioned flush against the end face 708 of the inner cap 700 (FIG. 57A), the outer cap 698 can be extended such that the sampling device 696 has the effective opening size (S2) of the expression opening 710 (FIG. 57B) so that fluid can be expressed from alternate sites.

Figure 58:
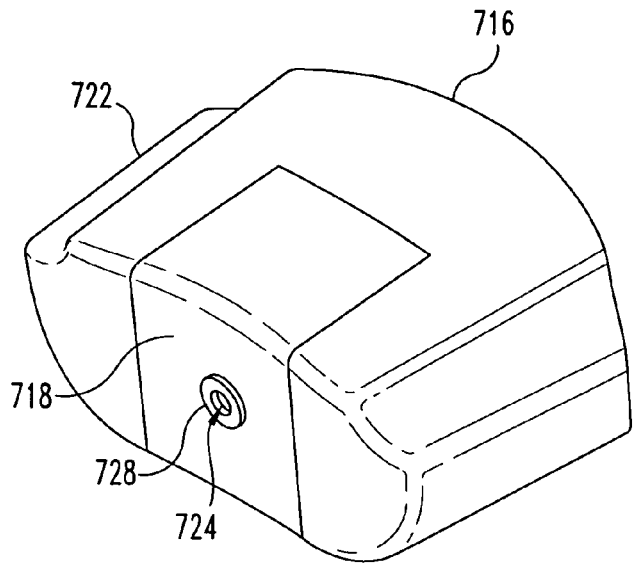
FIG. 58 is a perspective view of a sampling device according to still yet another embodiment.
Figure 59:
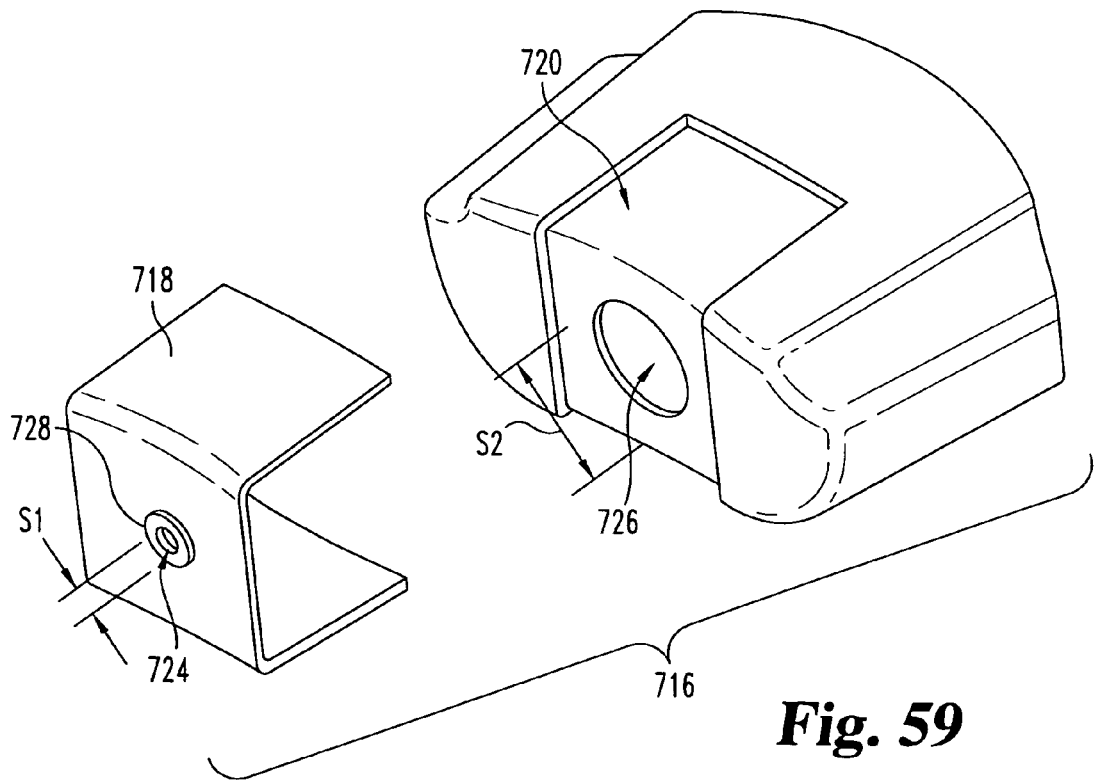
FIG. 59 is an exploded view of the FIG. 58 device.

Referring to FIGS. 58 and 59, a body fluid sampling device 716 with a detachable insert 718 for providing variable opening sizes according to another embodiment is illustrated. As shown, the insert 718 is frictionally fitted in an insert notch 720 formed in housing 722 of the sampling device 716. The insert 718 has a lancet opening 724 that is positioned to align with an expression opening 726. A reference ridge 728 for flattening the skin surrounds the lancet opening 724. The lancet opening 724 is sized (S1) to flatten the skin around the lancet so as to precisely control the penetration of the lancet 50, and the expression opening 726 is sized (S2) to express fluid from alternate sites. During lancing, the insert 718 is attached to the housing 722 so that the penetration depth of the lancet in the sampling device 716 can be controlled. After the skin is lanced, the insert 718 can be removed so that fluid can be expressed by pressing the expression opening 726 around the incision.

Figure 60:
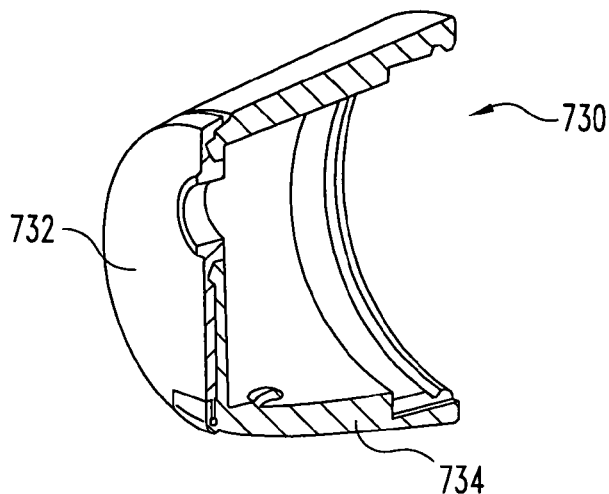
FIG. 60 is a perspective view of a cross section of a sampling device according to a further embodiment.
Figure 61:
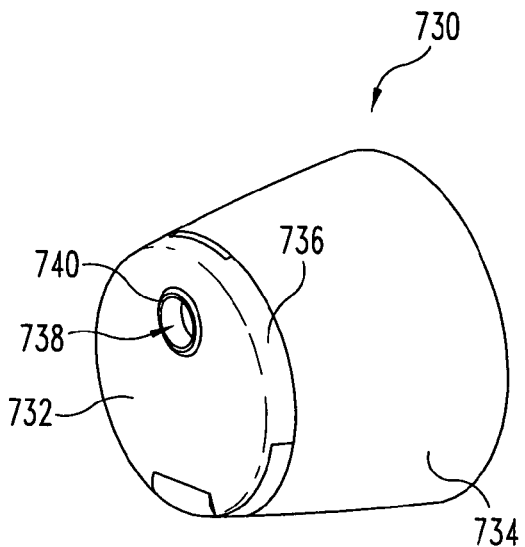
FIG. 61 is a perspective view of the FIG. 60 device in a lancing configuration.
Figure 62:
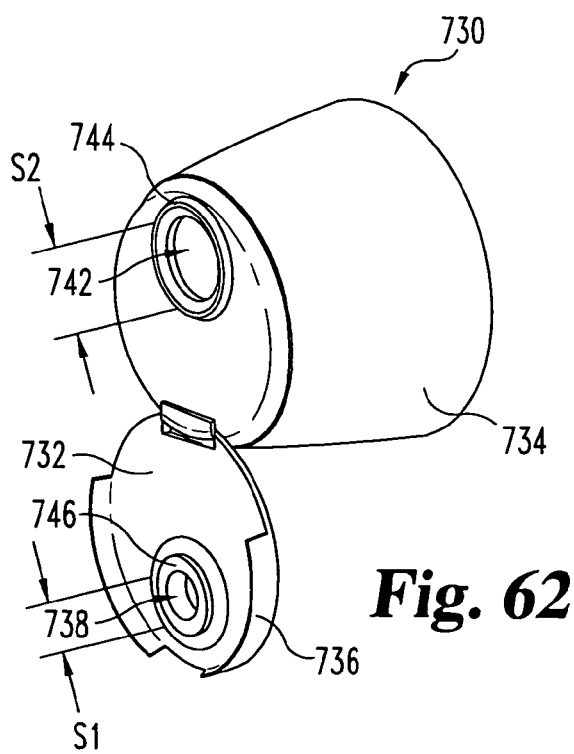
FIG. 62 is a perspective view of the FIG. 60 device in an expression configuration.

A cap assembly 730 for a sampling device according to a further embodiment is depicted in FIGS. 60, 61 and 62. The cap assembly 730 has a flip cap 732 that is pivotally coupled to a cap body 734. Although the illustrated cap assembly 730 has a frustoconical shape, it should be appreciated that the cap assembly 730 can have a different overall shape. The flip cap 732 is generally flat and has a body engagement flange 736 that frictionally secures the flip clap 732 when in a closed position, as illustrated in FIG. 61. As shown, the flip cap 732 has a lancet opening 738 that is sized (S1) to flatten the skin around the lancet so that penetration depth is controlled. Around the lancet opening 738, the flip cap 732 has a lancet ridge 740 that aids in flattening the skin around the lancet. The cap body 734 has an expression opening 742 that is sized (S2) larger than the lancet opening 738 so that fluid can be expressed from alternate sites. An expression ridge 744, which is configured to assist in the expression of fluid, surrounds the expression opening 742. To support the flip cap 732 around the expression opening 742 when closed, the flip cap 732 has an opening engagement member 746 that is configured to mate with the expression ridge 744 and opening 742 when the flip cap 732 is closed. During lancing the flip cap 732 is closed, as depicted in FIG. 61, and when needed to express fluid from alternate sites, the flip cap 732 can be flipped open so that fluid can be expressed from an incision by pressing the expression opening 742 around the incision.

As should be appreciated, the above-described devices can be incorporated into an integrated sampling device that further includes a capillary tube or some other wicking means for drawing the bodily fluid sample onto a test strip while the device remains positioned over the incision. Sampling device 330, which was described above with reference to FIGS. 21-23, is an example of one such integrated device. As previously mentioned, device 330 remains in contact with the skin as the fluid sample is drawn into the blade cavity 344 and deposited onto the test strip 336. It is contemplated that other devices described herein can be modified to collect and test a fluid sample in a similar fashion.

It also should be appreciated that with the above-described devices the user can also configure the devices ahead of time so that, for alternate sites, the lancet lances through only the expression opening. In this manner, the user does not have to remove the device from the incision site in order to change the opening size to express fluid because the device is already configured to express fluid. For example, in the flip cap design illustrated in FIGS. 39A and 39B, the user can pivot the flip cap 558 away from the housing 560, thereby exposing the expression opening 566, before lancing the skin at an alternate site. After lancing the skin, the user can simply press the device 556 against the skin to express fluid, without having to remove the device 556 to make any adjustments. It should be appreciated that this technique can be used in other devices that were described above.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected. All publications, patents, and patent applications cited in this specification are herein incorporated by reference as if each individual publication, patent, or patent application were specifically and individually indicated to be incorporated by reference and set forth in its entirety herein.

What is claimed is:

1. A method, comprising:
   lancing an incision in skin with a lancet of a sampling device;
   controlling penetration depth of the lancet by flattening skin around the lancet with a lancet opening of the device during said lancing;
   expressing fluid from the incision by pressing an expression opening of the sampling device around the incision, wherein the expression opening is larger than the lancet opening;
   wherein the sampling device includes a housing and a ball member that has the expression opening and the lancet opening rotatably coupled to the housing; and
   rotating the expression opening in position to express fluid after said lancing.
2. The method of claim 1, wherein:
   the ball member is rotatably coupled to the housing through one or more pivot pins; and
   said rotating the expression opening includes rotating the ball member about the one or more pivot pins.
3. The method of claim 2, wherein:
   the lancet opening is at most 2.5 mm in diameter; and
   said lancing the incision includes extending the lancet through the lancet opening that is at most 2.5 mm in diameter.
4. The method of claim 3, wherein said expressing includes pressing the expression opening around the incision that is at least 7.0 mm in diameter.
5. The method of claim 2, wherein said expressing includes pressing the expression opening around the incision that is at least 7.0 mm in diameter.
6. The method of claim 2, wherein:
   the lancet opening is at most 2.5 mm in diameter; and
   said lancing the incision includes extending the lancet through the lancet opening that is at most 2.5 mm in diameter.
7. The method of claim 6, wherein said expressing includes pressing the expression opening around the incision that is at least 7.0 mm in diameter.
8. The method of claim 1, wherein said expressing includes pressing the expression opening around the incision that is at least 7.0 mm in diameter.
9. A method, comprising:
   providing a sampling device that includes a lancet and a lancet opening that is sized to generally flatten skin around the lancet during lancing, wherein the sampling device has an expression opening that is sized larger than the lancet opening to express fluid;
   placing the lancet opening against the skin to generally flatten the skin;
   forming an incision in the skin with the lancet by extending the lancet through the lancet opening after said placing of the lancet opening against the skin;
   adjusting the sampling device so that the expression opening is able to express the fluid after said forming the incision;
   expressing the fluid from the incision by pressing the expression opening around the incision;
   the sampling device includes a ball that has the lancet opening and the expression opening; and
   said adjusting includes rotating the ball so that the expression opening is positioned to express the fluid.
10. The method of claim 9, wherein:
    the lancet opening is at most 2.5 mm in diameter; and
    said forming the incision includes extending the lancet through the lancet opening that is at most 2.5 mm in diameter.
11. The method of claim 10, wherein:
    the expression opening is at least 7.0 mm in diameter; and
    said expressing includes pressing the expression opening around the incision that is at least 7.0 mm in diameter.
12. The method of claim 11, wherein:
    the ball is rotatably coupled to the sampling device through one or more pivot pins; and
    said adjusting includes rotating the ball about the one or more pivot pins.
13. The method of claim 10, wherein:
    the ball is rotatably coupled to the sampling device through one or more pivot pins; and
    said adjusting includes rotating the ball about the one or more pivot pins.
14. The method of claim 9, wherein:
    the expression opening is at least 7.0 mm in diameter; and
    said expressing includes pressing the expression opening around the incision that is at least 7.0 mm in diameter.
15. The method of claim 14, wherein:
    the ball is rotatably coupled to the sampling device through one or more pivot pins; and
    said adjusting includes rotating the ball about the one or more pivot pins.
16. The method of claim 9, wherein:
    the ball is rotatably coupled to the sampling device through one or more pivot pins; and
    said adjusting includes rotating the ball about the one or more pivot pins.
17. A method, comprising:
    rotating a ball member of a lancing device to a first position where a first opening in the ball member faces skin;
    placing the ball member in the first position against the skin;
    cutting an incision in skin by extending a lancet through the first opening in the ball member;

rotating the ball member to a second position where a second opening in the ball member faces the skin, the second opening being larger than the first opening; and expressing fluid from the incision by pressing the second opening against the skin around the incision with the ball member in the second position.

18. The method of claim 17, in which said expressing includes pressing the second opening against the skin that is at least 7.0 mm in diameter.

19. The method of claim 18, in which said cutting includes extending the lancet through the first opening that is at most 2.5 mm in diameter.

20. The method of claim 19, wherein:

the ball member is rotatably coupled to the lancing device through one or more pivot pins; and said rotating the ball member includes rotating the ball member about the one or more pivot pins.

21. The method of claim 18, wherein:

the ball member is rotatably coupled to the lancing device through one or more pivot pins; and said rotating the ball member includes rotating the ball member about the one or more pivot pins.

22. The method of claim 17, in which said cutting includes extending the lancet through the first opening that is at most 2.5 mm in diameter.

23. The method of claim 22, wherein:

the ball member is rotatably coupled to the lancing device through one or more pivot pins; and said rotating the ball member includes rotating the ball member about the one or more pivot pins.

24. The method of claim 17, wherein:

the ball member is rotatably coupled to the lancing device through one or more pivot pins; and said rotating the ball member includes rotating the ball member about the one or more pivot pins.

* * * * *

UNITED STATES PATENT AND TRADEMARK OFFICE
CERTIFICATE OF CORRECTION

PATENT NO.       : 7,736,322 B2
APPLICATION NO.  : 10/744167
DATED            : June 15, 2010
INVENTOR(S)      : Steven N. Roe It is certified that error appears in the above-identified patent and that said Letters Patent is hereby corrected as shown below:

Col. 24, line 11, replace --unshaped-- with "u-shaped"

Signed and Sealed this

Seventeenth Day of August, 2010

David J. Kappos
*Director of the United States Patent and Trademark Office*